(12) United States Patent
Nabavi et al.

(10) Patent No.: US 12,387,477 B2
(45) Date of Patent: Aug. 12, 2025

(54) CONJOINED TWIN NETWORK FOR TREATMENT AND ANALYSIS

(71) Applicant: University of Connecticut, Farmington, CT (US)

(72) Inventors: Sheida Nabavi, Wellesley, MA (US); Clifford Yang, Farmington, CT (US); Jun Bai, Cincinnati, OH (US)

(73) Assignee: UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 18/821,269

(22) Filed: Aug. 30, 2024

(65) Prior Publication Data

US 2024/0428577 A1    Dec. 26, 2024

Related U.S. Application Data

(63) Continuation-in-part of application No. 18/096,700, filed on Jan. 13, 2023.

(Continued)

(51) Int. Cl.
*G06V 10/82* (2022.01)
*G06N 3/0455* (2023.01)
(Continued)

(52) U.S. Cl.
CPC ........... *G06V 10/82* (2022.01); *G06N 3/0455* (2023.01); *G06N 3/048* (2023.01); *G06T 7/0012* (2013.01);
(Continued)

(58) Field of Classification Search
CPC ......... G06T 7/0014; G06T 2207/20081; G06T 2207/20084; G06T 2207/30068;
(Continued)

(56) References Cited

U.S. PATENT DOCUMENTS

2008/0183646 A1    7/2008   Harris et al.
2010/0010831 A1    1/2010   Fueyo et al.
(Continued)

OTHER PUBLICATIONS

International Search Report and Written Opinion issued in related application No. PCT/US23/10799 mailed on Apr. 13, 2023.
(Continued)

*Primary Examiner* — Jose L Couso
(74) *Attorney, Agent, or Firm* — CANTOR COLBURN LLP

(57) ABSTRACT

An apparatus for treating an abnormality includes a processor and a non-transitory computer readable medium that includes a first convolutional neural network (CNN) having weights and a second CNN in parallel with the first CNN and sharing the weights, the second CNN being joined to the first neural network by a distance function. The medium includes instructions that when executed by the processor implements a method. The method includes receiving a first image dataset of an area of interest and processing the first image dataset using the first CNN and receiving a second image dataset of the area of interest obtained prior to the first image dataset and processing the second image dataset using the second CNN. The method also includes identifying the abnormality using an output of the distance function wherein the identifying influences treatment of the abnormality.

21 Claims, 33 Drawing Sheets

Related U.S. Application Data

(60) Provisional application No. 63/299,313, filed on Jan. 13, 2022.

(51) Int. Cl.
*G06N 3/048* (2023.01)
*G06T 7/00* (2017.01)
*G16H 20/00* (2018.01)

(52) U.S. Cl.
CPC ... *G16H 20/00* (2018.01); *G06T 2207/20081* (2013.01); *G06T 2207/20084* (2013.01); *G06V 2201/032* (2022.01)

(58) Field of Classification Search
CPC . G06T 2207/30096; G06T 2207/10116; G06T 7/0012; G06T 7/20; G06T 7/0016; G06T 7/70; G06T 2207/30024; G06T 2207/10056; G06T 2207/10068; G06T 2207/10081; G06T 2207/10101; G06T 2207/10132; G06T 2207/30028; G06T 2207/30041; G06T 2207/30088; G06T 7/12; G06T 3/4046; G06T 5/60; G06T 9/002; G06T 2207/20076; A61B 6/502; A61B 8/466; A61B 8/483; A61B 8/485; G06V 2201/03; G06V 10/25; G06V 20/69; G06V 20/698; G06V 30/19173; G06V 10/454; G06V 10/54; G06V 10/774; G06V 10/82; G06V 20/41; G06V 30/18057; G16H 50/20; G16H 30/20; G16H 30/40; G16H 50/30; G16H 50/50; G16H 50/70; G16H 20/90; A61N 5/1039; A61N 5/1049; A61N 5/1067; A61N 5/1058; A61N 5/1062; A61N 5/1037; A61N 5/1038; G06N 3/02; G06N 3/08–088; G06N 3/0445; G06N 3/0454; G06N 3/4046; G06N 7/00; G06N 7/01; G06N 20/00; G06K 7/1482; G06F 18/214; G06F 18/22; G06F 18/241; G06F 18/24; G06F 18/2411; G06F 18/2415; Y10S 128/925

See application file for complete search history.

(56) References Cited

U.S. PATENT DOCUMENTS

| | | |
|---|---|---|
| 2012/0226644 A1 | 9/2012 | Jin et al. |
| 2016/0093062 A1 | 3/2016 | Theis |
| 2018/0218502 A1* | 8/2018 | Golden ............... G06T 7/11 |
| 2019/0030371 A1* | 1/2019 | Han .................. A61N 5/1039 |
| 2019/0164287 A1* | 5/2019 | Gregson ............. G16H 30/40 |
| 2019/0244347 A1* | 8/2019 | Buckler ............... G06F 18/24 |
| 2019/0332900 A1* | 10/2019 | Sjolund ............... G06T 9/002 |
| 2020/0001114 A1 | 1/2020 | Bharat |
| 2020/0360731 A1 | 11/2020 | Tilly et al. |
| 2021/0375458 A1* | 12/2021 | Chen ................... G16H 50/20 |
| 2022/0020151 A1* | 1/2022 | Sainz de Cea ....... G06T 7/0016 |
| 2022/0037024 A1* | 2/2022 | Yoo ..................... G06N 20/00 |
| 2022/0180514 A1* | 6/2022 | Vlasimsky ............ G06T 7/11 |
| 2022/0375602 A1* | 11/2022 | Jaber ................... G06V 10/454 |
| 2023/0207134 A1* | 6/2023 | Hegde .................. G06V 10/82 382/133 |
| 2023/0329646 A1* | 10/2023 | Zhou .................. G16H 50/30 |
| 2024/0185417 A1* | 6/2024 | Chen ................... G06T 7/0012 |

OTHER PUBLICATIONS

Bai et al., "Feature fusion Siamese network for breast cancer detection comparing current and prior mammograms", Medical Physics, Received: Dec. 6, 2021; 16 pages.

Chung et al., "Learning Deep Representations of Medical Images using Siamese CNNs with Application to Content-Based Image Retrieval," 31st Conference on Neural Information Processing Systems, Dec. 2017.

Li et al., "Automated Assessment and Tracking of COVID-19 Pulmonary Disease Severity on Chest Radiographs Using Convolutional Siamese Neural Networks," Radiology: Artificial Intelligence, vol. 2, Iss. 4, Jul. 2020.

Shorfuzzaman et al., "MetaCOVID: A Siamese neural network framework with contrastive loss for n-shot diagnosis of COVID-19 patients," Pattern Recognition, Oct. 2021.

Zbontar et al., "Barlow Twins: Self-Supervised Learning via Redundancy Reduction," Proceedings of the 38th International Conference on Machine Learning, Jul. 2021.

Bai et al., "Unsupervised feature correlation model to predict breast abnormal variation maps in longitudinal mammograms", Computerized Medical Imaging and Graphics, vol. 113, Jan. 20, 2024, 12 pages.

* cited by examiner

| Building Block | Layer | Input Dimension | Output Dimension |
|---|---|---|---|
| Block 1 | conv 7 x 7 @ 64 | 1024 x 1024 | 512 x 512 x 64 |
| Block 2 | conv 1 x 1 @ 64 | 256 x 256 x 64 | 256 x 256 x 64 |
|  | conv 3 x 3 @ 64 | 256 x 256 x 64 | 256 x 256 x 64 |
|  | conv 1 x 1 @ 256 | 256 x 256 x 64 | 256 x 256 x 256 |
| Block 3 | conv 1 x 1 @ 128 | 256 x 256 x 256 | 128 x 128 x 128 |
|  | conv 3 x 3 @ 128 | 128 x 128 x 128 | 128 x 128 x 128 |
|  | conv 1 x 1 @ 512 | 128 x 128 x 128 | 128 x 128 x 512 |
| Block 4 | conv 1 x 1 @ 256 | 128 x 128 x 512 | 64 x 64 x 256 |
|  | conv 3 x 3 @ 256 | 64 x 64 x 256 | 64 x 64 x 256 |
|  | conv 1 x 1 @ 1024 | 64 x 64 x 256 | 64 x 64 x 1024 |
| Block 5 | conv 1 x 1 @ 512 | 64 x 64 x 1024 | 32 x 32 x 512 |
|  | conv 3 x 3 @ 512 | 32 x 32 x 512 | 32 x 32 x 512 |
|  | conv 1 x 1 @ 2048 | 32 x 32 x 512 | 32 x 32 x 2048 |
| Last Layer | Average pooling | 32 x 32 x 2048 | 8 x 8 x 2048 |

FIG.6

| Model | Accuracy | Sensitivity | Precision | Specificity | F1 | AUC |
|---|---|---|---|---|---|---|
| VGG | 0.78 ± 0.01 | 0.78 ± 0.04 | 0.77 ± 0.02 | 0.78 ± 0.03 | 0.78 ± 0.01 | 0.85 ± 0.02 |
| ResNet | 0.81 ± 0.02 | 0.82 ± 0.05 | 0.79 ± 0.02 | 0.80 ± 0.04 | 0.80 ± 0.02 | 0.89 ± 0.03 |
| LLSTM | 0.87 ± 0.02 | 0.88 ± 0.03 | 0.86 ± 0.02 | 0.86 ± 0.02 | 0.87 ± 0.02 | 0.93 ± 0.01 |
| FFS–CNN | 0.92 ± 0.01 | 0.92 ± 0.03 | 0.91 ± 0.03 | 0.91 ± 0.03 | 0.91 ± 0.01 | 0.96 ± 0.00 |

FIG. 7

Parallel networks: feature extraction from current and previous year image

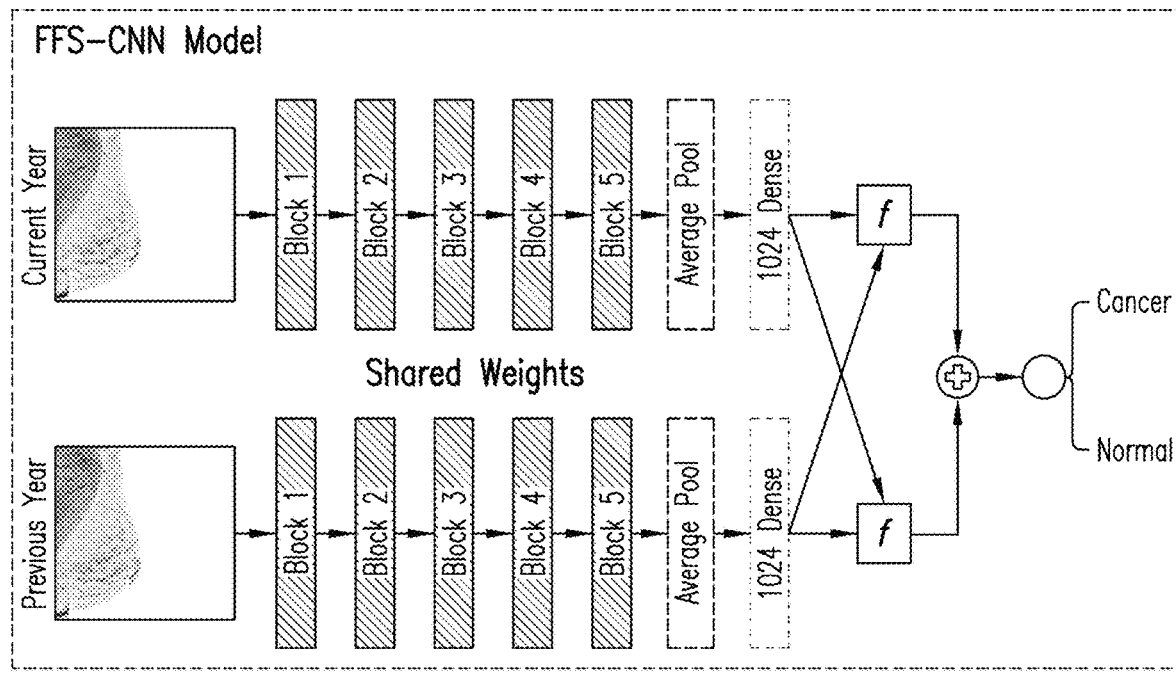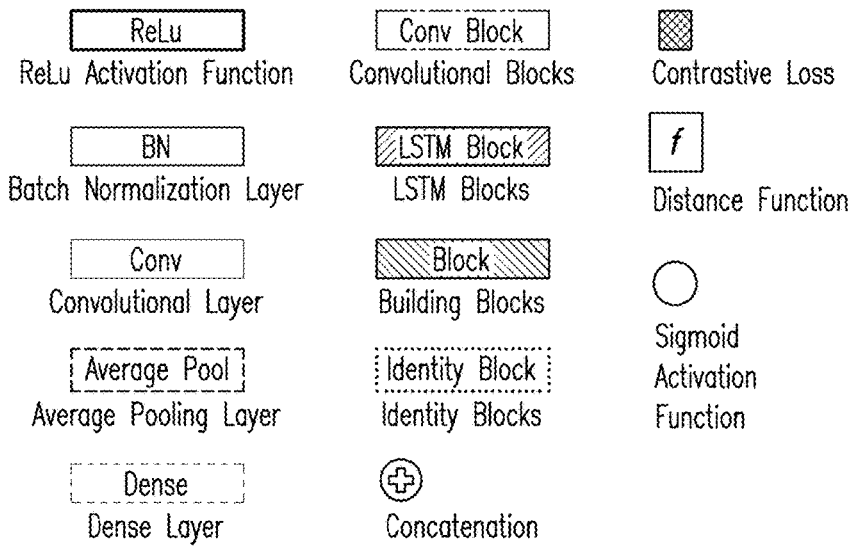
FIG.9F

FIG.19B

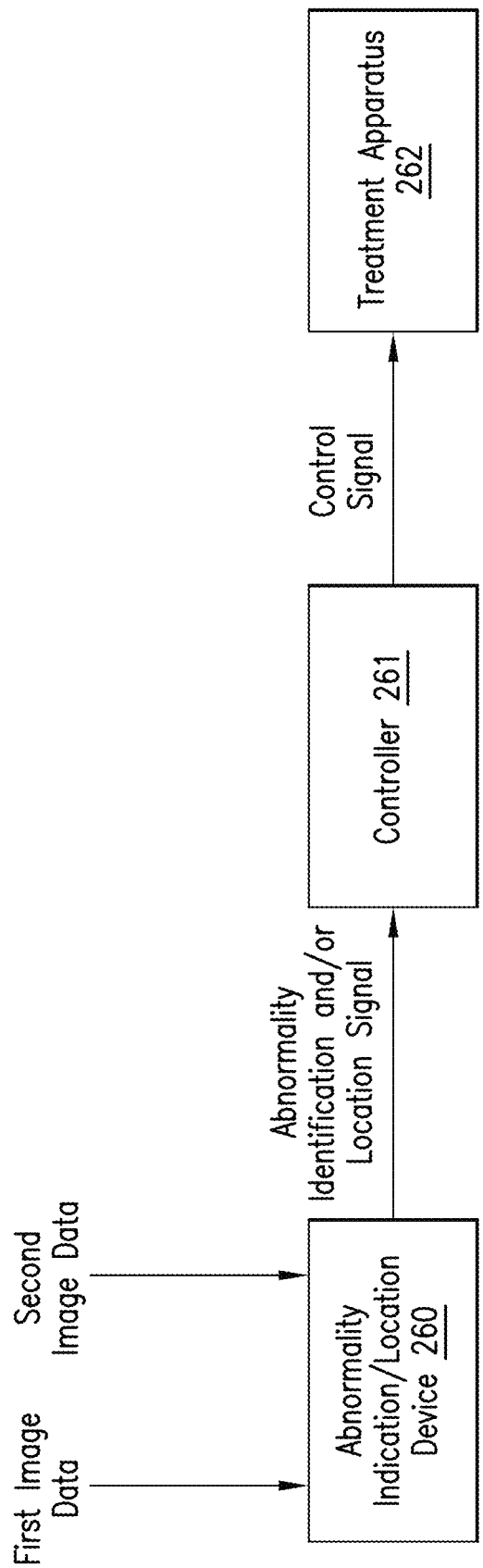

CONJOINED TWIN NETWORK FOR TREATMENT AND ANALYSIS

CROSS-REFERENCE TO RELATED APPLICATIONS

This application claims the benefit of U.S. patent application Ser. No. 18/096,700, filed Jan. 13, 2023, which in turn claims the benefit of U.S. Provisional Application No. 63/299,313, filed Jan. 13, 2022, the disclosures of which are incorporated herein by reference in their entirety.

BACKGROUND

Early detection and treatment of abnormal tissues can lead to positive outcomes in treatment and survival. For example, abnormal tissue may be indicative of breast and other cancers. Breast cancer is the most common cancer in women and is also the leading cause of death for women between the ages of 20 and 59. Screenings for breast cancer and other abnormal tissues have provided chronological documentation of tissue growth and development. Computer-aided detection reduces the risk of overlooking growth, but the over-detection and under-detection provided by these methods can increase the recall rate when used to interpret mammograms and other data, causing misdiagnosis and costs to rise.

SUMMARY

Methods, apparatuses, systems, and techniques are described for treatment and analysis of patients. For a better understanding of the underlying concepts, there follows specific non-limiting examples:

A method includes receiving first data based on a region of interest of tissue. The first data may be captured to represent the tissue according to a first moment. The method also includes receiving second data based on the region of interest. The second data may be captured to represent the tissue according to a second moment different from the first moment. The method also includes determining features of the first data according to a first network. The first network may comprise weights. The method also includes determining features of the second data according to the weights. The method also includes determining an input based on the features of the first data and the features of the second data. The method also includes determining an abnormality in the tissue according to an application of the input on a second network. The method may also include treating a patient or adjusting treatment of the patient diagnosed by one or more of these steps.

An apparatus includes one or more processor. The apparatus includes one or more non-transitory computer-readable medium. The one or more non-transitory computer-readable medium includes a first network having weights and a second network configured to output an indication of an abnormality. The input of the second network may be based on an output of the first network. The one or more non-transitory computer-readable medium includes instructions operable upon execution by the one or more processor to receive first data based on a region of interest of tissue. The first data may be captured to represent the tissue according to a first moment. The instructions are further operable upon execution by the one or more processor to receive second data based on the region of interest. The second data may be captured to represent the tissue according to a second moment different from the first moment. The instructions are further operable upon execution by the one or more processor to determine features of the first data according to the first network and the weights. The instructions are further operable upon execution by the one or more processor to determine features of the second data according to the weights. The instructions are further operable upon execution by the one or more processor to determine the input based on the features of the first data and the features of the second data. The instructions are further operable upon execution by the one or more processor to determine an abnormality in the tissue according to an application of the input on a second network.

A method includes receiving first data based on a region of interest of tissue. The first data may be captured to represent the tissue according to a first moment. The method includes treating or adjusting treatment to a patient associated with the tissue. The patient may be diagnosed by a process that includes receiving second data based on the region of interest. The second data may be captured to represent the tissue according to a second moment different from the first moment. The process may include determining features of the first data according to a first network. The first network may include weights. The process may include determining features of the second data according to the weights. The process may include determining an input based on the features of the first data and the features of the second data. The process may include determining an abnormality in the tissue according to an application of the input on a second network.

Disclosed is an apparatus for treating an abnormality. The apparatus includes a processor and a non-transitory computer readable medium. The non-transitory computer readable medium includes a first convolutional neural network (CNN) having weights and a second convolutional neural network in parallel with the first CNN and sharing the weights of the first CNN, the second CNN being joined to the first neural network by a distance function. The non-transitory computer readable medium also includes instructions that when executed by the processor implements a method. The method includes receiving a first image dataset of an area of interest and processing the first image dataset using the first CNN, receiving a second image dataset of the area of interest obtained prior to the first image dataset and processing the second image dataset using the second CNN, identifying the abnormality based on an output of the distance function, and outputting an indication of the abnormality, wherein the indication influences administering or adjusting treatment of the abnormality.

Also disclosed is a non-transitory computer readable medium for treating an abnormality. The non-transitory computer readable medium includes a first convolutional neural network (CNN) having weights and a second convolutional neural network in parallel with the first CNN and sharing the weights of the first CNN, the second CNN being joined to the first CNN by a distance function. The non-transitory computer readable medium also includes instructions that when executed by the processor implements a method. The method includes receiving a first image dataset of an area of interest and processing the first image dataset using the first CNN, receiving a second image dataset of the area of interest obtained prior to the first image dataset and processing the second image dataset using the second CNN, identifying the abnormality based on an output of the distance function, and outputting an indication of the abnormality, wherein the indication influences administering or adjusting treatment of the abnormality.

Further disclosed is a method for treating an abnormality. The method includes receiving a first image dataset of an area of interest and processing the first image dataset using a first convolutional neural network (CNN), the first CNN having weights and receiving a second image dataset of the area of interest obtained prior to the first image dataset and processing the second image dataset using a second convolutional neural network, the second CNN being in parallel with the first CNN and sharing the weights of the first CNN, the second CNN being joined to the first neural network by a distance function, and identifying the abnormality based on an output of the distance function. The method further includes influencing application or adjustment of treatment of the abnormality based on identification of the abnormality.

BRIEF DESCRIPTION OF THE DRAWINGS

In order to provide understanding techniques described, the figures provide nonlimiting examples in accordance with one or more implementations of the present disclosure, in which:

FIG. 6 illustrates an example network architecture;

FIG. 7 illustrates example results;

FIGS. 9A-9F, collectively referred to as FIG. 9, are schematic diagrams of baseline models;

FIGS. 19A and 19B, collectively referred to as FIG. 19, depict aspects of a demonstration of special cases;

FIG. 22 depicts aspects of apparatuses for treating a patient having an abnormality.

DETAILED DESCRIPTION

Figure 1:
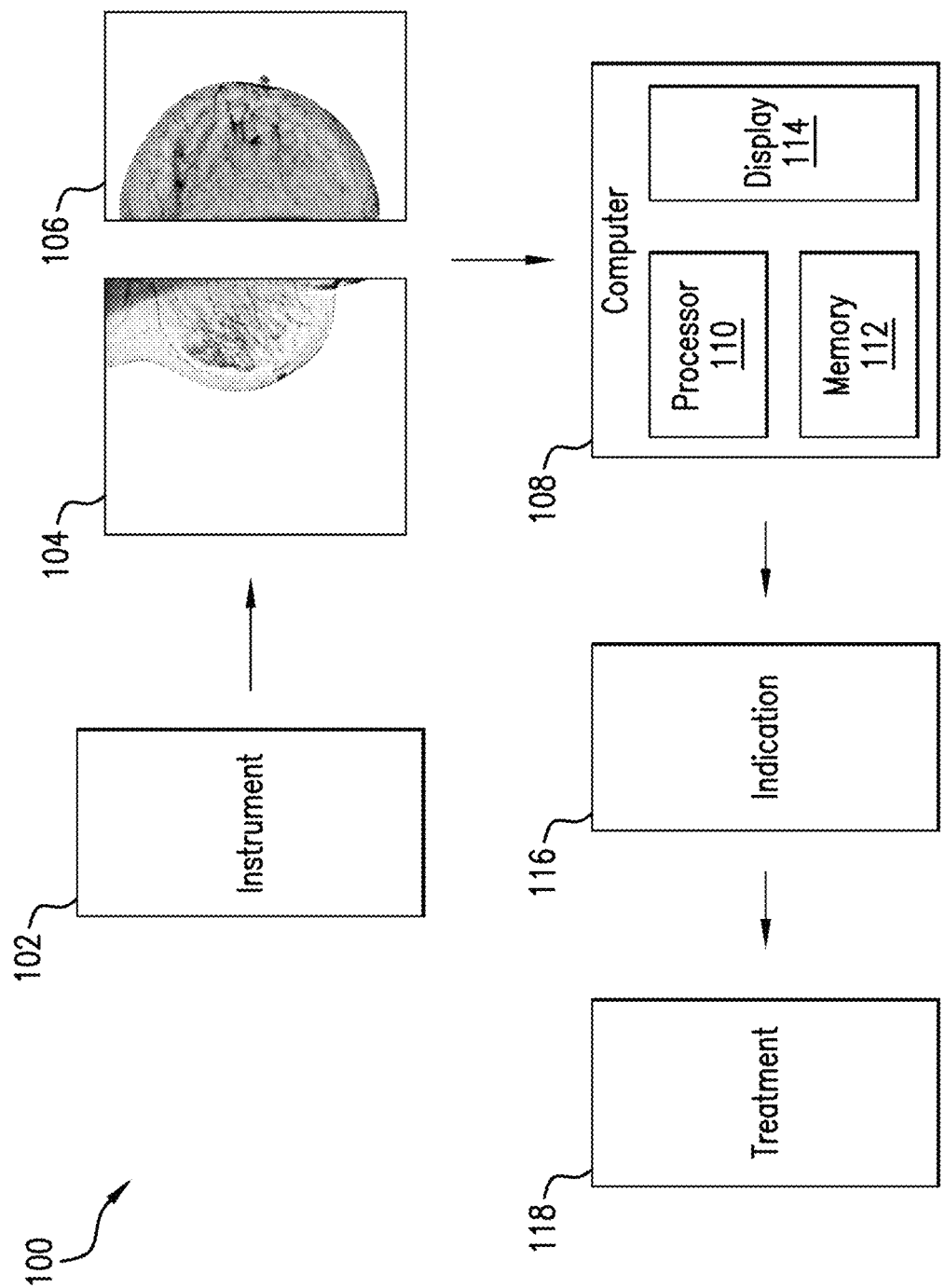
FIG. 1 illustrates an example system for treating a patient with abnormal tissue.

Full-field digital mammography (FFDM) scans are among the most challenging medical images for automatic cancer classification, due to the characteristics of breast tissues. The heterogeneous tree-shaped structure of the breast has a connected tissue network that supports glandular tissues. These breast tissues are also surrounded by fat and covered with skin. Thus, a breast tumor can be occult because of overlaying glandular architecture. In addition, some breast tumors show identical characteristics of glandular tissues. Cancer may be identified based on the features extracted from individual breast exams. As discussed, some breast tumors look similar to breast normal tissues, making the classification of objects and abnormal tissues challenging.

Detection of abnormal tissue can be achieved with higher levels of accuracy than previously attained by using a conjoined twin network that fuses features determined based on neural networks (e.g., convolutional neural networks) to compare data (e.g., images) from previous screenings to data from contemporaneous screenings to identify changes in tissue that may be abnormal. The data may be used as paired inputs to predict the probability of malignancy. One or more distance learning functions may be employed to compare features detected within the data. The architecture may be configured to receive high-dimensional input for detection of very small malignancies in dense breasts (e.g., microcalcifications, occult tumors). For example, the architecture of one or more of the neural networks and distance learning functions discussed herein constitute a technical improvement to the art not previously realized. The architecture disclosed herein provides enhanced treatment options and treatment accuracy for patients to reduce the risk of overlooking growth and reduce the over-detection and under-detection of such growths, reducing misdiagnosis and the over-treatment or undertreatment of disease. The present disclosure at least presents improvements to machine learning architectures and the technical field of tumor treatment.

In order to provide some context, aspects of certain terms are presented. As used herein, the term "weights" generally references to the real values that are associated with each input/feature and they convey the importance of that corresponding feature in predicting the final output. Features with weights that are close to zero are said to have lesser importance in the prediction process compared to the features with weights having a larger value. "Inputs" generally refers to a set of values for which an output value will be predicted or estimated. Inputs can be viewed as features or attributes in a dataset.

Networks may be employed to detect interclass and intraclass features. For example, two parallel networks may have the same or similar weights. The weights may be trained by a one-shot learning algorithm. A distance learning network may be used to compare the outputs from the respective networks. For example, the distance learning network may measure the distance between the feature maps from each of the networks and then applies a fully connected or dense layer to learn the differences between the feature maps (e.g., interclass features). The parallel network may have an architecture based on a residual network (e.g., RESNET). A distance learning network may be based on a correlation matrix that compares current and previous images. For example, an N×N symmetric correlation matrix C in RN×N, where N is the size of the feature vectors and employs a shallow CNN to generate similarity feature vector. A loss function may include Barlow loss. The Barlow loss may act as a regularizer or normalizer. For example, the loss function (e.g., the function that determines model performance, or portion thereof) may be based on a Barlow loss function described in Equations 1 and 2 below.

$$B_{loss} \triangleq \sum_i (1 - C_{ii})^2 + \lambda \sum_i \sum_{j \neq i} C_{ij}^2 \quad (1)$$

where $\lambda$ is a predetermined quantity (e.g., a positive constant) that trades off between $\Sigma i(1-C_{ii})^2$ and $\Sigma i \: \Sigma_{j \neq i} C_{ij}^2$, and where C is the cross-correlation matrix computed between outputs of the networks (e.g., networks 350, 370) along the batch dimension: e.g., $$C_{ij} \triangleq \frac{\sum_b z^A_{b,i} z^B_{b,j}}{\sqrt{\sum_b (z^A_{b,i})^2} \sqrt{\sum_b (z^B_{b,j})^2}} \quad (2)$$

where b indexes batch samples and i, j index the vector dimension based on the networks (e.g., networks 350, 370). For example, the vector dimension may be based on one or more outputs of the networks. C is a square matrix sized with a dimensionality based on the networks (e.g., networks 350, 370). For example, C may be based on one or more outputs of the networks. The C matrix may be comprised of values between negative one and positive one. Normalization may transform network information (e.g., input information) to a predetermined scale (e.g., between 0 and 1). Regularization may transform weights, through training and the loss function, to improve performance (e.g., reduce over-fitting).

The feature representations may allow comparisons of the data using one or more distance functions. For example, the distance function may measure the similarity between the two functions.

Referring to FIG. 1, an example system 100 for treating a patient with abnormal tissue in accordance with one or more implementations of the present disclosure is shown. The system 100 includes an instrument 102 for determining data associated with a patient. The instrument 102 may be an apparatus configured to collect tissue, electromagnetic waves, fluids, or other sensory information related to the patient. For example, the instrument may collect reflected or undisturbed X-rays, ultrasound waves, visual light waves, or other electromagnetic waves to provide data 104, 106 regarding tissue or other bodily components based on the patent. For the example shown, the instrument is configured to collect X-ray, computed tomography (CT), or magnetic-resonance images (MRI) from the patient to generate data 104, 106.

The data 104, 106 may be represented in various dimensions. For example, the data 104, 106 may be one-dimensional, two-dimensional, three-dimensional, multidimensional, or various combinations thereof. As shown, the data 104, 106 is a two-dimensional image representative of a breasts or mammary glands. For example, the data 104, 106 may be provided by the instrument as a pixel or voxel representation of the tissue. The data 104, 106 may further include metadata or relational data derived from the tissue, the instrument, or otherwise.

The data 104, 106 may be provided to a computer 108. The instrument 102 and the computer 108 may be unitary, sharing the same housing, or in communication with one another over a network or communications bus. For example, the instrument 102 may be configured to send the data 104, 106 to a repository. The repository may be in the cloud or otherwise situated. The repository may be configured to store and maintain numerous data sets from multiple patients. The computer 108 may be configured to access the repository over a network on demand. The data sets may be accessed for training or inference. For example, the computer 108 may be used to train a network stored within the memory 112 of the computer 108. The memory 112 may include various computer-readable storage mediums as discussed herein. A processor 110 or a combination of processors 110 may be used to conduct processing on the data 104, 106 and define a network stored within the memory 112. The processor 110 may be a combination of various processing types for generally processing and machine learning. For example, the processor 110 may include application specific integrated circuits (ASIC), field-programmable gate arrays (FPGA), graphics processing units, central processing units, or combinations thereof. The processing of data may be distributed across various classes and infrastructure. For example, the processing may be conducted in the cloud over multiple instances, containers, repositories, or combinations thereof. The networks and data may be stored over multiple instances, containers, repositories or combinations thereof.

The computer 108 may include a display 114 for providing an indication 116 of data categorization. For example, the display 114 may display a category of the data 104, 106 based on a network stored within the memory 112. The display 114 may be located with the computer 108 or near a patient room or instrument room.

The indication 116 may be categorical (e.g., normal, abnormal, unknown), probabilistic (e.g., 25% probability of abnormality), or otherwise. The indication 116 may be provided to a repository or online medical system. For instance, the indication 116 may be communicated to a patient, doctor, or other medical personnel through an online portal. Medical personnel may apply or adjust treatment 118 based on the indication. For example, an indication 116 suggesting that the tissue is abnormal would compel medical personnel to perform surgery, chemotherapy, hormonal therapy, immunotherapy, or radiation therapy, additional testing, or a combination of surgery, chemotherapy, hormonal therapy, immunotherapy, radiation therapy, or additional testing. The dosage of certain therapies may be automatically or manually applied or adjusted based on the indication 116. For example, the quantity or periodicity of chemotherapy or other therapies may be adjusted based on the indication 116. The screening periodicity may be adjusted based on the indication 116, adjusting or reducing medical costs. For example, the indication 116 may present a low probability of abnormality, requiring additional screen in one year instead of six months. Other applications or adjustments are contemplated.

Figure 2:
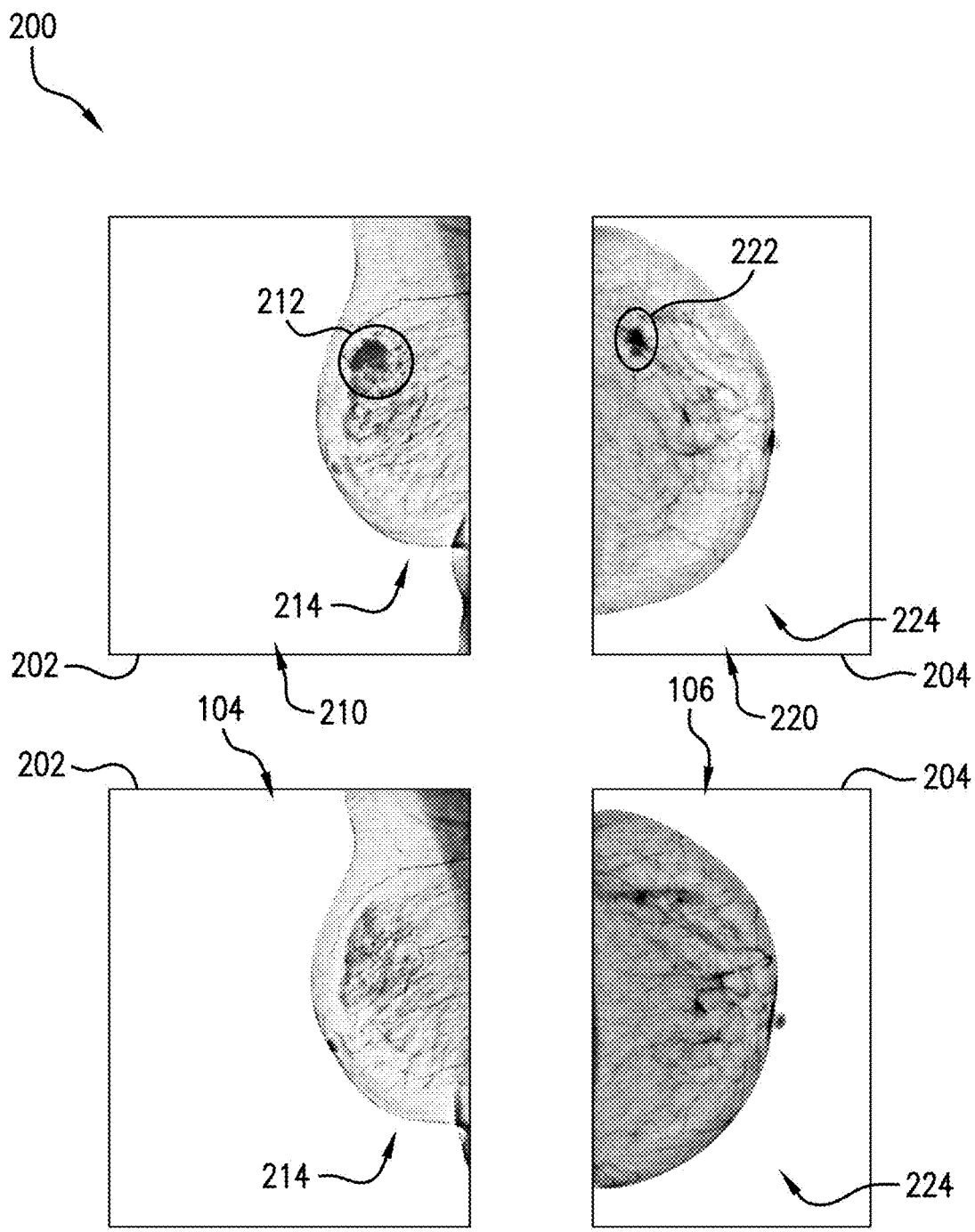
FIG. 2 illustrates example data based on tissue.

In FIG. 2, example data 200 based on tissue in accordance with one or more implementations of the present disclosure is shown. For example, data 104, 106 may be based on a region of interest 202, 204 for two different patients having respective tissues. The region of interest 202, 204 may be a portion of the data captured or all of the data captured by the instrument 102. For example, the region of interest 202, 204 may be based on an aspect of the instrument 102. The data 104, 106 may be captured according to a first moment. For example, breast mammograms may be captured using FFDM.

The patient may be screened annually or otherwise for abnormalities within the breast tissue. In this way, the data 104, 106 may be captured according to a first moment. The first moment may be a specific day or time when the data 104, 106 is captured according to the screening schedule. The data 104, 106 may be defined based on when the complete set of data is stored in a repository, an average time that the data was taken or otherwise. For example, the data may be captured over a week and assigned a moment pertaining to the time that the data 104, 106 is stored within the repository. The data 210, 220 may be captured according to a second moment. For example, the data 210, 220 may be captured a year, or about a year after the first moment. Other screening periods are contemplated (e.g., hourly, daily, biannually). The data 210, 220 may be captured from the same aspect with the same region of interest 202, 204 to maintain the continuity of the data 104, 106 captured according to the first moment with data 210, 220 captured according to the second moment. The data 104, 106 from the first moment may be compared with data 210, 220 from the second moment, indicating an abnormality of tissues 214, 224 of different patients, respectively.

Figure 3:
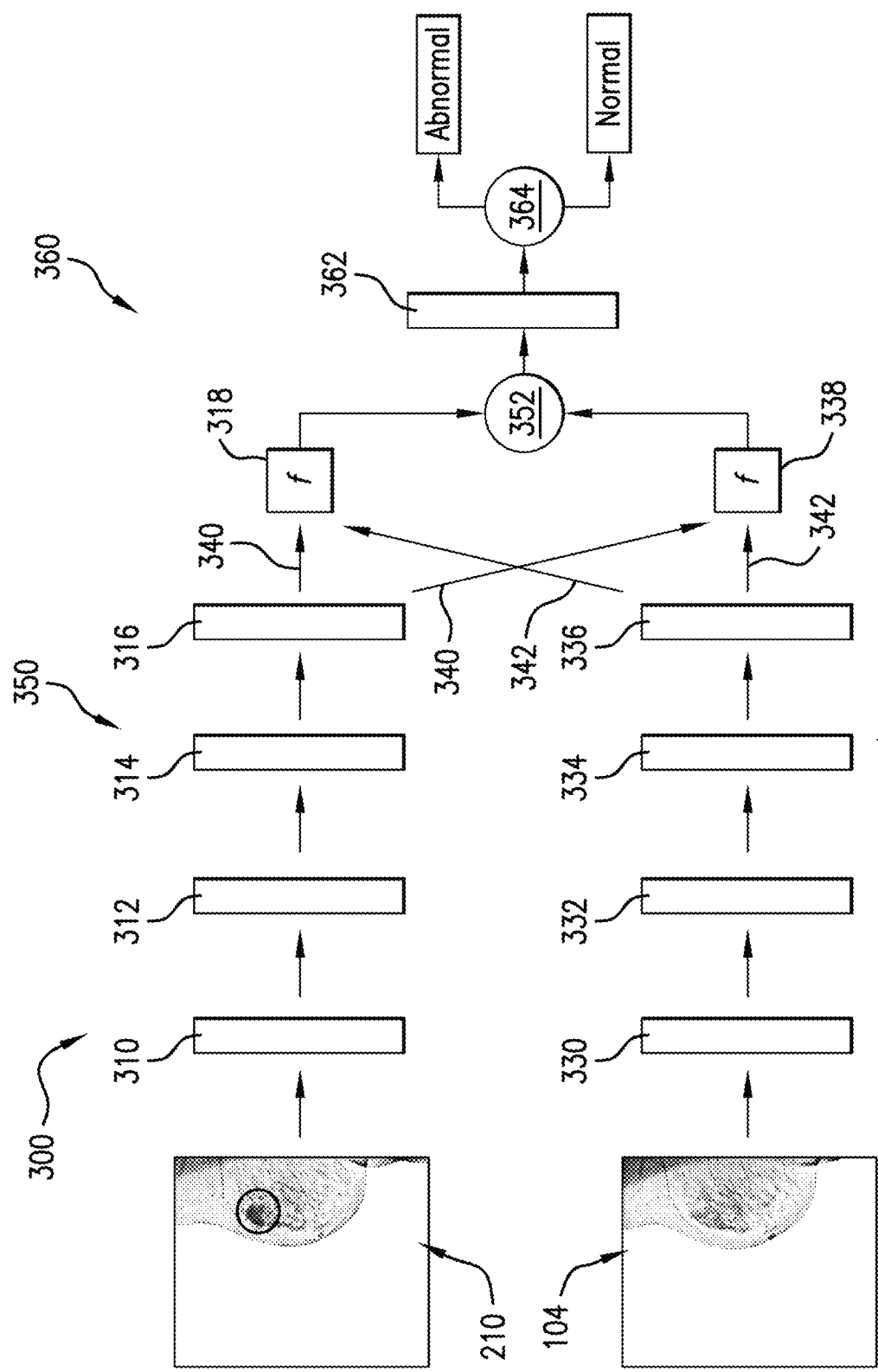
FIG. 3 illustrates an example conjoined twin network.

In FIG. 3, an example conjoined twin network 300 in accordance with one or more implementations of the present disclosure is shown. The networks shown may be stored on the memory 112 or one or more other computer-readable medium. A network 350 may be configured to receive data. For example, the network 350 may receive data 104 based on the first moment and data 210 based on the second moment. For example, the network 350 may receive the data 104 based on the first moment and data 210 based on the second moment, the data 104, 210 being obtained at different points in time from the same region of interest 202, 204 of patent tissue 214.

The network 350 may receive data 210 with the first layer 310. The network 350 may have the same weights, or substantially similar weights, as the network 370. For example, the first layer 310 of network 350 may have substantially similar weights to the first layer 330 of network 370. Substantially similar weights may be indicated where the weights are identical or based on a pre-trained network with one-shot training or application specific training. For instance, fine-tuning may change all or some of the weights. As data 210 and data 104 pass through the first layers 310, 330 of respective networks 350, 370 they are subjected to the same weights. As such, similar features are extracted from the data 104, 210 by respective layers 330, 310. The features extracted from data 210 are passed through layers 310, 312, 314 of network 350 to extract features. The layers 310, 312, 314 may have substantially similar weights of respective layers 330, 332, 334 of network 370. Various quantities or types (e.g., convolutional, pooling, fully connected) of layers may be used by the respective networks 350, 370.

For example, FIG. 6 depicts example convolutional layers (e.g., blocks) for one of the networks 350, 370. The layers 310, 312, 314 of network 350 may culminate in a pooling layer 316 (e.g., average pooling layer) of network 350. The layers 330, 332, 334 of network 370 may culminate in a pooling layer 336 (e.g., average pooling layer) of network 370. The resulting features 340, 342 of the respective pooling layers 316, 336 are then used to form an input 352 to network 360. The network 360 may be a fully connected network that learns the differences between the features maps that would indicate abnormal tissues from the data 104, 210. For example, a distance network may be used to quantify or determine the differences between features 340, 342 generated based on networks 350, 370 having substantially similar weights and original data 104, 210. Features 340, $f_c$, (e.g., features from contemporaneous data) defined by pooling layer 316 and features 342, fp, (e.g., features from previously gathered data) defined by pooling layer 336 are compared to define tissue categories (e.g., normal, abnormal, unknown), probabilities (e.g., 25% probability of abnormality), etc. Features 340, 342 may be flatted feature maps or feature vectors of the respective data 104, 210. The features may be used as inputs in distance learning functions 318, 338. For example, distance learning function 318 may be based on Equation 3.

$$d_1 = fc - f_P \tag{3}$$

where $d_1$ measures the pixel-wise distance (e.g., component distance) of fc and fp. Distance learning function 338 may be based on Equation 4.

$$d_2 = \sqrt{\sum_{j=0}^{m}(f_c^j - f_p^j)^2} \tag{4}$$

where d2 measures the scalar, Euclidean distance of fc and fp, and m is the size of the feature vectors. A concatenation block may operate as an input 352 to network 360, where d± is concatenated with d2 to build the distance feature for determination of abnormal tissue. The network 360 may include any number of layers 362. The layers 362 may output to a sigmoid function, as provided in Equation 5, that predicts the probability of dissimilarity (e.g., abnormal) or similarity (e.g., normal).

$$\hat{y} = \text{sigmoid}(w^T[d_1 \# d_2] + b, \tag{5}$$

where w denotes the vector of weights, b denotes bias, −H−denotes concatenation, and y represents the predicted probability of similarity. In such a way, the conjoined twin network can output the likelihood of abnormal changes between current year and previous year images. Binary cross-entropy may be used as a loss function to train the network.

Figure 4:
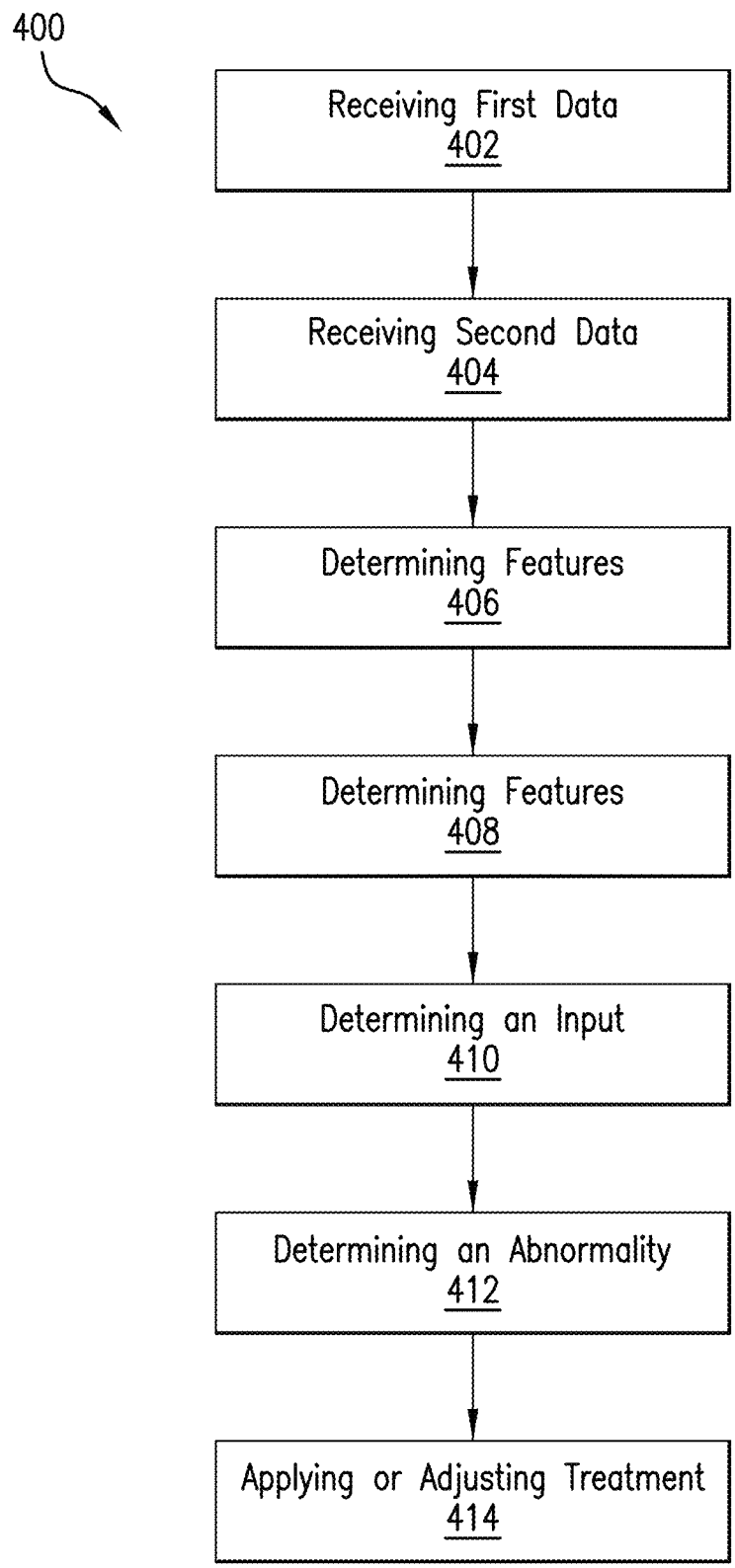
FIG. 4 illustrates an example method for determining an abnormality.

In FIG. 4, an example method 400 for determining an abnormality in accordance with one or more implementations of the present disclosure. The steps presented herein may be performed in whole or in part by any of the components described herein. Any of the steps may be omitted, duplicated, or rearranged. For example, in step 402 data may be received. The data may be data 104 that is captured according to a first moment. In step 404, data may be received. The data may be data 210 that is captured according to a second moment. The first moment may be different from the second moment. For example, the second moment may be after the first moment.

In step 406, features 340 may be determined according to a network 350 based on the data 210. The network 350 may include weights. The weights may be the same as the weights of network 370. In step 408, the features 342 of the data 104 may be determined according to the same weights as network 350. The features 342 may be determined by the network 350 or the network 370. In step 410, an input 352 (e.g., concatenation block) may be determined based on the features 340, 342. The input may be based on one or more distances determined between the features 340, 342. For example, the distance may be a pixel-wise distance. The pixel-wise distance may be based on a difference between a vector representation (e.g., series of component values) of the features 340 and features 342. The distance may also be a scalar. The scalar distance may be determined based on a Euclidean distance between features 340 and features 342. The input may be based on both distances or additional distances (e.g., a correlation or covariance matrix). For instance, the input may be a concatenation of multiple distances flattened for input into network 360. In step 412 an abnormality of the tissue 214 may be determined based on the input and network 360.

In step 414, a treatment may be applied or adjusted to a patient. The treatment may be surgery, chemotherapy, hormonal therapy, immunotherapy, or radiation therapy, or a combination of surgery, chemotherapy, hormonal therapy, immunotherapy, radiation therapy. The treatment may be applied or adjusted based on the abnormality.

Figure 5:
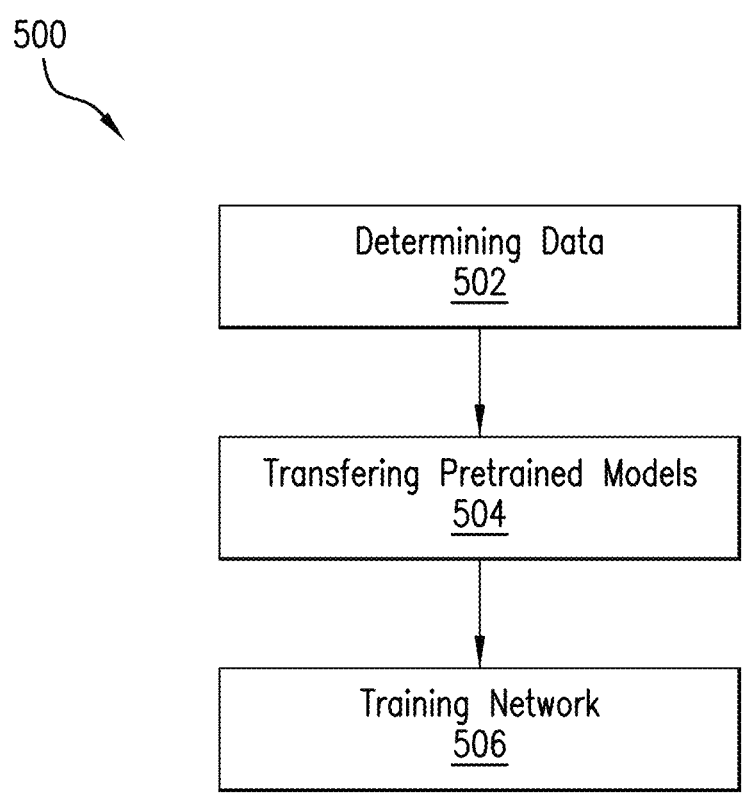
FIG. 5 illustrates a method for training one or more networks.

Referring to FIG. 5, a method 500 for training one or more networks in accordance with one or more implementations of the present disclosure is shown. For example, the training data may comprise curated data from one or more studies. In step 502, the test and training data may be determined. In an example, the training data may comprise only curated data or only a portion of the curated data. For example, the training data may include thousands of images from FFDM exams. For each patient, images may be collected from previous year and current year FFDM exams. The images may be labeled for classifying abnormal and normal tissue. For training networks each image may be paired with its corresponding previous year image and each image with its corresponding previous year image (left/right breast, CC/MLO view). To reduce the unnecessary computational cost, the black background may be removed from the original FFDM images as much as possible. An algorithm may be used to detect the widest breast from the data set and set the cutting margin as 20 pixels away from the widest breast skin edge. In addition, all annotations and metal marks may be removed from all the FFDM images. To increase the size of the training data set, data augmentation may be used. For example, rotation (e.g., 90, 180, and 270 degrees) and Contrast Limited Adaptive Histogram Equalization (CLAHE). In step 504, the networks 350, 370 may be pretrained ResNet networks with pretrained weights to initialize the backbone networks for all the networks. Weights for other networks (e.g., network 360) may be randomly assigned or assigned with a normal distribution (e.g., Xavier). The pretrained weights may be unfrozen during the training process of step 506. As such, the weights of networks 350, 370 may be adjusted slightly and differ from one another. Dropout may be used to prevent overfitting. In addition, an LI regularizer (e.g., 1e.5 to 2) and L2 regularizer (e.g., 1e.4 to 2) may be used in fully-connected layers. Networks trained and implemented in such a new and different way are beyond what is achievable by pen and paper or prior techniques, removing or reducing the time-consuming and laborious—and quite often inaccurate—behavior of manual analysis. Further, techniques described herein are not those previously used in a manual process. These specific techniques, as described herein, for training and application of networks are an improvement in technology or technical field that at least includes one or more of artificial intelligence, radiography or other imaging techniques, and oncology. As shown in FIG. 7, the techniques described herein at least improve the treatment of disease by ensuring the proper level of treatment is administered.

Further, the techniques described herein do not pre-empt every method of improving treatment or monopolize the basic tools of scientific or technological work.

In FIG. 6, an example network architecture 600 in accordance with one or more implementations of the present disclosure is shown. The example network architecture may be used in networks 350, 370, for example. The network architecture contains five building blocks 610, 620, 630, 640, 650 with respective layers followed with an average pooling layer 660. The size of the layers, kernels, and hyper parameters are for example only. In the first building block 610, there is a 7×7 convolutional layer with a batch normalization layer and the ReLU activation layer. Max pooling is also applied after the first building block. The other building blocks 620, 630, 640, 650 contain convolutional blocks and identity blocks. Each convolutional block and identity block may have three convolutional layers, three batch normalization layers and three activation layers. The kernel size may be 1×1, 3×3, or otherwise. The purpose of convolutional blocks is to reduce feature dimensions, therefore, a 1×1 convolutional layer and batch normalization layer is added to the short cut path of the convolutional blocks 610, 620, 630, 640, 650. To adjust for two classes (single neuron output), the top layers of ResNet are removed and two fully connected layers are added, with dimensions of 512, and 256 with an output layer. A ReLU activation function for the fully connected layers (e.g., 362). The output may be a single neuron, and a sigmoid function 364 may be applied to obtain the likelihood of abnormal and normal.

In FIG. 7, example results 700 are shown in accordance with one or more implementations of the present disclosure. The results 700 indicate the performance of one or more techniques described herein indicated as FFS-CNN 704. The results 700 also include other techniques 702 and the lower performance associated with such techniques. For example, one or more of the techniques described herein resulted in higher sensitivity and specificity in determining abnormal tissues than before, which may provide for improved treatments of abnormal tissues. Further, the accuracy and precision are also improved through one or more of the techniques described herein, as indicated.

Next, further detail for identifying abnormalities is presented. In light of empirical effectiveness of conjoined networks and the reality of mammogram data scarcity, conjoined network-based models are disclosed to classify mammograms, which are referenced from the reading procedure of radiologists. More specifically, a model is disclosed based on the conjoined network methodology that compares high-resolution previous (history) mammogram exams with current mammogram exams to increase the accuracy of breast cancer detection, and to be able to detect very small and nonmass abnormalities. Disclosed is an end-to-end model based on the conjoined CNN model that uses previous year and current year images as paired inputs to predict the probability of malignancy and disclosing a new distance learning function for more effective comparison between the current year and previous year mammogram images.

The performance of the model was evaluated using accuracy, sensitivity, precision, specificity, F1 score, and receiver operating characteristic (ROC) area under the curve (AUC) metrics. Moreover, the performance of the model in detecting nonmass and small tumors was examined. The performance of the model was compared with those of some baseline models that use current images only (ResNet and VGG) and also use current and prior images (LSTM and vanilla Siamese).

Methods

Feature fusion Siamese classifier-Traditional CNN models for FFDM classification only consider the intra-image (within image) features from each individual image. Few models have been proposed to learn both interimage (between images) and intraimage features from both Craniocaudal (CC) and (mediolateral oblique) MLO views of a patient's particular breast. As disclosed, an end-to-end model was constructed based on the conjoined network model to extract intraimage and interimage features from pairs of previous and current year FFDMs of patients for more accurate breast cancer classification. In the following, two variants of the model are explained to fuse intraimage features: distance learning network and concatenation network.

Figure 8A:
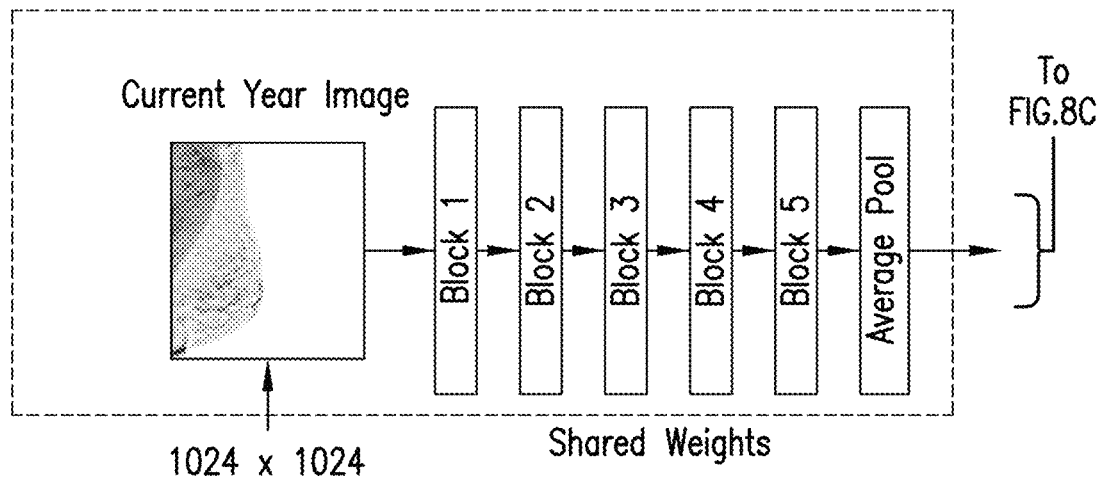
FIGS. 8A-8C, collectively referred to as FIG. 8, depict aspects of feature extraction from current and previous images using parallel networks.
Figure 8B:
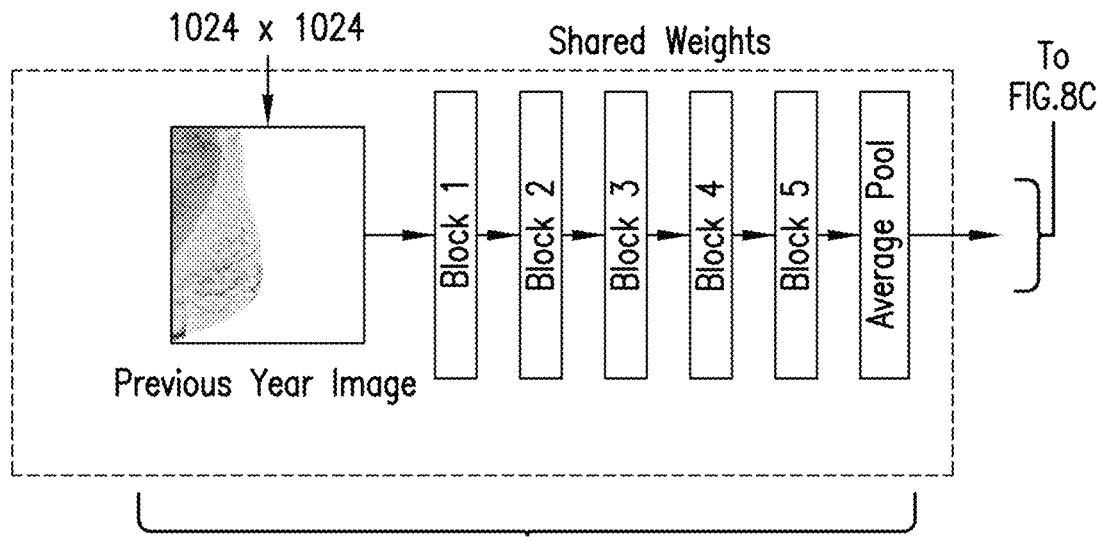
Figure 8C:
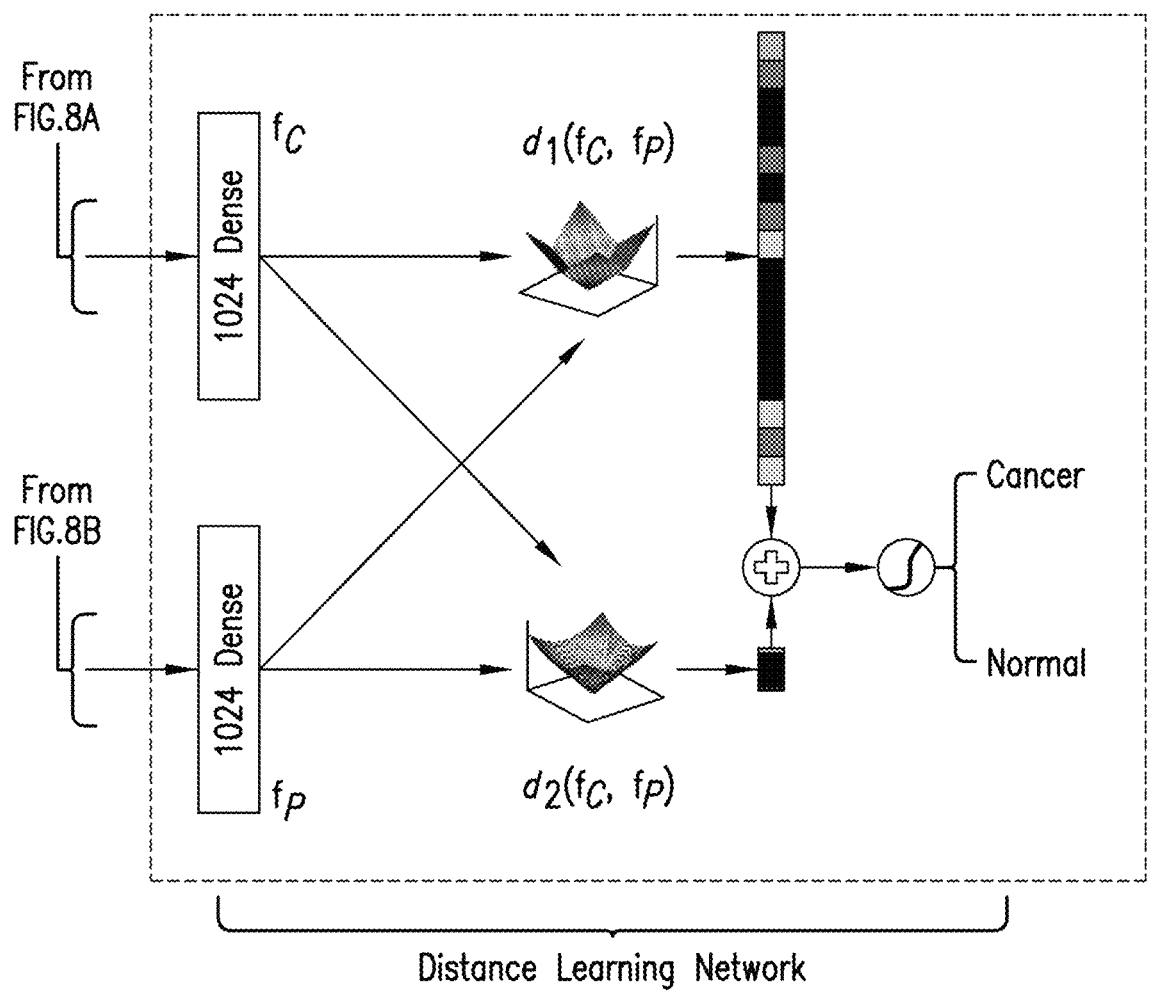

Feature fusion conjoined CNN (FFS-CNN) with distance learning network—The model includes two identical parallel CNNs (twin CNNs) with shared weights as twin networks followed by a distance learning network to predict whether or not the input pair mammograms are similar or dissimilar. Pretrained ResNet was used as the backbone for the parallel networks, as can be seen in FIG. 8. The detail information about the ResNet model is given below and shown in Table 1. Each of the parallel networks extracts internal-level features from its input image. The distance learning network measures the distance between the feature maps from the twin networks and employs a fully connected (FC) network to learn the differences between the feature maps (interimage features). The disclosed model is called FFS-CNN. FIGS. 8A and 8B illustrate a structure of the FFS-CNN. The structure employs two parallel CNNs with shared weights for domain-specific feature representation learning. The shared weights networks employ ResNet as backbone. FIG. 8C illustrates the feature representation $f_C$ and $f_P$ from a pair of a current year image and a previous year image that will feed to d1(•) and d2(•) functions to build the distance features for the distance learning network. The plus-circle sign denotes concatenation of distance feature vectors. The output of the distance learning is the similarity probability where "similar" denotes normal and "dissimilar" denotes cancer.

TABLE 1

Backbone network configuration

| Building block | Layer | Input dimension | Output dimension |
|---|---|---|---|
| Block 1 | conv 7 × 7 @ 64 | 1024 × 1024 | 512 × 512 × 64 |
| Block 2 | conv 1 × 1 @ 64 | 256 × 256 × 64 | 256 × 256 × 64 |
|  | conv 3 × 3 @ 64 | 256 × 256 × 64 | 256 × 256 × 64 |
|  | conv 1 × 1 @ 256 | 256 × 256 × 64 | 256 × 256 × 256 |
| Block 3 | conv 1 × 1 @ 128 | 256 × 256 × 256 | 128 × 128 × 128 |
|  | conv 3 × 3 @ 128 | 128 × 128 × 128 | 128 × 128 × 128 |
|  | conv 1 × 1 @ 512 | 128 × 128 × 128 | 128 × 128 × 512 |
| Block 4 | conv 1 × 1 @ 256 | 128 × 128 × 512 | 64 × 64 × 256 |
|  | conv 3 × 3 @ 256 | 64 × 64 × 256 | 64 × 64 × 256 |
|  | conv 1 × 1 @ 1024 | 64 × 64 × 256 | 64 × 64 × 1024 |
| Block 5 | conv 1 × 1 @ 512 | 64 × 64 × 1024 | 32 × 32 × 512 |
| Last layer | conv 3 × 3 @ 512 | 32 × 32 × 512 | 32 × 32 × 512 |
|  | conv 1 × 1 @ 2048 | 32 × 32 × 512 | 32 × 32 × 2048 |
|  | Average pooling | 32 × 32 × 2048 | 8 × 8 × 2048 |

Pairs of current and previous mammogram images are inputs of the model, FFS-CNN.

The goal of the model is to predict the similarity between a current year image, denoted by C, and its corresponding previous year image, denoted by P, where "similar" means normal and "dissimilar" means cancer. Define S={$(C_1, P_1, y_1), \ldots, (C_N, P_N, y_N)$} to present the training data set, where $y_i$ represents the class label. For pair of images $C_i$ and $P_i$, the binary label $y_i$ is assigned to 1, indicating cancer when $C_i$ is a cancer image and $P_i$ is a normal image. Otherwise, the binary label $y_i$ is assigned to 0, indicating normal, when both $C_i$ and $P_i$ are normal images.

The twin CNNs generate feature representation denoting the flattened feature maps (feature vectors) of a pair of current year and previous year images. These feature vectors are input to the distance learning functions given in Equations (6) and (7), where $d_1$ measures the pixel-wise distance of $f_C$ and $f_P$, $d_2$ measures the Euclidean distance between $f_C$ and $f_P$, and m is the size of the feature vectors.

$$d_1 = f_C - f_P, \qquad (6)$$

$$d_2 = \sqrt{\sum_{j=0}^{m}(f_C^j - f_P^j)^2}. \qquad (7)$$

Vector d1 is concatenated with scalar $d_2$ to build the distance feature for classification. This distance feature inputs to the distance learning FC layer that is the output layer. Finally, at the output layer a sigmoid function, as given in Equation (8), is applied to the distance feature to predict the probability of dissimilarity (cancer) or similarity (normal).

$$\hat{y} = \text{sigmoid}(w^T[d_1 ++ d_2] + b), \qquad (8)$$

where w denotes the vector of weights, b denotes bias, + denotes concatenation, and ŷ represents the predicted probability of similarity. In the disclosed model, the similarity probability represents the likelihood of abnormal changes between current year and previous year images.

The loss function is a linear combination of three terms as $$L = \lambda_1 L_{entropy} + \lambda_2 L_{norm2} + \lambda_3 L_{norm1}, \qquad (9)$$

where λ1, λ2, and λ3 are parameters for L, $L_{entropy}$ is the cross-entropy loss for classification as given in Equation (10).

$$L_{entropy} = -(y \log(\hat{y}) + (1-y) \log(1-\hat{y})), \qquad (10)$$

where y is the true label for the sample.

$L_{norm1}$ is the L1 norm, and $L_{norm2}$ is the squared L2 norm of the vector representation of the FC layer parameters, w, and are defined as $$L_{norm1} = \sum_{w_i \in w} |w_i|, \qquad (11)$$

$$L_{norm2} = \sum_{w_i \in w} |w_i^2|, \qquad (12)$$

$L_{norm1}$ and $L_{norm2}$ are used as regularizer to penalize the number of parameters to avoid overfitting. Training and optimization of the model are described further below.

FFS-CNN with feature concatenation (FFS-CNN-FC)—In order to examine the effectiveness of the distance learning function used in FFS-CNN, a variant of the FFS-CNN model was developed that does not include the distance learning function. Same as FFS-CNN, the model contains two sub-networks (parallel CNNs), using ResNet as the backbone to extract abstract intraimage features from pairs of input images. However, instead of using distance learning functions, the extracted previous year and current year features ($f_c$ and $f_p$) are concatenated and are followed by a dense layer (without using any distance function) to learn the feature-level differences. This model is called FFS-CNN-FC (shown in FIG. 9E). The loss function used for this model is defined in Equation (9).

Baseline Models

Figure 9A:
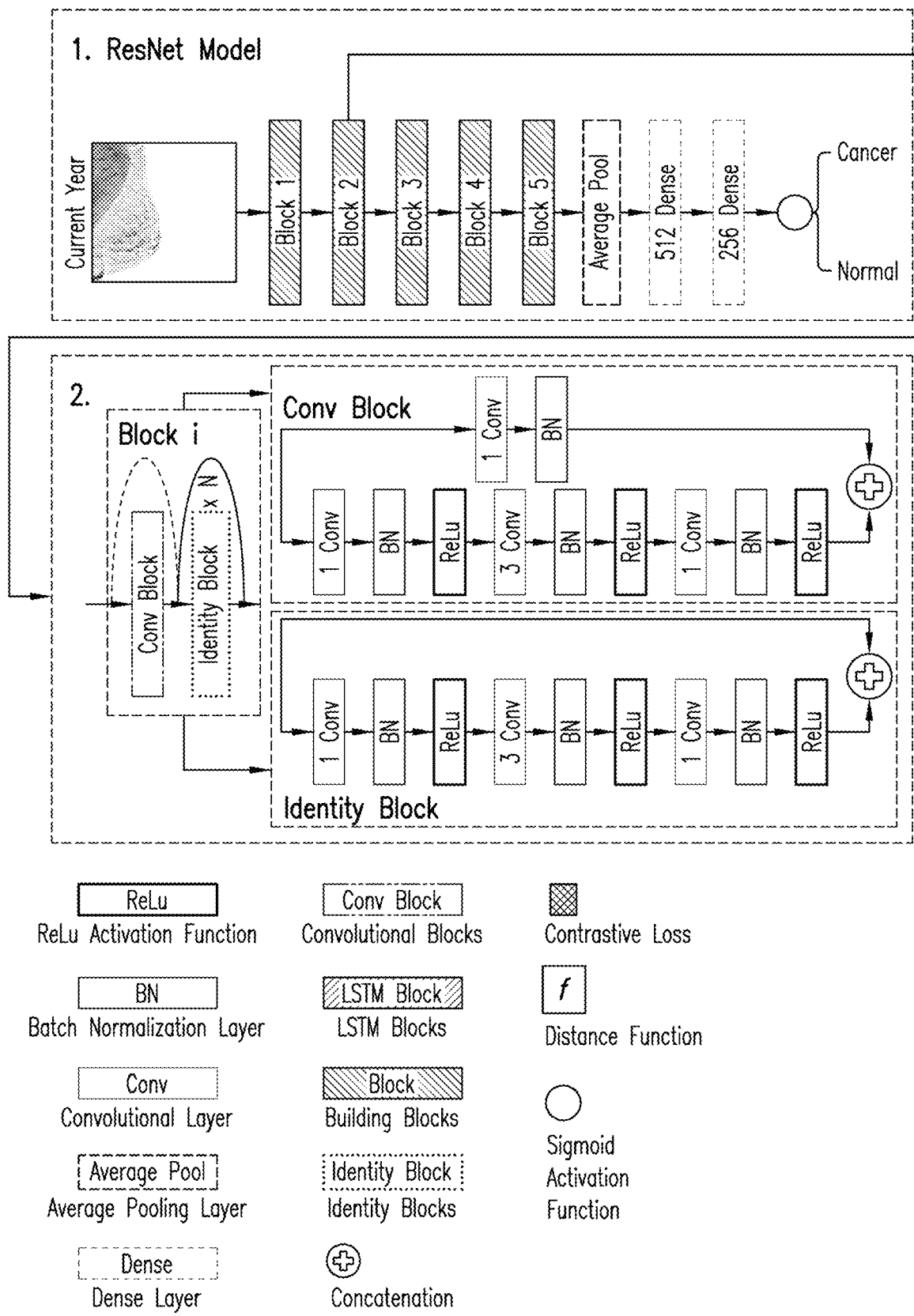
Figure 9B:
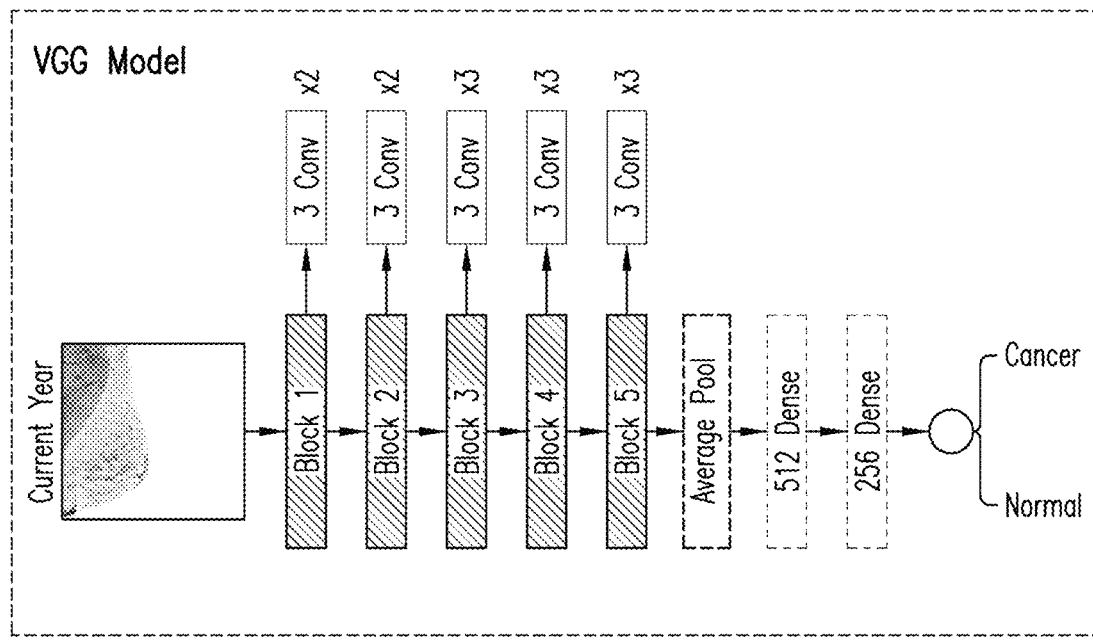
Figure 9C:
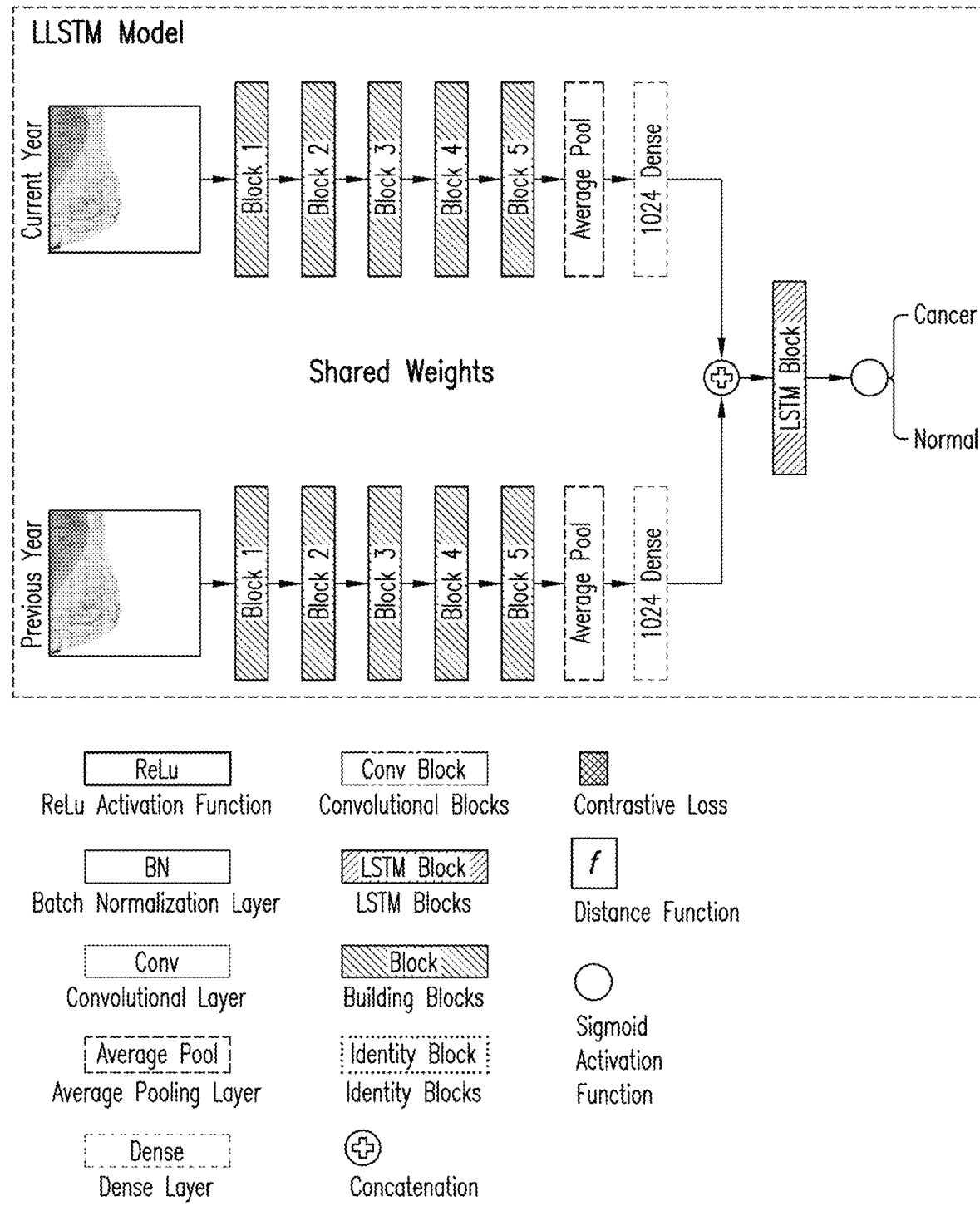
Figure 9D:
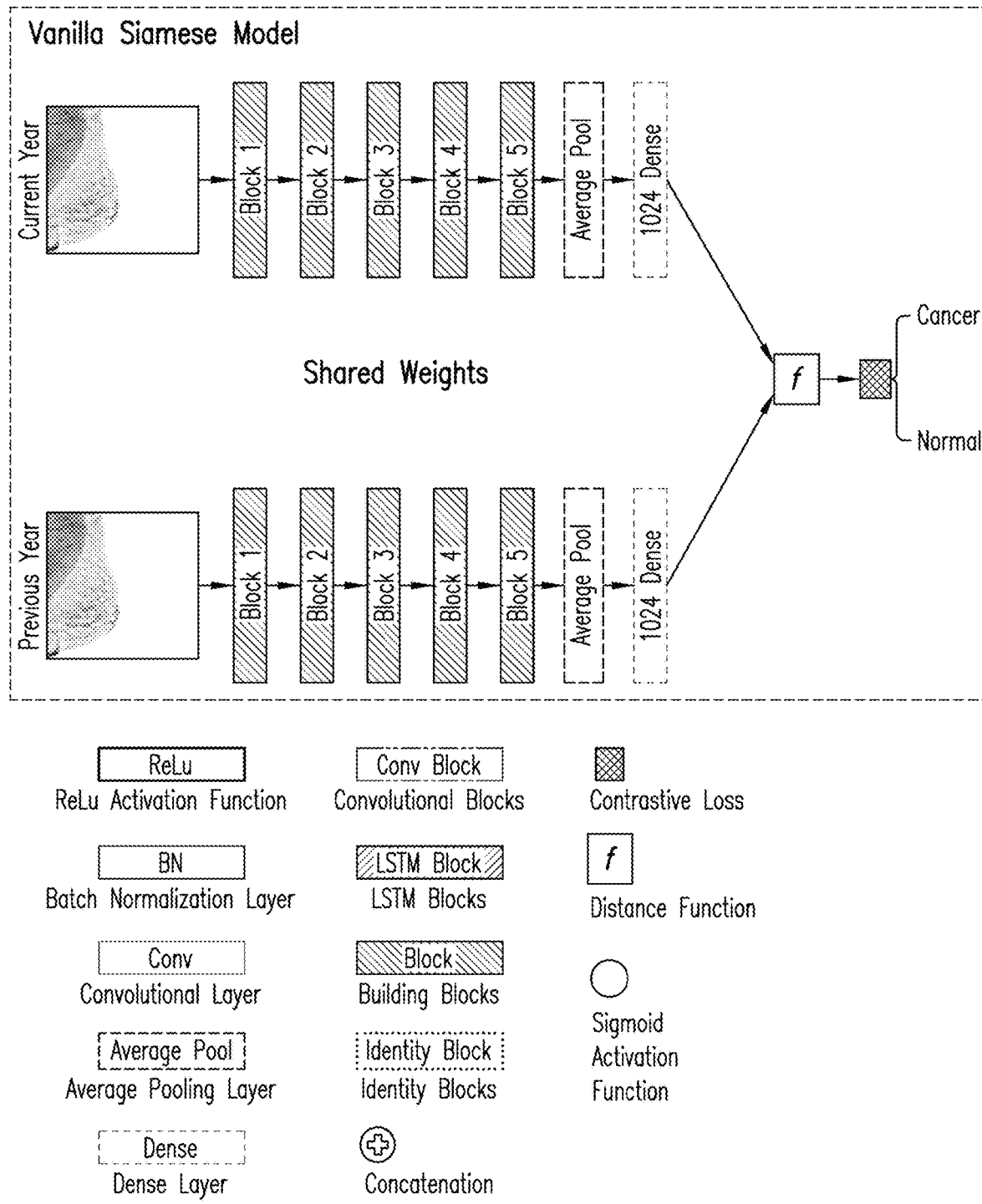
Figure 9E:
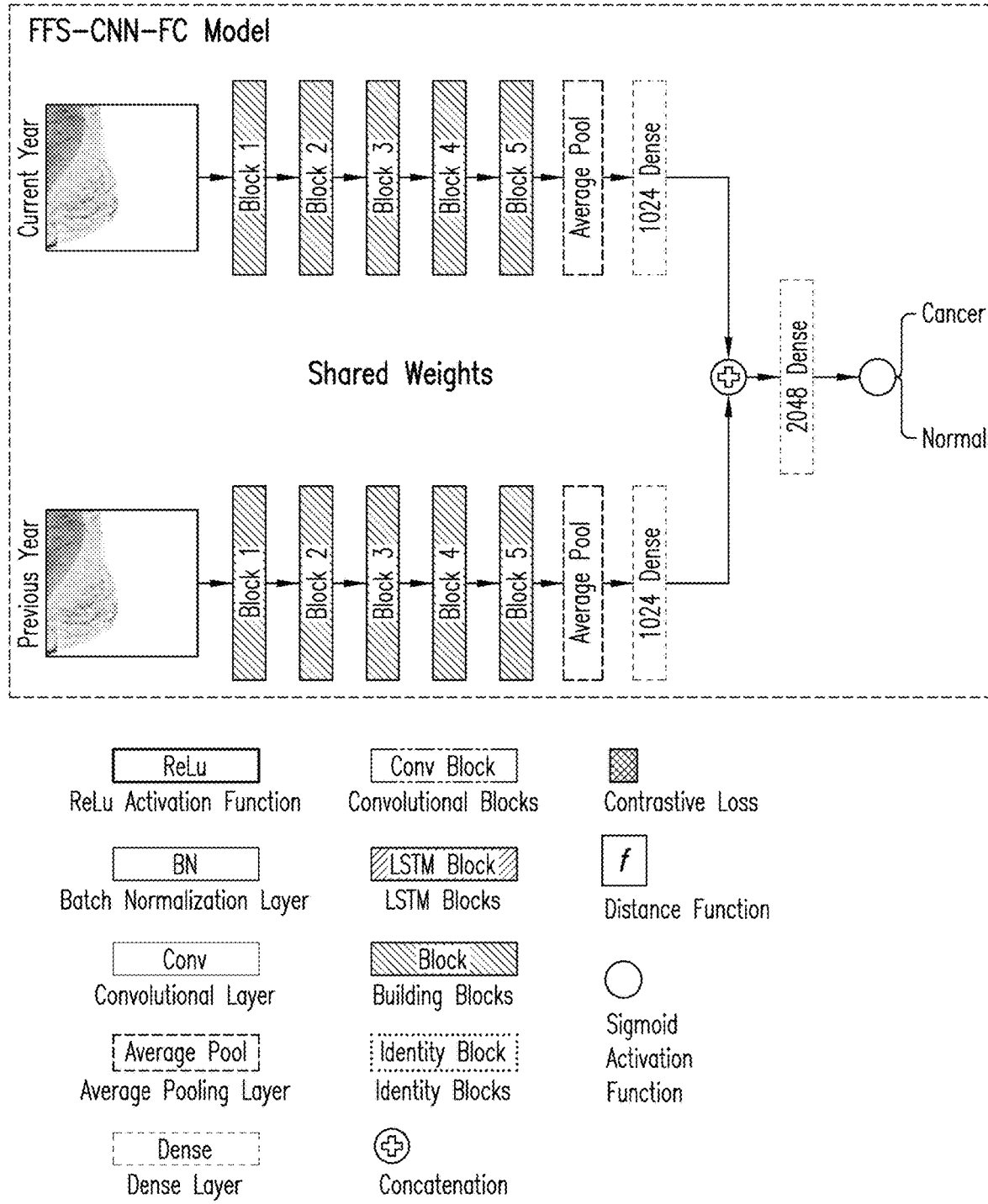

To evaluate the performance of the disclosed models, FFS-CNN and FFS-CNN-FC, the performance of those models is compared with those of multiple baseline models including feature fusion models such as a vanilla Siamese network, a longitudinal LSTM model (LLSTM) and well-known deep learning models such as VGG and ResNet. Schematic diagrams of all the models are shown in FIG. 9. To have a fair comparison, the feature fusion baseline models and the disclosed FFS-CNN and FFS-CNN-FC models use the same backbone network architecture and all the models use the same input size of 1024×1024. ResNet was used as the backbone for all the feature fusion models in this evaluation. The architecture of the backbone ResNet is shown in FIG. 9A. The model configuration parameters for all the baseline models are also summarized in Table 4. The baseline models are described below. FIGS. 9A-9C illustrate schematic diagrams of the baseline models. FIG. 9A illustrates an overall view of the ResNet50 model and a structure of the ResNet model building blocks i for blocks 2 to 5 where each block is a grouping of layers. Each block includes a convolutional block and identity block, where convolutional and identity block contains three convolutional layers (kernel size: 1×1, 3×3, and 1×1) with batch normalization layer and ReLu activation function. Convolutional blocks also include a 1×1 convolutional layer and batch normalization layer at the short cut path. Block 2 to block 5 have 2, 3, 5, and 2 identity blocks (denoted by xN), respectively. FIG. 9B illustrates a VGG model. The first and second building blocks contain two convolutional layers and the third to fifth building blocks contain three convolutional layers (kernel size: 3×3). FIG. 9C illustrates a longitudinal LSTM model. FIG. 9D illustrates a Vanilla Siamese model. FIG. 9E illustrates an FFS-CNN-FC model. FIG. 9F illustrates an FFS-CNN model. The detailed structure of the FFS-CNN model is illustrated in FIG. 8.

TABLE 4

| | Model configuration | | | | | |
|---|---|---|---|---|---|---|
| | ResNet | VGG | LLSTM | Vanilla Siamese | FFS-CNN-FC | FFS-CNN |
| Dropout | 0.2 | 0.2 | 0.2 | 0.2 | 0.2 | 0.2 |
| DWI[a] | Xavier | Xavier | Xavier | Xavier | Xavier | Xavier |
| Optimizer | Adam | Adam | Adam | Adam | Adam | Adam |
| LR[b] | 1e–2 to 1e–5 | 1e–2 to 1e–5 | 1e–2 to 1e–5 | 1e–2 to 1e–5 | 1e–2 to 1e–5 | 1e–2 to 1e–5 |
| Cosine LR[b] | ✓ | ✓ | ✓ | ✓ | ✓ | ✓ |
| Batch size | 16 | 16 | 4 | 4 | 4 | 4 |
| Parameters | 90, 828, 673 | 283, 282, 2418 | 42, 973, 313 | 157, 806, 466 | 157, 808, 513 | 157, 807, 490 |
| Pretrained | ✓ | ✓ | ✓ | ✓ | ✓ | ✓ |
| NL[c] | 53 | 16 | 54 | 52 | 52 | 51 |
| Input size | 1024 × 1024 | 1024 × 1024 | 1024 × 1024 | 1024 × 1024 | 1024 × 1024 | 1024 × 1024 |

[a]Dense layer weight initialization.
[b]Learning rate.
[c]Number of layers.

ResNet—The overall structure of the ResNet model is shown in FIG. 9A. The original structure of ResNet50 was used. The ResNet50 model contains five building blocks followed by an average pooling layer. In the first building block, there is a 7×7 convolutional layer with a batch normalization layer and the ReLu activation layer. Max pooling is also applied after the first building block. The other building blocks contain convolutional blocks and identity blocks. Each convolutional block and identity block has three convolutional layers (kernel size are: 1×1, 3×3, and 1×1), three batch normalization layers and three activation layers. In convolutional blocks, a 1×1 convolutional layer and batch normalization layer are added to the short cut path of the convolutional blocks (the overall structure of the convolutional block and identity block are shown in the middle section of FIG. 9A.). To adjust the original ResNet50 network for the data set that has two classes (single neuron output), the top layers of the original ResNet were removed and two FC layers were added, with dimensions of 512 and 256 with an output layer. ReLu activation function was used for the FC layers. The output is a single neuron and sigmoid function was applied to obtain the likelihood of cancer and normal. The binary cross-entropy loss function was used, given in Equation (9), to train this model.

VGG—The VGG model was used as a baseline model. The structure of the VGG model is demonstrated in FIG. 9B. The model contains five building blocks. The first and second building blocks contain two convolutional layers with pooling layers. The third to fifth building blocks contain three convolutional layers with pooling layers. The kernel size of all the convolutional layers is 3×3. The ReLu activation function is applied to all the convolutional layers. The last three FC layers are modified to accommodate the data set. The last FC layers are switched to 512 and 256 dense layers. The overall loss, including the binary cross-entropy loss function, given in Equation (9), was used to train this model.

Longitudinal LSTM network—The performance of the disclosed models was compared with a LSTM-based model, which uses current year and prior year mammogram images to detect cancer. The overall model includes the twin CNNs used in the disclosed models which use ResNet as the backbone, and an LSTM block to learn the feature changes from current year and previous year images. This LSTM-based model uses the extracted features from current year and previous year images as longitudinal features and employs the LSTM layers to classify the longitudinal features. As shown in FIG. 9C, the LSTM layers are applied to the concatenation of previous year and current year features extracted from the twin CNNs for classification. The LSTM block contains three layers (one 256 LSTM layer, one 128 LSTM layer, and one 64 LSTM layer). The overall loss, including binary cross-entropy, given in Equation (9), was used as the loss function in this model.

Vanilla Siamese network—The vanilla Siamese network was used as a baseline model to compare its performance with the performance of the disclosed models. The structure of the parallel CNNs is the same as the structure of the parallel CNNs in the disclosed model. As shown in FIG. 9D, the intraimage breast features of a current year image and a previous year image are extracted from the shared weights twin networks. To learn the interimage breast tissue feature changes using the intraimage breast features, the vanilla Siamese model employs the Euclidean distance function given in Equation (7). To predict the feature-level similarity of a pair of previous year and current year images, the contrastive loss function given in Equation (13) was used for this model.

$$L = (1-y) * \frac{1}{2}(d_2)^2 + (y) * \frac{1}{2}\{\max(0, n-d_2)\}^2, \quad (13)$$

where $\gamma$ is the ground truth label, $d_2$ is the Euclidean distance given in Equation (2), and n is a hyperparameter, set to 1 in the experiments.

Data Sets

Figure 10A:
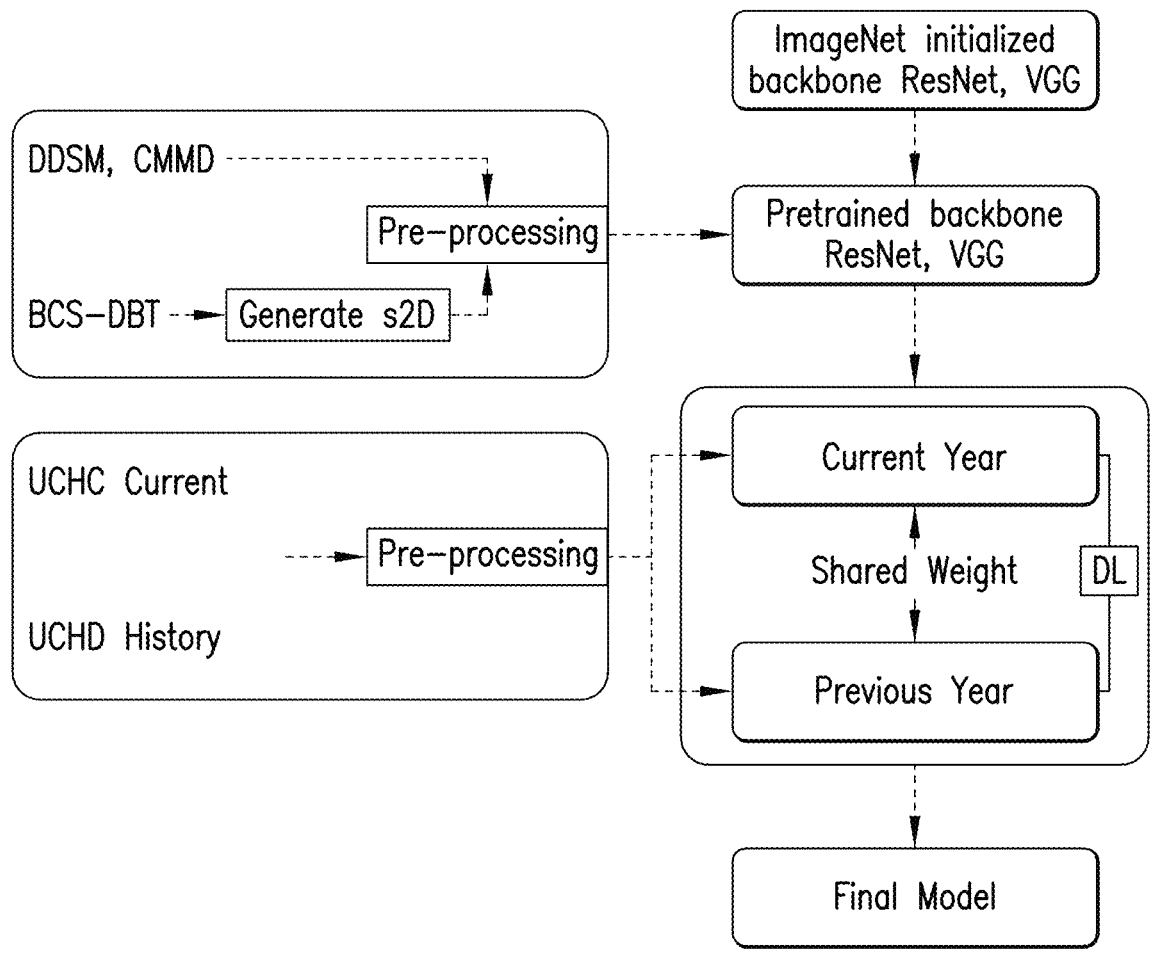
FIGS. 10A and 10B, collectively referred to as FIG. 10, depict aspects of training models being evaluated.
Figure 10B:
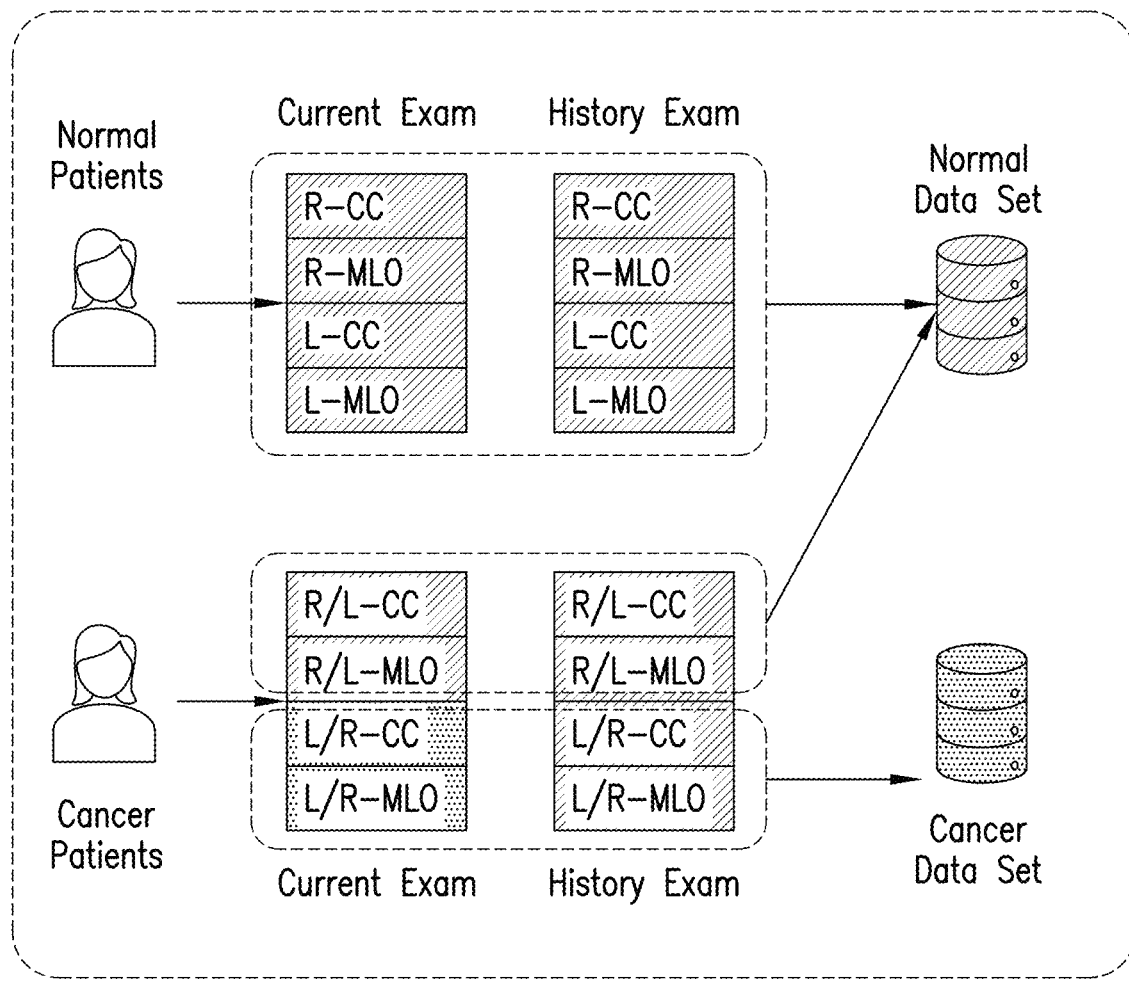

Four data sets were used (three for pretraining and one for training and testing): (1) Digital Database for Screening Mammography (DDSM), (2) the Chinese Mammography Database (CMMD), (3) Breast Cancer Screening-Digital Breast Tomosynthesis (BCS-DBT), and (4) a private data set provided by the Radiology Department at the University of Connecticut Health Center (UCHC). The overall workflow for using the data sets in this evaluation is shown in FIG. 10. FIG. 10 illustrates the workflow for training the model. First with respect to FIG. 10A, the ImageNet pretrained backbone model (ResNet or VGG) is used as an initial model (weights). Next, DDSM, CMMD, and BCS-DBT s2D mammograms are used to pretrain the backbone model. Then, the pretrained model's weights are transferred to the disclosed conjoined network (shared weight twin model). Finally, the pretrained backbone model is fine-tuned using UCHC pairs of current and previous mammograms to generate the final model. Data collection process for UCHC current year mammograms with their corresponding history mammograms as shown in FIG. 10B.

Public data sets—The DDSM, CMMD, and BCS-DBT (Table 2) were used to pretrain the backbone model, and ResNet and VGG baseline models. Note that these data sets do not include history images.

TABLE 2

Data sets information

| Data set | Location | Modality | Resolution | History exam | Normal cases | Cancer cases |
|---|---|---|---|---|---|---|
| DDSM | USA | 2D | 3000 × 4800 | X | — | 2,055 |
| CMMD | China | 2D | 1914 × 2294 | X | — | 2,632 |
| BCS-DBT | USA | 3D | 1890 × 2457 | X | 8528 | 75 |
| UCHC | USA | 2D | 5928 × 4728 to 2294 × 1914 | ✓ | 581 (pairs) | 493 (pairs) |

The DDSM data set contains normal, benign, and cancer cases determined by experts. Since the evaluation focused on classifying cancer and normal cases, benign cases were excluded from DDSM. The average resolution of original DDSM mammogram images is 3000×4800 pixels. 2055 cancer cases were used from this data set. The CMMD data set contains benign cases and cancer cases. Benign cases were excluded from CMMD. The average resolution of original CMMD mammogram images is 1914×2294 pixels. 2632 cancer cases were used from this data set.

The BCS-DBT data set is a public Digital Breast Tomosynthesis (DBT) 3D data set, which contains normal, cancer, benign, and actionable FFDMs (did not result in biopsy but requires further imaging). To increase the number of pretraining images and to have a balanced number of cancer and normal cases for training the backbone models, synthetic 2D mammogram (s2D) was generated using the BCS-DBT 3D mammograms. The combination of Hologic® c-view and reproject 2D mammogram algorithms was employed to generate s2D mammograms. Normal and cancer cases from BCS-DBT were leveraged based on the design of the evaluation. Eight thousand, five hundred, and twenty-eight (8528) normal s2D and 75 cancer s2D were generated from BCS-DBT normal and cancer cases in this evaluation.

UCHC data set—The UCHC data set, including current and history mammograms, was used to train, test, and validate the disclosed and baseline models. The UCHC data set includes collected FFDMs from patients who had mammogram exams at UCHC from 31 Oct. 2006 to 23 Aug. 2021. The FFDMs were acquired on a Hologic® mammography system. The data collection was approved by the UCHC Institutional Review Board. With assistance from the Diagnostic Imaging Informatics Department at UCHC, the DICOMs were exported from Picture Archiving and Communication Systems (PACS) at UCHC. Additionally, patient identifiers were removed and patched with a set naming convention. The mammograms in the data set were annotated by radiologists.

The UCHC data set includes current year and prior year FFDMs of 289 patients (119 mass, 68 AD, 66 MCs, and 36 normal patients), ranging from 28 to 95 years old. The FFDMS of two breasts and two views for each breast (LCC, RCC, LMLO, and RMLO) from a majority of patients are included in the data set (for a few patients not all two breasts and two views FFDMS are available). In this collection (Table 3), 493 mammogram pairs are labeled cancer (493 current cancer FFDMs paired with their corresponding prior normal FFDMs), and 581 mammogram pairs are labeled normal (581 current normal FFDMs paired with their corresponding prior normal FFDMs). The data labeling is shown in FIG. 10b. The majority of patients, 83.4%, had the time between two visits fall within 1-3 years.

TABLE 3

The UCHC data set information

| Patients | For twin models | | | | For Single models | |
|---|---|---|---|---|---|---|
| | Total cancer pairs | | Total normal pairs | | Cancer | Normal |
| 289 | 493 pairs | | 581 pairs | | 493 images | 581 images |
| | P normal | C cancer | P normal | C normal | | |
| | 493 images | 493 images | 581 images | 581 images | | |

Note:
C is current year,
P is previous year

The cancer cases were defined as labeled breast CC views and MLO views with biopsy confirmed cancerous breast lesions. These cases had Breast Imaging Reporting Scores (BI-RADS) of 4 or 5, indicating suspicious abnormality or highly suggestive of malignancy, respectively, and required further confirmation with biopsy. Normal cases were defined as labeled breast CC views and MLO views with no abnormalities found on the breast. These cases had BI-RADS score of 1 or 2, indicating no malignancy and required no further action.

In order to increase the generalizability of the data set, a variety of tumor and breast density types were included. The mass type in the data set contains round, oval, architectural distortion, irregular, and lobulated. The microcalcification type in the data set includes amorphous, coarse, fine linear branching, pleomorphic, punctate, and round with regular. The data set contains all types of breast density including fatty breast, fibroglandular dense breast, heterogeneously dense breast, and extremely dense breast. The fibroglandular dense breast type and heterogeneously dense breast type cover a large portion of the data set.

Figure 11A:
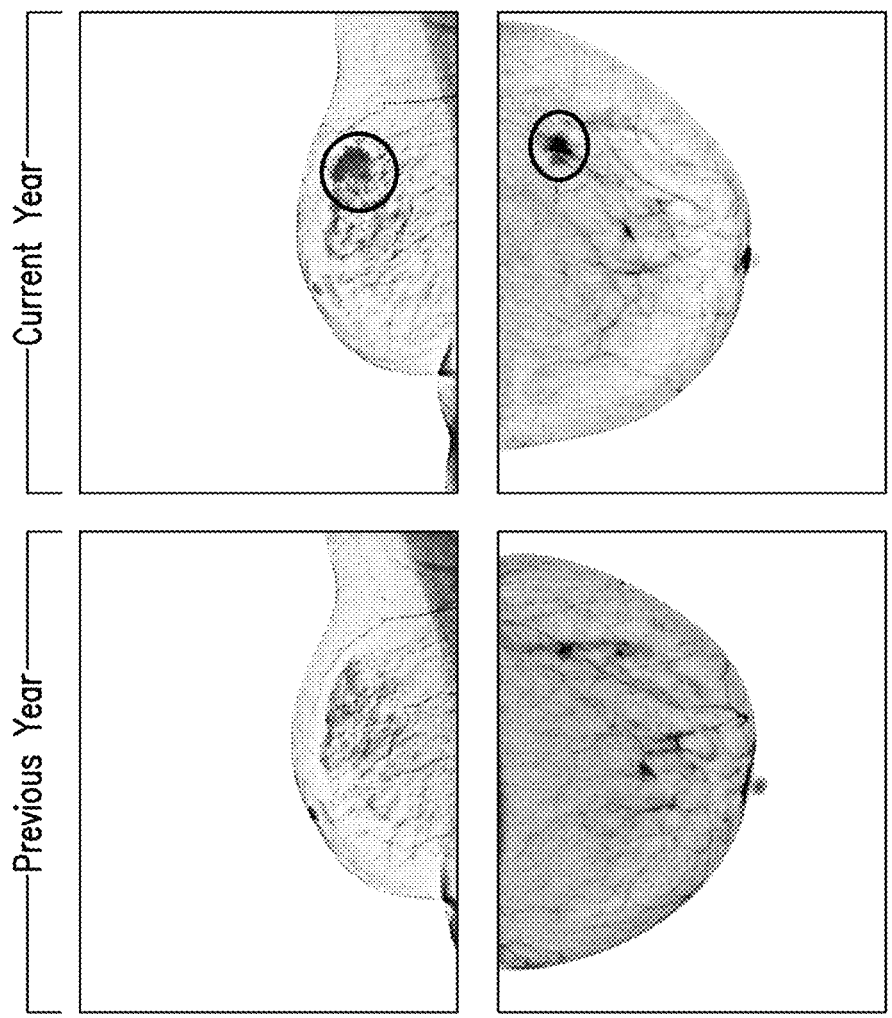
FIGS. 11A and 11B, collectively referred to FIG. 11, depict aspects of examples of current year and previous year mammograms.
Figure 11B:
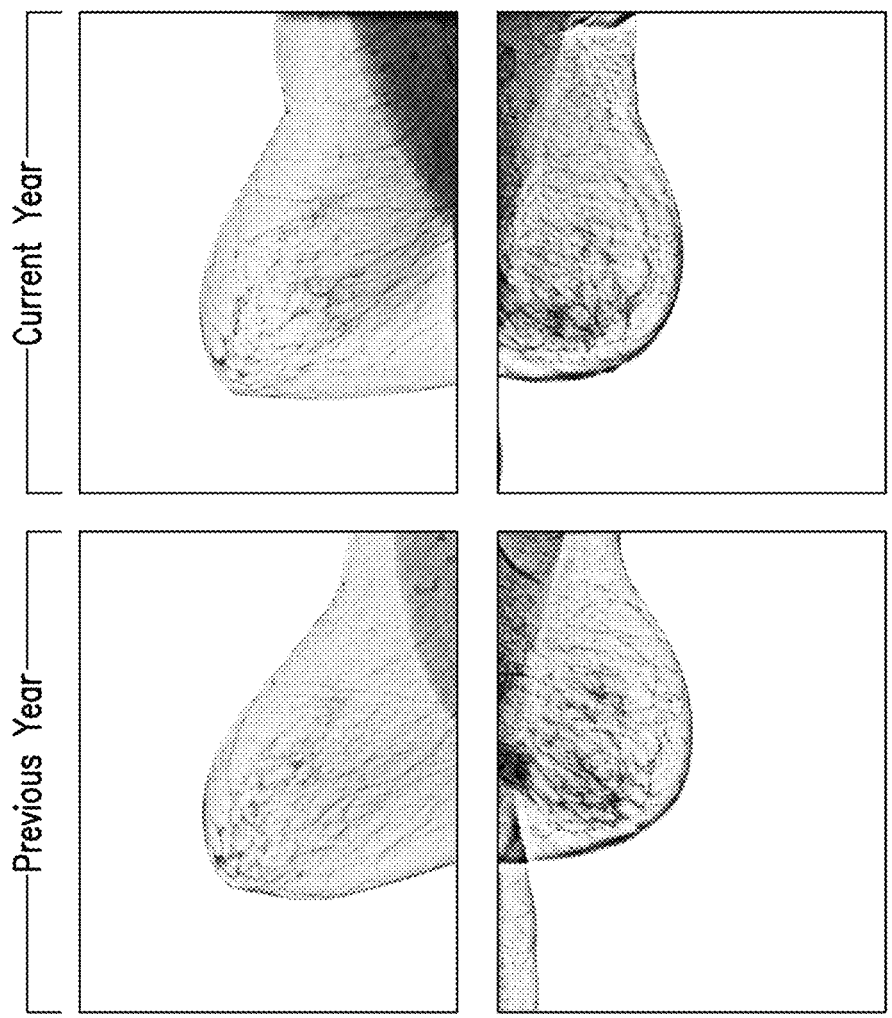

Note that the disclosed model is for classifying cancer and normal images; therefore, the labeled data was used at the image level, not the patient level. Examples of two cancer paired images and two normal paired images are shown in FIGS. 11a and 11b. FIGS. 11a and 11b illustrate examples of pairs of current year and previous year mammogram images. Top row shows current year FFDM images, and bottom row shows previous year FFDM images. FIG. 11A illustrates two examples of cancer pair input. Cancer tumors are indicated by circles on the current year mammograms. FIG. 11B illustrates two examples of normal pair input.

Preprocessing and augmentation-DDSM, CMMD, and s2D BCS-DBT mammogram images were mixed to build a training data set for pretraining the backbone model. Data normalization was also applied to all the images in the data set as $I_{normalized} = (I-Min) (Max-Min)$, where/is a matrix representing an image, $I_{normalized}$ is a matrix representing the image after normalization, Min and Max are the minimum and maximum pixel values, respectively, over all the images in the set.

In the data preprocessing step for the UCHC data set, the annotations have been removed when DICOM files were converted to images using a pydicom package. Pydicom is a pure Python package for working with DICOM files such as medical images. The pixel metal marks have been removed manually from the mammograms. In order to reduce the unnecessary computational cost, the black background was cut out from the images after removing annotations and metal marks. By examining all the mammogram images in the UCHC data set (including RCC, RMLO, LCC, and LMLO views), the widest breast length, θ, was computed. All mammograms, $I_s$, $I \in \mathbb{R}^{N \times M}$, where N is height, and M is width, are cropped such that the mammograms after cut, $I_{cuts}S$, have a dimension of $N \times M - \theta + \epsilon$, $I_{cut} \in \mathbb{R}^{N \times M - \theta + \epsilon}$, where $\epsilon$ is a constant for margin (20 was used in this evaluation). Then, the mammograms were resized to 1024×1024 by employing the bilinear interpolation. To increase the size of the training data set, rotation (90°, 180°, and) 270° and CLAHE48 filter for data augmentation was used.

Training and Experimental Setup

Training configuration—To avoid overfitting, transfer learning was employed to train the disclosed and baseline models. For transfer learning, the ResNet backbone networks and the VGG and ResNet baseline models were pretrained, as shown in FIG. 10. In the first step, pretrained ResNet and VGG models were used, trained by the ImageNet data set, as initial models. Next, the initial models were pretrained using the combined training mammogram data set (DDSM, CMMD, and s2D) as explained above to fine-tune the initial models based on mammogram images. The pretrained networks, then, were used as the backbone models in the disclosed and baseline models and were trained using the UCHC data.

Seventy percent (70%) of the UCHC cancer patients (493 pairs of current cancer and prior normal mammograms) and normal patients (581 pairs of current normal and prior normal mammograms) were randomly selected for training the disclosed models and other baseline models with twin networks. The same selected mammograms of current patients (70% of current cancer patients and current normal patients) were used for training the ResNet and the VGG base-line models that do not have a twin network as shown in Table 3.

To optimize the models and the baseline models, different hyperparameters were examined. To train all the models, 25 epochs were used, and the starting learning rate in a range from 1e-2 to 1e-5 was examined. Cosine learning rate scheduler was used for optimizing the learning rate of the model. In evaluations, input images of size 1024×1024 were used. Because of the limited computational resources for high-resolution inputs, end-to-end mini-batch stochastic gradient descent with batch size of 4 was used to optimize all the models with parallel CNNs, and a batch size of 16 for the ResNet and VGG baseline models. The hyperparameters used to optimize the disclosed models and the baseline models are shown in Table 4. A learning curve of training and validation data was used to monitor the performance in terms of overfitting. To prevent overfitting, dropout in the FC layers (tested range from 0.2-0.6) was used. The FC layer weights were initialized with normal distribution (Xavier), and the bias parameter was set to 0. In addition, $L_{norm1}$ regularizer (13 tested in a range from 1e-5 to 2) and $L_{norm2}$ regularizer ($\lambda_2$ tested in a range from 1e-4 to 2) was used in the FC layers. The gradient decent with adaptive momentum (ADAM) optimizer was used to optimize the accuracy of all the models. Tesla® V100 GPUs with 32 GB memory available from NVIDIA® were used to train and test all the models.

Evaluation metrics—The UCHC data set was used to test and evaluate the performance of the disclosed models and compared it with those of the baseline models. The data set was split out to training (70%), validation (10%), and testing (20%) data sets (note that data augmentation is only applied to the training data set after splitting the data and the testing data set is only used for testing the models). The 95% confidence interval (CI) of all evaluation metrics are reported in this study.

Accuracy, specificity, sensitivity, precision, F1 score, and area under the ROC curve (AUC) evaluation metrics were used, where accuracy defines the percentage of correctly classified images; specificity defines percentage of negative (normal) images classified correctly; sensitivity, which is also called recall, defines the proportion of correctly predicted from positive (cancer) classes; precision measures the rate of positive (cancer) images that are correctly classified; F1 measures accuracy, which is the harmonic mean of recall (sensitivity) and precision; and AUC measures the performance of a binary classification using a range of values for thresholds for computing sensitivities and false positive rates (1-Specificity). The equations for these metrics are shown as follows:

$$F1 = TP/[TP + 1/2(FP + FN)] \quad (14)$$

$$Accuracy = [TP + TN]/[TP + FN + TN + FP] \quad (15)$$

$$Sensitivity = TP/(TP + FN) \quad (16)$$

$$Precision = TP/(TP + FP) \quad (17)$$

$$Specificity = TN/(TN + FP) \quad (18)$$

where TP denotes true positive, TN denotes true negative, FP denotes false positive, and FN denotes false negative.

Results

Overall performance—The performance of all the models in terms of accuracy, specificity, sensitivity, precision, F1 score, and AUC are given in Table 5.

TABLE 5

Model performance

| Model | Accuracy [CI 95%] | Sensitivity [CI 95%] | Precision [CI 95%] | Specificity [CI 95%] | F1 [CI 95%] | AUC [CI 95%] |
|---|---|---|---|---|---|---|
| VGG | 0.82 [0.803, 0.837] | 0.79 [0.753, 0.827] | 0.83 [0.818, 0.842] | 0.85 [0.825, 0.875] | 0.81 [0.798, 0.822] | 0.86 [0.828, 0.892] |
| ResNet | 0.86 [0.835, 0.885] | 0.85 [0.838, 0.862] | 0.86 [0.823, 0.897] | 0.86 [0.823, 0.897] | 0.85 [0.825, 0.875] | 0.90 (0.878-0.922) |
| LLSTM | 0.89 [0.880, 0.900] | 0.89 [0.853, 0.927] | 0.88 [0.855, 0.905] | 0.88 [0.843, 0.917] | 0.88 [0.869, 0.891] | 0.93 (0.921-0.939) |
| VS[a] | 0.88 [0.855, 0.905] | 0.86 [0.835, 0.885] | 0.89 [0.865, 0.915] | 0.90 [0.875, 0.925] | 0.87 [0.845, 0.895] | 0.92 (0.900-0.940) |
| FFS-FC | 0.91 [0.908, 0.932] | 0.92 [0.918, 0.942] | 0.90 [0.899, 0.921] | 0.91 [0.899, 0.921] | 0.91 [0.908, 0.932] | 0.94 (0.938-0.962 |
| FFS | 0.92 [0.919, 0.921] | 0.93 [0.927, 0.933] | 0.91 [0.909, 0.911] | 0.91 [0.909, 0.911] | 0.92 [0.919, 0.921] | 0.95 (0.949-0.951) |

Note:
The bold font indicates the highest values; 95% confidence intervals (CIs) are reported in this table.
[a]VS is vanilla Siamese network.

As shown in Table 5, the results show that the disclosed model FFS-CNN outperforms all other baseline models in terms of all the performance metrics. The accuracy of FFS-CNN (0.92) and FFS-CNN-FC (0.91) is higher compared with accuracy of VGG (0.82) and ResNet (0.86). The longitudinal LSTM and vanilla Siamese models showed comparable accuracy (0.89 and 0.88) with each other, but lower than those of the disclosed models.

Figure 12A:
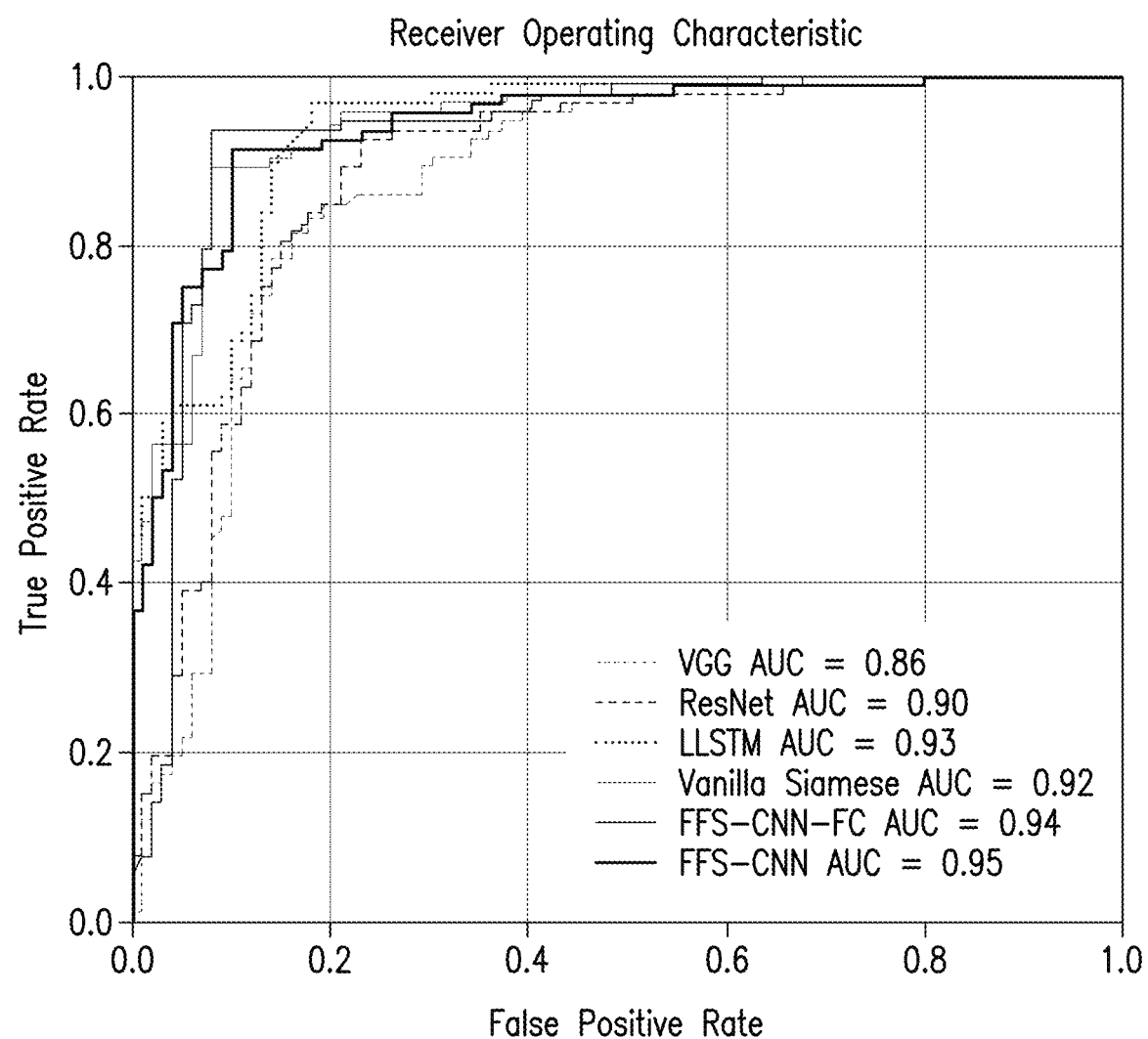
FIGS. 12A and 12B, collectively referred to as FIG. 12, depict aspects of receiver operating characteristic and precision recall curves of disclosed and baseline models.

The ROC for all the models is shown in FIG. 12a, where the average AUC of VGG is 0.86, the average AUC of ResNet is 0.90, the average AUC of the longitudinal LSTM model is 0.93, the average AUC of the vanilla Siamese network is 0.92, the average AUC of FFS-CNN-FC is 0.94, and the average AUC of FFS-CNN is 0.95. To test the significance of the difference between the AUC of the disclosed model, FFS-CNN, with that of the other models, the McNeil and Hanley's test49 was employed. The AUC improvement of FFS-CNN (0.95) is significant compared with VGG (p=0.01), and ResNet (p=0.04), but is not significant compared with longitudinal LSTM (p=0.11), vanilla Siamese (p=0.06), and FFS-CNN-FC (p=0.33). The disclosed model, FFS-CNN, also performs better compared to the other models in terms of specificity and precision with a specificity of 0.91 and a precision of 0.91. This shows that the disclosed model, FFS-CNN, provides considerably less false positive detection. FIG. 12 illustrates AUC and precision recall (PR) plots of the disclosed models and baseline models with FIG. 12A illustrating ROC (receiver operating characteristic) plots and FIG. 12B illustrating PR plots.

In terms of sensitivity, FFS-CNN shows the best performance with average sensitivity of 0.93, which is 0.08 and 0.14 higher than the sensitivity of ResNet and VGG, respectively. The vanilla Siamese and longitudinal LSTM models show the average sensitivity of 0.86 and 0.89, respectively.

As can be seen from Table 5, in terms of all the evaluation metrics, all the models that employ history of images outperform the ResNet and VGG models that use only the current images without considering previous year images. This indicates the importance of employing history of images. The observation that FFS-CNN outperforms all the other feature fusion models, including FFS-CNN-FC, indicates that the distance learning functions can impact the performance of the model.

Figure 12B:
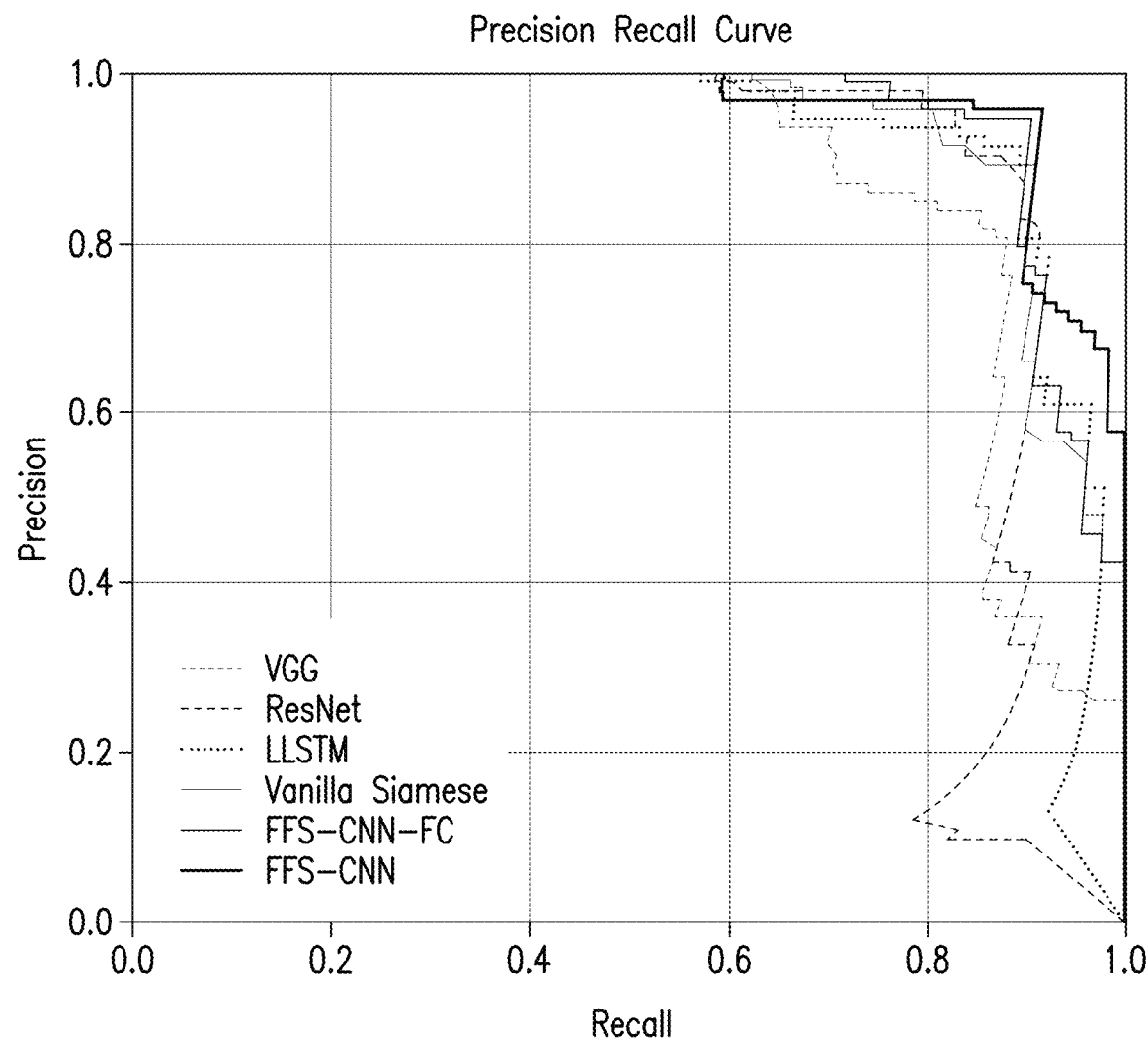

To demonstrate the effectiveness of accurate classification of the FFS-CNN model and compare it with all baseline models, the precision recall curve shown in FIG. 12B was computed. Note that the precision recall curve is computed using each model's best performed result. As can be seen, the FFS-CNN model outperforms the other models and the ResNet and VGG models that do not use history of images cannot compete with the models that use history of images.

Detection of nonmass and small size tumors—The discriminative performance of the disclosed models for nonmass and small size tumors was examined. As shown in Table 6, False Discover Rate (FDR) and False Negative Rate (FNR) in classification were computed where abnormalities are mass, microcalcification, and AD for all the models. The FDRs and FNRs of VGG, ResNet, longitudinal LSTM, and vanilla Siamese in classifying mammograms with masses are comparable and are higher than those of the FFS-CNN-FC and FFS-CNN models. As can be seen in Table 6, all the models have higher error rates in classifying cancer when tumor shapes are nonmasses. However, the FDRs and FNRs of the disclosed models (FFS-CNN-FC and FFS-CNN) are considerably lower compared to the other models. For microcalcification tumors, VGG, ResNet, and longitudinal LSTM perform similarly and the vanilla Siamese network, FFS-CNN-FC, and FFS-CNN perform better in terms of FDR and FNR. For AD cases, FFS-CNN-FC and FFS-CNN outperform all the baseline models in terms of FDR and FNR. Results show that the FFS-CNN-FC and FFS-CNN improve the detection rate of microcalcification and AD-shaped tumors.

TABLE 6

False detection performance for different types of tumors

|  | Mass | | calcs[a] | | AD[b] | |
| --- | --- | --- | --- | --- | --- | --- |
|  | FDR[c] | FNR[d] | FDR | FNR | FDR | FNR |
| VGG | 0.28 | 0.14 | 0.40 | 0.16 | 0.77 | 0.50 |
| ResNet | 0.25 | 0.10 | 0.36 | 0.13 | 0.71 | 0.40 |
| LLSM | 0.22 | 0.10 | 0.32 | 0.10 | 0.65 | 0.30 |
| Vanilla Siamese | 0.21 | 0.14 | 0.29 | 0.06 | 0.67 | 0.40 |
| FFS-CNN-FC | 0.16 | 0.08 | 0.24 | 0.06 | 0.56 | 0.30 |
| FFS-CNN | 0.14 | 0.06 | 0.21 | 0.03 | 0.50 | 0.20 |

Note:
The bold font indicates the lowest values (the lowest error rates).
[a]Microcalcification.
[b]Mass shaped in architecture distortion.
[c]False discovery rate.
[d]False negative rate.

Figure 13:
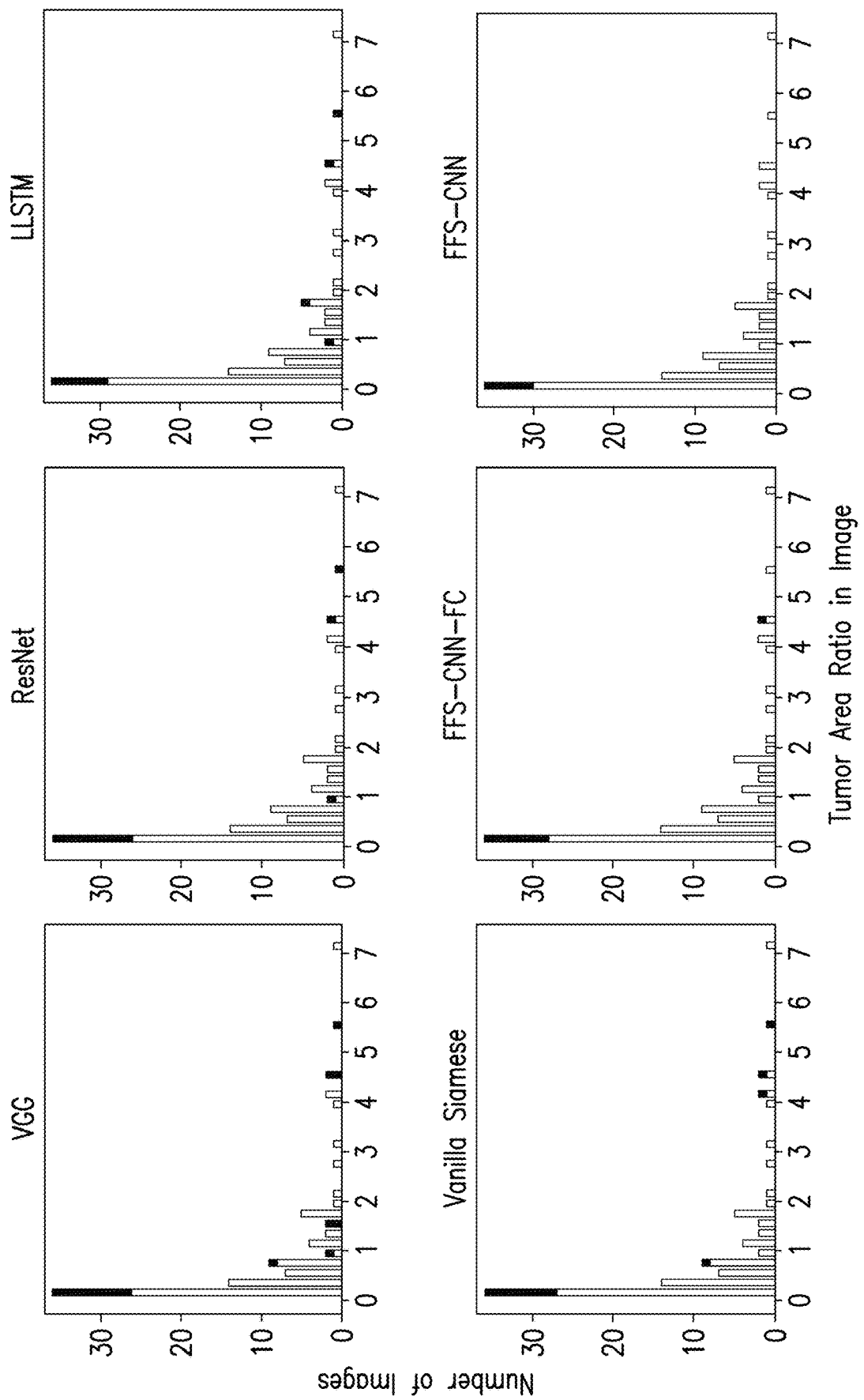
FIG. 13 depicts aspects of cancer prediction of all evaluation models for different size tumors.

To evaluate the performance of the disclosed model in detecting small tumors, the tumor area ratio, r, was computed in mammograms as, $r=(t/I_a) \cdot 100$, where t is the tumor area in pixel and $I_a$ is the image area in pixel. The tumor ratios in mammograms that are accurately classified as cancer (white bars) and tumor ratios of ground truth cancer mammograms (black bars) for all the models are shown in FIG. 13. FIG. 13 illustrates cancer prediction of all the models for different size of tumors (tumor ratios); x-axis is the ratio of tumor area in mammogram images; y-axis is the number of mammogram images. Black bars indicate ground truth and white bars indicate the model prediction.

Results show that all the models, except FFS-CNN, misclassified few mammograms with larger tumors with r>4. All models misclassified some mammograms with small tumors, r<0.5. However, VGG and ResNet missed small tumors more (number of misclassified images >10), and the disclosed models missed small tumors less (number of misclassified images <8). The FFS-CNN-FC and FFS-CNN models show superior performance in classifying mammograms with smaller tumors.

Effect of FC layers—To study the effect of adding more FC layers, the FFS-CNN-FC models were built using two, three, and four FC layers with performance shown in Table 7. Results show that FFS-CNN-FC models perform slightly worse compared to FFS-CNN and adding more FC layers cannot improve the performance.

TABLE 7

FFS-CNN-FC evaluation

| Model | Accuracy | Sensitivity | Precision | Specificity | F1 | AUC |
| --- | --- | --- | --- | --- | --- | --- |
| 2[a] FC layers | 0.91 | 0.89 | 0.92 | 0.93 | 0.91 | 0.94 |
| 3[a] layers | 0.90 | 0.88 | 0.90 | 0.91 | 0.90 | 0.93 |
| 4[a] layers | 0.90 | 0.89 | 0.90 | 0.90 | 0.90 | 0.89 |

[a]Number of layers added after feature concatenation using FFS-CNN-FC.

Analysis

In this analysis, the disclosed model, FFS-CNN, employs the conjoined network methodology, which first extracts intraimage features of current and previous FFDMs and then extracts interimage features for classification. The success of the FFS-CNN model is due to two aspects: (1) using prior mammogram screens as guidance to identify cancer based on not only current breast features, but also prior breast features, and (2) employing a distance learning network to capture cancerous changes in the structure of breast tissues. To enhance the learning ability of the distance learning network, both feature map pixel-wise distances and the Euclidean distance between the extracted features from the current year and previous year images were employed. To examine the effectiveness of the distance learning model, a variant model (FFS-CNN-FC) that concatenates intraimage features and lets FC layers learn the difference between the features was employed, without explicitly imposing any distance metrics to the features. The evaluations demonstrate the superior performance of the disclosed FFS-CNN model over conventional deep learning models and current deep learning models that employ history of images.

Deep learning models such as the ResNet and VGG models have a strong ability to learn FFDM intraimage features. However, as shown in Table 6, the VGG and ResNet models show limited ability to identify AD-shaped tumors. This can be because the ResNet and VGG models are not able to effectively learn the complex characteristics of AD for such a low sample size data set. The generalization performance of conventional deep learning models heavily depends on the size of the training data set. In other words, having an optimal generalizable classification model for FFDMs requires training in many different shapes of tumors. However, collecting all possible tumor shapes to train a model is not practical. Hence, using a small size data set to train those models can increase the risk of overfitting and lead the model to ignore unseen tumor shapes.

Figure 14:
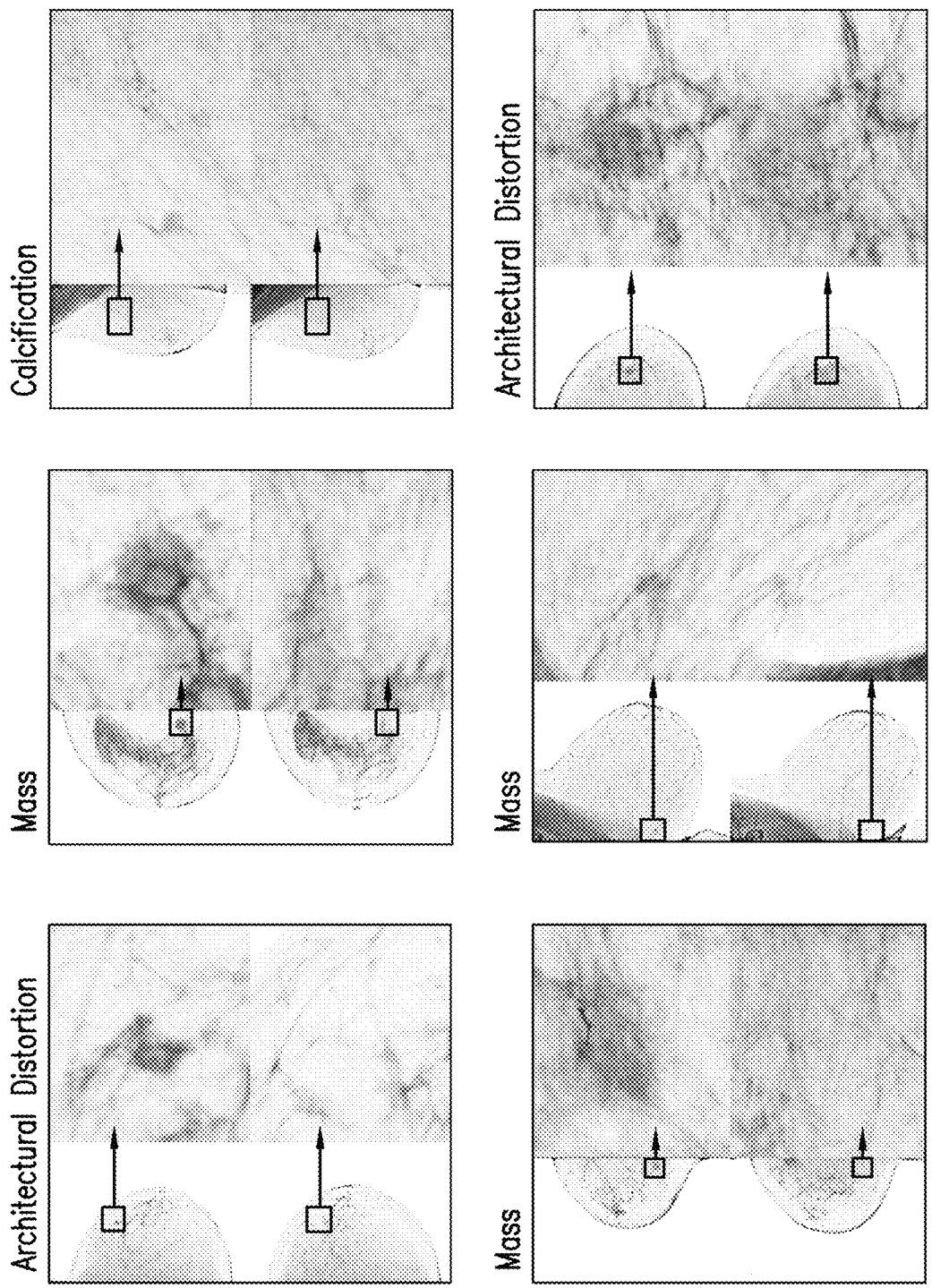
FIG. 14 depicts aspects of cancer case illustrations where cancer is detected by disclosed models but not by the ResNet model.

The one-shot learning characteristic of conjoined-based models can contribute to the superior performance of the disclosed FFS-CNN model in comparison to conventional deep learning models. One-shot learning models aim to learn if a pair of images contain the same object, not to learn objects. As a result, one-shot learning models can be trained and performed well with smaller sample size data sets. As shown in Table 5, the conjoined-based models (FFS-CNN and FFS-CNN-FC) show better results in sensitivity, indicating their strong ability to identify cancer cases, even when trained with smaller data sets. An illustration of tumors identified by the conjoined-based disclosed FFS-CNN model, but missed by ResNet and VGG is illustrated in FIG. 14. As the figure shows, the disclosed conjoined-based FFS-CNN model is able to identify the AD-shaped tumor, which is hard to distinguish from breast tissue, but was not in the prior mammogram. FIG. 14 illustrates a cancer case where cancer is detected by the disclosed FFS-CNN model but not by the ResNet model. In each case, the top row contains a current year image with enlarged abnormal tissue part that is indicated by a white square, and the bottom row contains previous year image with the enlarged tissue part from the same location (i.e., abnormal tissue part of the current year image).

The disclosed FFS-CNN model outperforms the vanilla Siamese model, which also compares current and previous FFDMs. In the vanilla Siamese network, the similarity between previous year features and current year features is learned using the Euclidean distance. The Euclidean distance is the most common distance, which represents the overall dissimilarity and has a better stability property than other distance functions. However, its effectiveness is limited when the feature dimension increases, and the dissimilarity details are important. As shown in FIG. 13, the vanilla Siamese model failed to estimate the dissimilarity of even a few large size tumors. To capture discriminative dissimilarity features of high-resolution complex images, nonlinear combination of differences between pixels of feature vectors can be more effective than overall distance between the feature vectors. Therefore, to have overall and detailed dissimilarity features, the Euclidean distance was concatenated with the pixel-wise distance and applied an FC network as the distance learning network. It is reflected from FIG. 13 that FFS-CNN is able to identify the tumors missed by the vanilla Siamese network.

The LSTM-based model also does not perform as well as the disclosed FFS-CNN model. The LSTM-based model is often beneficial to learn time lagged features in time series data. The learning mechanism of the LSTM-based model is to predict the likelihood of features from current data based on the prior data rather than capturing differences between the data. As a result, its performance in comparing previous and current mammograms is not as good as the disclosed FFS-CNN model, especially for more challenging shapes of tumors. As shown in Table 6, the LSTM-based model has the lowest ability to identify AD tumors compared with the other twin network models.

Next, techniques are presented to identify abnormalities and determine locations of the abnormalities. Specifically, disclosed are: an unsupervised deep learning model that can detect breast cancer without requiring pixel level labeled data and that covers the entire process from start to finish; a Feature Correlation Module (FCM) that can accurately pinpoint feature discrepancies between the current and previous image; an Attention Suppression Gate (ASG) to enhance the capacity of the model in differentiating between normal and cancer cases; and a module-Breast Abnormal Module (BAM)—to predict abnormal maps of the breast, which can help localizing tumors. The unsupervised deep learning model exhibits the unique capability to predict normal mammograms, whereas baseline models are restricted to functioning solely with mammograms containing tumors.

Methods

The disclosed model is called the Unsupervised Feature Correlation Network (UFCN) and it takes advantage of the deep U-shaped residual connected autoencoder reconstruction process to learn the abnormal variation maps. The model method is discussed in detail below.

Definitions-Inputs are defined as $I_i=\{C_i \in R^2, P_i \in R^2\}$, where $C_i$ is a current year image that can be biopsy-confirmed cancer or normal and Pi is a prior image that is normal. Let $f: R^2 \rightarrow R^p$ be a feature extraction function and $g: R^p \rightarrow R^2$ be a feature transpose function. For an $f$ and g, the estimate of $C_i$, $\hat{C_i}$, can be obtained using these functions. On the other hand, if $f$ and g can be learned through training for a given $\hat{C_i}$ then learning $f$ and g can be considered as an image reconstruction problem. If functions $f$ and g have the property of being differentiable, then their parameters can be optimized using gradient descent.

However, the disclosure predicts the abnormal variation map (AVM) by training $f$ and g in an unsupervised manner. Particularly, the disclosed model will be trained to learn $f$ and g under the task of reconstruction and prediction of the AVM using the learned feature difference between $C_i$ and $P_i$. In practice, two sub-problems are solved: training parameters of $f$ and g with given $\hat{C_i}$ and prediction of the optimal AVM with learned $f$ and g. Because it is desired to predict no abnormal changes for normal patients ($C_i$s) where AVM should detect nothing, a mapping function h: $R^p \rightarrow R$ in g is introduced to map the probability of binary labels of $C_i$s, $y_i$s. Here, the $y_i$ represents binary label of either normal or cancer shown in current mammograms.

Figure 15:
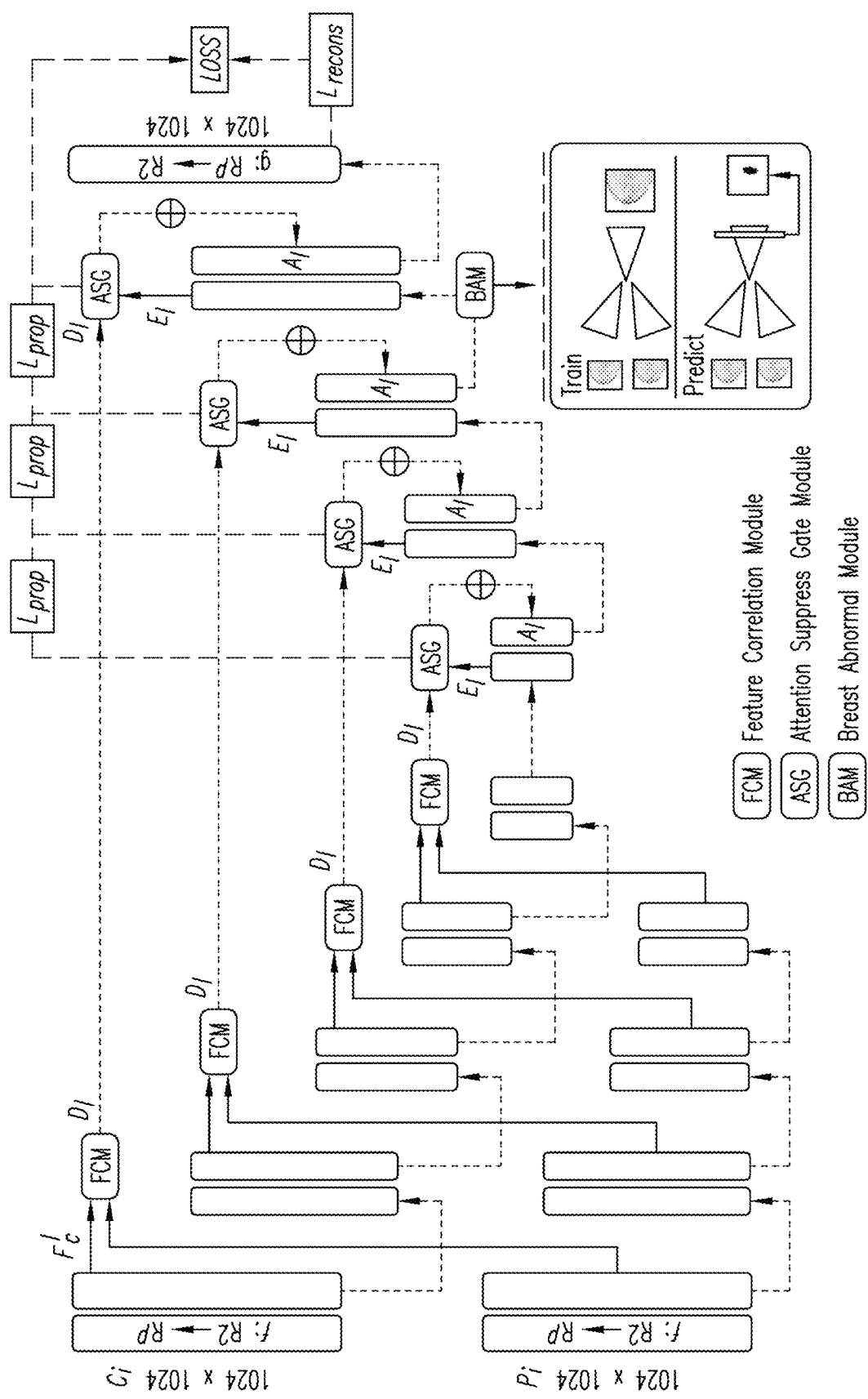
FIG. 15 depict aspects of an overview of the structure of the Unsupervised Feature Correlation Network (UFCN)

Unsupervised feature correlation network (UFCN)—the disclosed model, UFCN, is an unsupervised CNN-based model. UFCN includes an identical parallel twin encoder and a reconstruction decoder as shown in FIG. 15. UFCN embeds feature correlation modules (FCMs) into encoder layers and attention suppress gate modules (ASGs) into decoder layers. The breast abnormality map detection module (BAM) is embedded at the layer L-1 of the decoder, where L is the total number of layers, to generate AVMs. A pair of current and prior images are input into the two identical parallel CNN blocks to learn the features. In each corresponding CNN block, the learned features of pairs of images using function $f$ are fed into FCMs to learn differences between current and prior images and their features. The output of FCM, $D_i$, represents the breast tissue changes from prior mammograms ($P_i$) to current mammograms ($C_i$). Dis residual connect to ASG at the decoder stage. The output of the decoder is the reconstruction of current mammograms, $\hat{C_i}$. FIG. 15 illustrates an overview of the structure of the UCFN model. The model includes two encoders with inputs $C_i$ (current mammogram) and $P_i$ (previous mammogram), and one decoder output $\mathbb{R}$. The FCM panel is the feature correlation map module (FCM), which computes the signal difference between features extracted using function $f$ from current and previous mammograms at each layer. The ASG panel is the attention suppress gate. The BAM panel is the breast abnormality detection map module, which predicts the abnormal variation maps (AVM) as output. $\oplus$ is concatenation, and $\ominus$ is matrix subtraction.

Selecting an activation function to trigger the model neurons in an unsupervised learning model is disclosed. Hence, three activation functions are employed: (1) ReLU activation function ($\sigma 1$) shown in Eq. (19), sigmoid activation function (σ2) shown in Eq. (20), and SiLU activation function (σ3) shown in Eq. (21).

$$\sigma_1(x) = \max(0, x), \quad (19)$$

$$\sigma2(x) = 1/(1 + e^{-x}) \quad (20)$$

$$\sigma_3(x) = x \cdot \sigma_2(\beta x), \quad (21)$$

where β is a trainable parameter and x is input feature. The SiLU activation function has a desirable characteristic known as self-stabilization. This means that the point at which the derivative of the function is zero acts as a "soft floor" for the weights, which helps to regulate the learning process by discouraging the development of excessively large weights. The SiLU activation in the FCM modules and CNN blocks in the encoder and decoder is implemented; the ReLU activation in the ASG modules for faster gradient descent is implemented; and the sigmoid activation in the ASG and BAM modules is implemented.

Figure 16A:
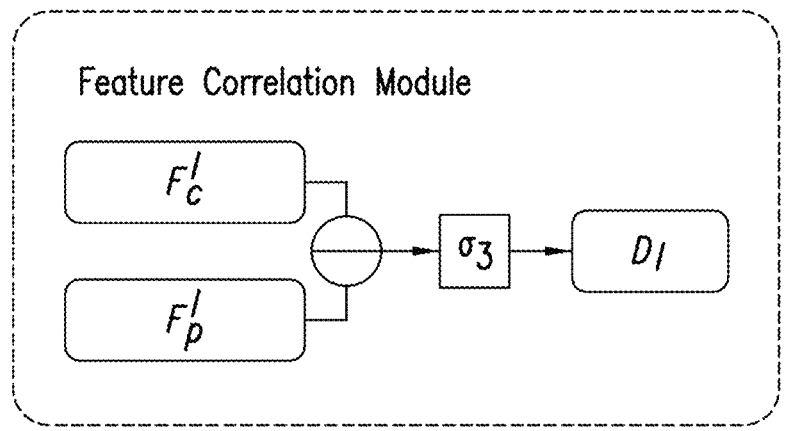
FIGS. 16A-16C, collectively referred to as FIG. 16, depict aspects of block diagrams of feature correlation, attention suppress gate, and breast abnormal modules.

Feature correlation module (FCM)—To take advantage of the paired images through the reconstruction process, FCM modules are embedded into each layer of the encoder stage. FCM, illustrated in FIG. 16A, learns multi-scaled feature correlation between current and prior mammograms to learn newly grown tumors. The FCM output, $D_l \in R^p$, can be expressed as $D_l = \sigma_3(F_C^l) \oplus \sigma_3(F_P^l)$, where $F_C^l = f(C_i) \in R^p$ and $F_P^l = \theta(P_i) \in R^p$ are the feature maps of the current and prior mammograms at layer l, ⊕ is matrix subtraction, and σ is the SiLU activation function. FIG. 16A illustrates a block diagram of the feature correlation module (FCM). $F_C^l$ and $F_P^l$ are current year and previous year feature maps, respectively, generated in the layer l of the decoder (function $f$). $D_l$ is output from the FCM in layer l.

Figure 16B:
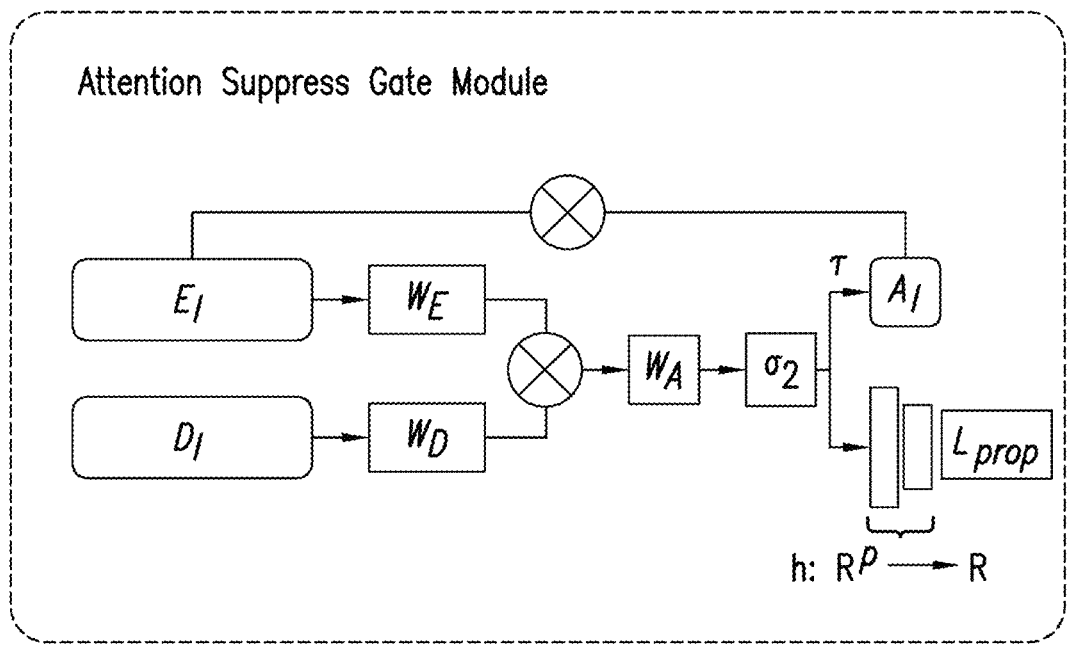

Attention suppress gate module (ASG)—The ASG module is embedded into each layer of the decoder stage at the image $C_i$ reconstruction process with function g. The ASG, illustrated in FIG. 16B, aims to selectively highlight specific areas of an image through attention weightings. In the specific solution at hand, ASGs are also utilized to completely remove any activation from the images of normal patients. As the model is trained, the soft attention aspect will prioritize regions with greater weights while the hard suppressor—mapping function h—eliminates any activity from the normal images. FIG. 16B illustrates a block diagram of the attention suppresses gate module (ASG). $E_l$ is feature generated in encoder (function g) layer l, $D_l$ is output of FCM, and $A_l$ is attention coefficients. The ⊗ is Hadamard product.

ASG adds weight to breast tissue areas and reduces the impact of changes in breast borders. ASG at layer l outputs attention coefficients $A_l \in R^p$ while taking $D_l$ and $E_{l-1} \in R^p$ as input, where $E_{l-1}$ is decoder output at layer l-1. Al is computed as $A_l = \sigma_2(\sigma_1(W_E^T E_{l-1} \otimes W_D^T D_l) W_A^T) W_E^T E_{l-1}$, where $\sigma_2$ is the sigmoid activation function, and ⊗ is Hadamard product. To have more aggressive soft attention, a threshold λ is introduced to suppress the attention coefficients lower than the threshold and to remain the attention region for the attention coefficients higher than the threshold. To prevent neurons from dying, the lease-activated region (the feature map region below the threshold) is suppressed to a small constant value instead of zero.

The hard suppressor acts as a regularizer that maps region-activated feature map to probability of $\hat{y}$ as $\hat{y}$ =h $(A_l) = \sigma_2(W_f^T A_l) \in R$ where $W_f \in R^p$ is a vector of trainable parameters used herein. The mapped probability of normal and cancer, $\hat{y}$, are participated in loss term to compute the gradient. ASG progressively suppresses features responding in irrelevant background regions in images of a normal patient. The output of ASG at each layer l is concatenated with its corresponding encoder features at each layer l, and then the features are fed forward to the next layer until reaching the last layer that reconstructs $C_i$ and outputs $\hat{C}_i$.

Figure 16C:
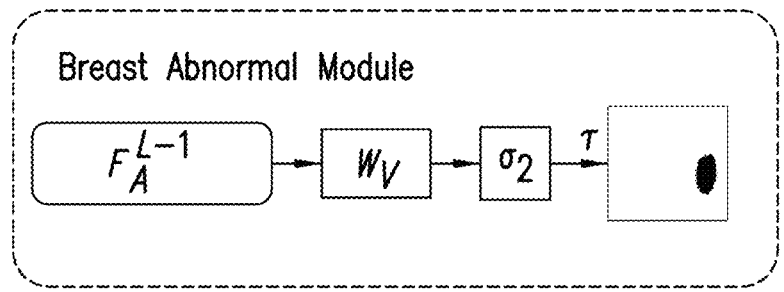

Breast abnormality detection module (BAM)—As defined above, the optimal AVM is predicted with learned $f$ and g. To achieve an accurate binary mask AVM indicating the abnormal regions, BAM is embedded in the decoder stage. The BAM module, illustrated in FIG. 16C, is applied to layer L-1 which outputs and generates AVMs as AVM=$\sigma_2(W v^T F_A^{L-1})$, where $F_A^{L-1}$ is the extracted feature vector at layer L-1. The module applies a convolution layer to blend the $F_A$ features, then employs the sigmoid activation function. Finally, using a threshold τ (0.5 used herein), BAM selects the most activated regions as AVMs, indicating cancer regions. FIG. 16C illustrates a block diagram of the breast abnormality detection module (BAM). $F_A^{L-1}$ is the feature map from layer L-1.

Loss function—The loss function LOSS includes a constraint on current year image reconstruction—the similarity index measure (SSIM) reconstruction loss, a layer wise constraint on the probability of binary labels (normal and cancer) of images y—the binary cross function (BE), and a constraint on weights—the L2 norm function, denoted as follows:

$$\text{LOSS} = \underbrace{\frac{1}{N} \sum_{p \in P} 1 - SSIM(p)}_{\text{Recons}} + \underbrace{\lambda_1 \sum_{l \in L} BE(y, \hat{y})}_{\text{Prob}} + \underbrace{\lambda_2 \sum_{w_i \in W} w_i^2}_{L_2 \text{Regularizer}} \quad (22)$$

where $$SSIM(p) = \frac{2\mu_i \mu_j + C_1}{\mu_i^2 + \mu_j^2 + C_1} \cdot \frac{2\sigma_{ij} + C_2}{\sigma_i^2 + \sigma_j^2 + C_2}, \quad (23)$$

where μ represents the mean of pixel intensities, σ in this equation denotes the standard deviation of pixel intensities, $C_1$ and $C_2$ are constant for stability. $C_1$ is given by $C_1 = (K_1 T)^2$ and $C_2 = (K_2^T)$ where $K_1$ and $K_2$ are constant values, and T is the dynamic range of pixel intensities.

The probability distribution constraint is defined as:

$$BE(y, \hat{y}) = -(y \log(\hat{y}) + (1 - y) \log(1 - \hat{y})), \quad (24)$$

where y is the binary label for the h(x) at ASG, $\hat{y}$ is prediction of the h(x), and x is input feature map.

Baseline and Variant Models

In the course of the evaluations, the following models were used as baseline models and variants of the disclosed model. All baseline models are supervised autoencoder-shaped models. The baseline models, disclosed model, and variants of the disclosed model were trained with the same training dataset and input dimension. However, the baseline models were only trained using cancer images due to their design. To have a fair comparison, all baseline models and variation models employed the same numbers of building blocks.

U-Net—The performance of the disclosed method was compared with that of the U-Net. The structure of U-Net was kept as standard U-Net and optimized the feature depth at each building block. The U-Net model contains five building blocks. The feature depth of each building block is indicated as 64, 128, 256, 512, 1024. Dice loss (Eq. (25)) was used to optimize the U-Net gradient as follows:

$$L_{Dice} = 1 - \frac{\sum_{n=1}^{N} s_n r_n + \epsilon}{\sum_{n=1}^{N} s_n + r_n + \epsilon} - \frac{\sum_{n=1}^{N} (1-s_n)(1-r_n) + \epsilon}{\sum_{n=1}^{N} 2 - s_n - r_n + \epsilon}, \quad (25)$$

where N is the number of images in this equation, s is predicted probability, r is ground truth, and ∈ is a hyperparameter to ensure the stability of the loss function.

Attention U-Net—The performance of the disclosed model was also compared with that of U-Net attention. The structure of attention U-Net remained the same as its original and the feature depth was optimized at each building block. The feature depths of building blocks are 64, 128, 256, 512, 1024. Dice loss (Eq. (25)) was to optimize the attention U-Net gradient.

U-Net++—U-Net++ is another baseline model used in the evaluation. The structure of the U-Net++ model remained the same. Feature depth of 32, 64, 128, 256, 512, 1024 was used for building blocks. U-Net++ is an extension of the U-Net architecture for semantic image segmentation. The model structure is similar to U-Net, but with additional nested and dense skip connections. Dice loss (Eq. (25)) was used to optimize the attention U-Net++ gradient.

SegResNet—SegResNet was used for performance comparison too. SegResNet is a deep neural network architecture designed for semantic image segmentation tasks. The SegResNet model is based on the ResNet architecture. The SegResNet model enhances the performance of ResNet for image segmentation tasks by adding a decoder network to the architecture. This decoder network is composed of several deconvolutional (or transposed convolutional) layers, which upsample the features extracted by the ResNet encoder and generate a pixel-wise segmentation mask. Dice loss (Eq. (25)) was used to optimize the SegResNet gradient.

V-Net—The disclosed model was also compared with V-Net. The V-Net architecture bears some resemblance to the U-Net architecture, but with some differences. Firstly, V-Net does not employ Batch Normalization, unlike U-Net. In addition, while U-Net uses element-wise summation after each successive convolutional layer, V-Net does not. In the evaluation, the same structure as the element-wise summation was kept after each successive convolutional layer, where V-Net does not. In the evaluation, the same structure was kept as the gradient.

UFCN-variants—As discussed further above, the activation function is used to obtain accurate abnormal variation maps. Therefore, to evaluate how the activation function impacts the disclosed UFCN model, two variations of the disclosed model were evaluated: (1) UFCN-T, and (2) UFCN-R. In the UFCN-T model, a new activation function is defined, which is called Tilu, to enhance the activated region by dropping the low-signaled neurons. The Tilu activation function can be expressed as tiLU (x)=max(λ, x), where λ is a small constant value as hard floor. The UFCN-R used regular ReLU activation function in the entire model. The loss function remains the same as that of the method expressed in Eq. (22).

Data & Evaluation Setup

For the evaluation setup, PyTorch (an open-source deep learning framework) was used to implement the disclosed method, variants of the disclosed method and the baseline models. Data pre-processing was performed with High-Performance Computing (HPC) with 36 cores Xeon CPU. The disclosed method was trained on XSEDE (the Extreme Science and Engineering Discovery Environment having a powerful collection of integrated digital resources and services) with multiple 32 GB V100 GPU nodes. The starting learning rate in a range from 1e-2 to 1e-5 was used. A learning rate scheduler was used to optimize the learning rate of the disclosed model. The evaluation setup of the disclosed model and the baseline model is shown in Table 8.

TABLE 8

Evaluation Set-Up Of Models

| Model | Parameters | Optimizer | Activation functions | Weight initialize[a] |
|---|---|---|---|---|
| U-Net | 26M | Adam | ReLu/Sigmoid | $W \sim \mathcal{N}\left(0, \frac{1}{\sqrt{n}}\right)$ |
| U-Net attention | 32M | Adam | ReLu/Sigmoid | $W \sim \mathcal{N}\left(0, \frac{1}{\sqrt{n}}\right)$ |
| U-Net++ | 36M | Adam | ReLu/Sigmoid | $W \sim \mathcal{N}\left(0, \frac{1}{\sqrt{n}}\right)$ |
| SegResNet | 25M | Adam | ReLu/Sigmoid | $W \sim \mathcal{N}\left(0, \frac{1}{\sqrt{n}}\right)$ |
| V-Net | 9M | Adam | ReLu/Sigmoid | $W \sim \mathcal{N}\left(0, \frac{1}{\sqrt{n}}\right)$ |
| UFCN-T | 391M | Adam | Tilu/Sigmoid | $W \sim \mathcal{N}\left(0, \frac{1}{\sqrt{n}}\right)$ |
| UFCN-R | 391M | Adam | ReLu/Sigmoid | $W \sim \mathcal{N}\left(0, \frac{1}{\sqrt{n}}\right)$ |
| UFCN | 391M | Adam | ReLu/Sigmoid/ SiLU | $W \sim \mathcal{N}\left(0, \frac{1}{\sqrt{n}}\right)$ |

[a]n is number of input.

Figure 17A:
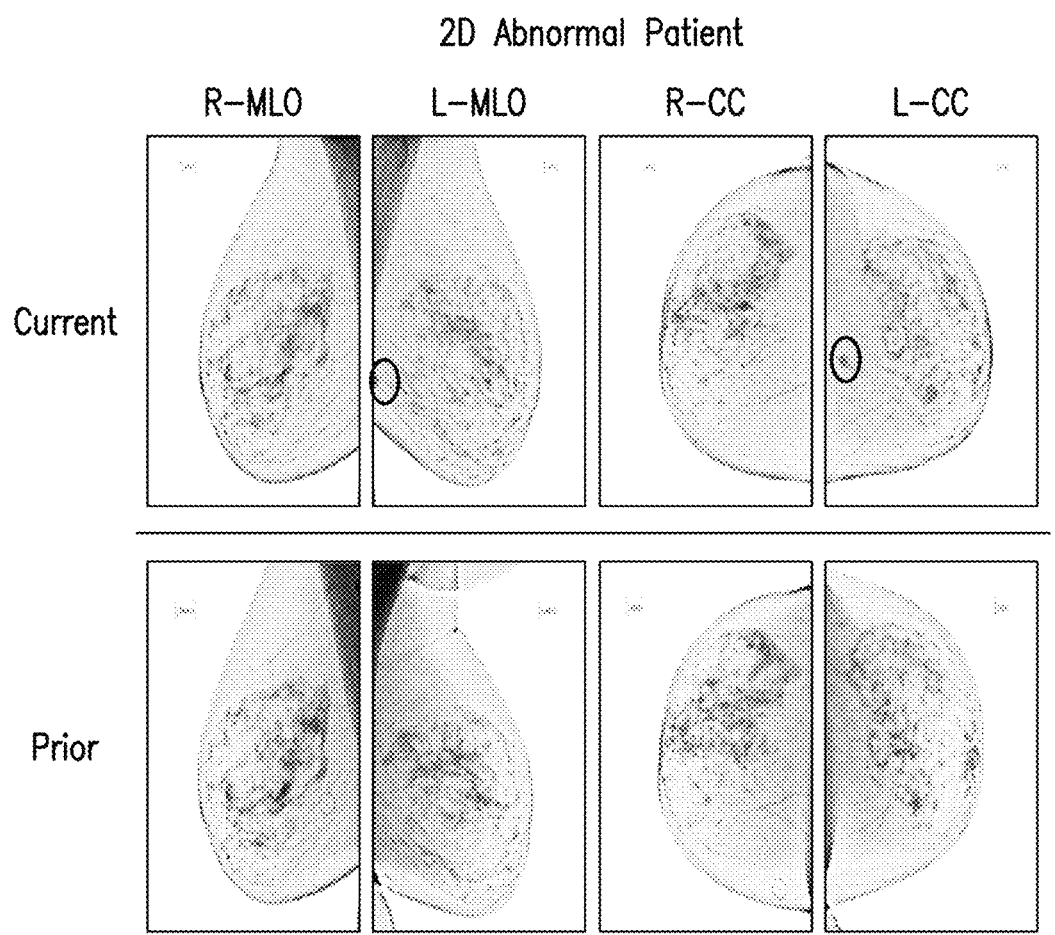
FIGS. 17A and 17B, collectively referred to as FIG. 17, depict aspects of current and prior mammograms for an abnormal patient and a normal patient.
Figure 17B:
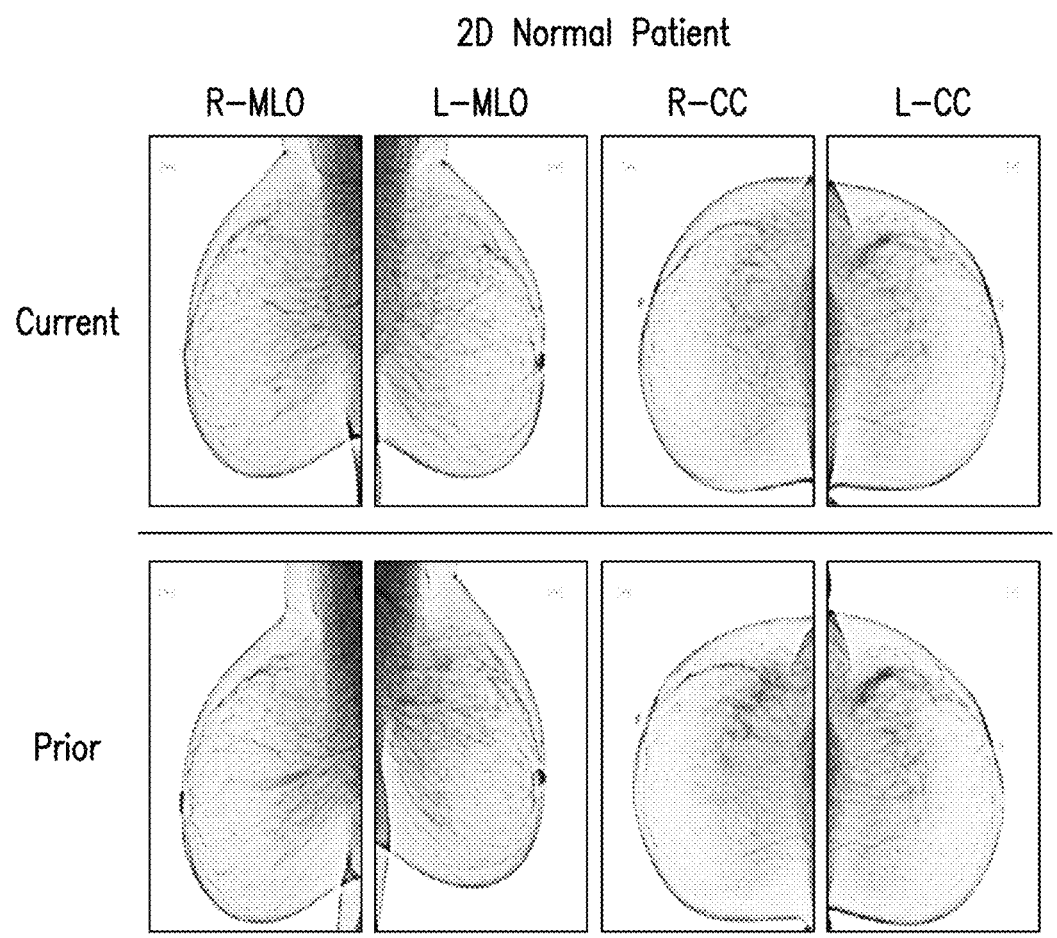

With respect to data, the disclosed and baseline models were trained, tested, and vali-dated on the UConn Health Center (UCHC) dataset, which includes both current and historical mammograms as shown in FIGS. 17a and 17b. This dataset was compiled by collecting FFDMs from patients who underwent mammogram exams at UCHC between Oct. 31, 2006, and Aug. 23, 2021, using a mammography system by Hologic® of Marlborough MA. The UCHC Institutional Review Board approved the data collection, and the Diagnostic Imaging Informatics Department at UCHC provided support in exporting the DICOMs from the Picture Archiving and Communication Systems (PACS) at UCHC. To ensure patient privacy, identifiers were removed and replaced with a standard naming convention. The mammograms in the dataset were annotated by radiologists. FIGS. 17a and 17b illustrate examples of current and prior mammograms of (a) an abnormal patient and (b) a normal patient from the dataset, respectively. The circles indicate the abnormal location.

In this collection, 493 mammogram pairs (current and their corresponding prior normal mammograms) are labeled cancer, and 581 mammogram pairs are labeled normal. Data pre-processing includes normalization, re-scale, and augmentation are applied. No alignment was performed in this evaluation. The ground truth used for evaluation is annotated by radiologists.

To ensure the diversity and generalizability of the dataset, various types of tumors and breast densities were included. The mass type in the dataset includes round, oval, architectural distortion, irregular, and lobulated, while the microcalcification type includes amorphous, coarse, fine linear branching, pleomorphic, punctate, and round with regular shapes. All types of breast densities, including fatty, fibroglandular dense, heterogeneously dense, and extremely dense breasts, were also included. The fibroglandular dense and heterogeneously dense breast types cover a significant portion of the dataset.

Results

The performance of the disclosed UFCN model and variants of the disclosed model was compared with the baseline models discussed further above, in terms of Dice score, cancer detection rate (cDR), and normal detection rate (nDR) for different cancer types (Mass, microcalcifications (Calc), Architectural Distortion (AD)). The results for different cancer types are shown in Table 9.

TABLE 9

Performance of models on localizing abnormalities and detection rate for normal mammograms and cancer mammograms.

| Model | AD Dice | AD cDR | Mass Dice | Mass cDR | Cals Dice | Cals cDR | Normal nDR |
|---|---|---|---|---|---|---|---|
| U-Net | 0.47 | 0.71 | 0.64 | 0.87 | 0.44 | 0.71 | 0.09 |
| U-Net attention | 0.48 | 0.79 | 0.66 | 0.87 | 0.40 | 0.68 | 0.09 |
| U-Net++ | 0.60 | 0.86 | 0.68 | 0.89 | 0.38 | 0.58 | 0.08 |
| SegResNet | 0.58 | 0.86 | 0.63 | 0.85 | 0.39 | 0.61 | 0.21 |
| V-Net | 0.46 | 0.64 | 0.58 | 0.75 | 0.29 | 0.45 | 0.08 |
| UFCN-T | 0.66 | 0.86 | 0.61 | 0.76 | 0.59 | 0.61 | 0.17 |
| UFCN-R | 0.35 | 0.64 | 0.58 | 0.73 | 0.36 | 0.55 | 0.58 |
| UFCN | 0.60 | 0.79 | 0.69 | 0.91 | 0.57 | 0.74 | 0.73 |

Cancer detection is defined as binary detection when for cancer cases a cancer region is detected and for normal cases, a minimal region that is below the threshold as shown in Eq. (27) is detected. Additionally, the performance of all the models was compared in terms of Accuracy, Sensitivity, Precision, and F1 in detecting abnormalities. True Positive (T P) and True Negative (T N) used in computing the aforementioned metrics are defined in Eqs. (26) and (27), respectively.

$$TP = \begin{cases} 1, & \text{if dice } (I) > 0.01 \\ 0, & \text{otherwise} \end{cases} \quad (26)$$

where $I$ is the input test mammogram image.

$$TN = \begin{cases} 1, & \text{if } \sum_{i,j \in w,h} I(i,j) < 0.01 \\ 0, & \text{otherwise} \end{cases} \quad (27)$$

where $w, h$ are the width and height of the input image.

Overall results-Table 9 highlights the superiority of the disclosed model, UFCN, in terms of cancer detection. This model achieves the best cancer detection rate for both masses and microcalcifications, as well as the best Dice score for masses. Furthermore, the disclosed UFCN model also performs well in architectural distortion cancer type, achieving the second-best performance in terms of the Dice score and the third-best in terms of cancer detection rate.

When compared to its variant, UFCN-R, which uses the ReLU activation function, the disclosed UFCN model outperforms in all types of cancers. The inferior performance of UFCN-R may be caused by the dying ReLU, in which ASG suppresses the majority of nodes to zero, resulting in a decrease in the activated regions and shrinkage of the abnormal variation map. In contrast, the use of the "soft floor" SiLU activation function in UFCN prevents dead neurons and provides the necessary stability to activate the attention regions while simultaneously suppressing the irrelevant background of cancer images and normal images. The results demonstrate the superior performance of the UFCN model in cancer detection, even though the model is trained in an unsupervised fashion.

For the architectural distortion cancer type, the UFCN-T model shows superior performance in both Dice score and cancer detection rate. Although the TiLU activation function uses a hard floor like ReLU, it employs a slightly tighter bound as a hard floor to avoid the dying ReLU caused by the properties of zero, unlike the ReLU activation function that uses 0 for the hard floor. In other words, the UFCN-T model maximizes the variation between the current year image and the prior image, which is also observable by its superior performance in detecting microcalcifications and comparable performance in detecting masses.

The disclosed model, UFCN, outperforms all baseline models including U-Net, U-Net attention, U-Net++, SegResNet, and V-Net in almost all the metrics. Among all baseline models, U-Net++ showed the best performance in terms of cancer detection rate and Dice score in architectural distortion and mass cancer types, while U-Net showed a decent Dice score and cancer detection rate in Cals among all baseline models. However, both models showed relatively low performance in normal tissue classification, as indicated by their low nDR. In contrast, UFCN achieved the best performance in terms of cancer detection rate and Dice score for mass and the second-best for calcifications, as well as the highest nDR among all the models. These findings demonstrate the superior performance of the disclosed UFCN, which is trained in an unsupervised fashion. Specifically, UFCN-T showed the best performance overall, with a Dice score of 0.66 and a cDR of 0.86, followed by UFCN with a Dice score of 0.69 and a cDR of 0.91. These findings demonstrate the superior performance of the disclosed UFCN model, which is trained in an unsupervised fashion.

In addition to evaluating cancer detection rates and Dice scores, the performance of the UFCN model in detecting normal and cancer cases in terms of Accuracy, Sensitivity, Precision, and F1 scores was also assessed (see Table 10). Notably, all the baseline models do not perform well when applied to normal cases. The baseline models were originally identified to identify abnormal tissue areas in cancer images, and the baseline models often rely on pre-classified cancer data. This limitation causes the baseline models to fail to distinguish between cancer and normal cases. As a result, the U-Net model shows poor performance in terms of Accuracy (0.41), Sensitivity (0.43), and F1 score (0.56) but a better Precision score (0.80). The SegResNet showed slightly better performance in Accuracy (0.47) and Sensitivity (0.46) compared with U-Net. The V-Net shows least performance in terms of all evaluation metrics.

TABLE 10

Cancer and normal detection performance of models.

| Model | Accuracy | Sensitivity | Precision | F1 |
|---|---|---|---|---|
| U-Net | 0.41 | 0.43 | 0.80 | 0.56 |
| U-Net attention | 0.42 | 0.43 | 0.80 | 0.56 |
| U-Net++ | 0.40 | 0.42 | 0.79 | 0.55 |
| SegResNet | 0.47 | 0.46 | 0.78 | 0.47 |
| V-Net | 0.34 | 0.37 | 0.64 | 0.47 |
| UFCN-T | 0.43 | 0.43 | 0.73 | 0.54 |
| UFCN-R | 0.62 | 0.57 | 0.67 | 0.62 |
| UFCN | 0.78 | 0.72 | 0.84 | 0.78 |

Although UFCN-T shows a higher detection rate for architectural distortion and microcalcification, its normal detection rate is lower, and its accuracy (0.43), sensitivity (0.43), and F1 score (0.54) are comparable with those of U-Net. Similar to U-Net, the precision score of UFCN-T yields the third-best result. UFCN-R shows a better normal detection rate compared to U-Net and UFCN-T. However, the trade-off to increasing the normal detection rate in UFCN-R is a lower detection rate for cancer cases. Hence, its accuracy (0.62), sensitivity (0.57), and F1 score (0.62) are the second-best results. However, its precision is the lowest compared to those of the other models. The disclosed UFCN model shows the best performance in terms of all the evaluation metrics compared to the other models. The UFCN model achieves the best normal detection rate (0.73) while still maintaining a better performance for cancer detection. As Table 10 demonstrates, UFCN shows the best accuracy (0.78), sensitivity (0.72), precision (0.84), and F1 score (0.78).

Cancerous case results—The AVM outputs of the disclosed UFCN model, the variants of the disclosed model, and also the segmentation outputs of the baseline models were examined.

Figure 18:
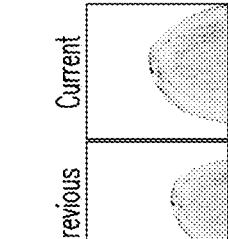
FIG. 18 depict aspects of outputs of the baseline and disclosed models and ground truth (GT)

As shown in FIG. 18, prediction by the UFCN is very close to the ground truth annotations. Especially for architectural distortion (AD) and microcalcification (CALS), the UFCN model can generate more precise abnormal tissue maps (CALS and AD). As can be seen in FIG. 18 (CALS), U-Net, attention U-Net, U-Net++ and SegResNet models fail to detect microcalcification. The UFCN-R model misses the detection for architectural distortion. As discussed above, the hard floor of ReLU causes the active region to shrink as shown in FIG. 18. The UFCN-T model generates larger abnormal tissue areas compared with UFCN and UFCN-R models. FIG. 18 illustrates outputs of the baseline and disclosed models. The first row shows current year, second row shows prior year, and third row shows ground truth (GT) images. The circle is enlarged area for better visualization. F indicates failed to localize abnormal tissue.

Figure 19A:
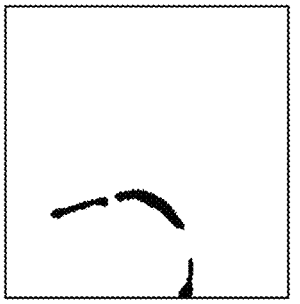
Figure 19B:
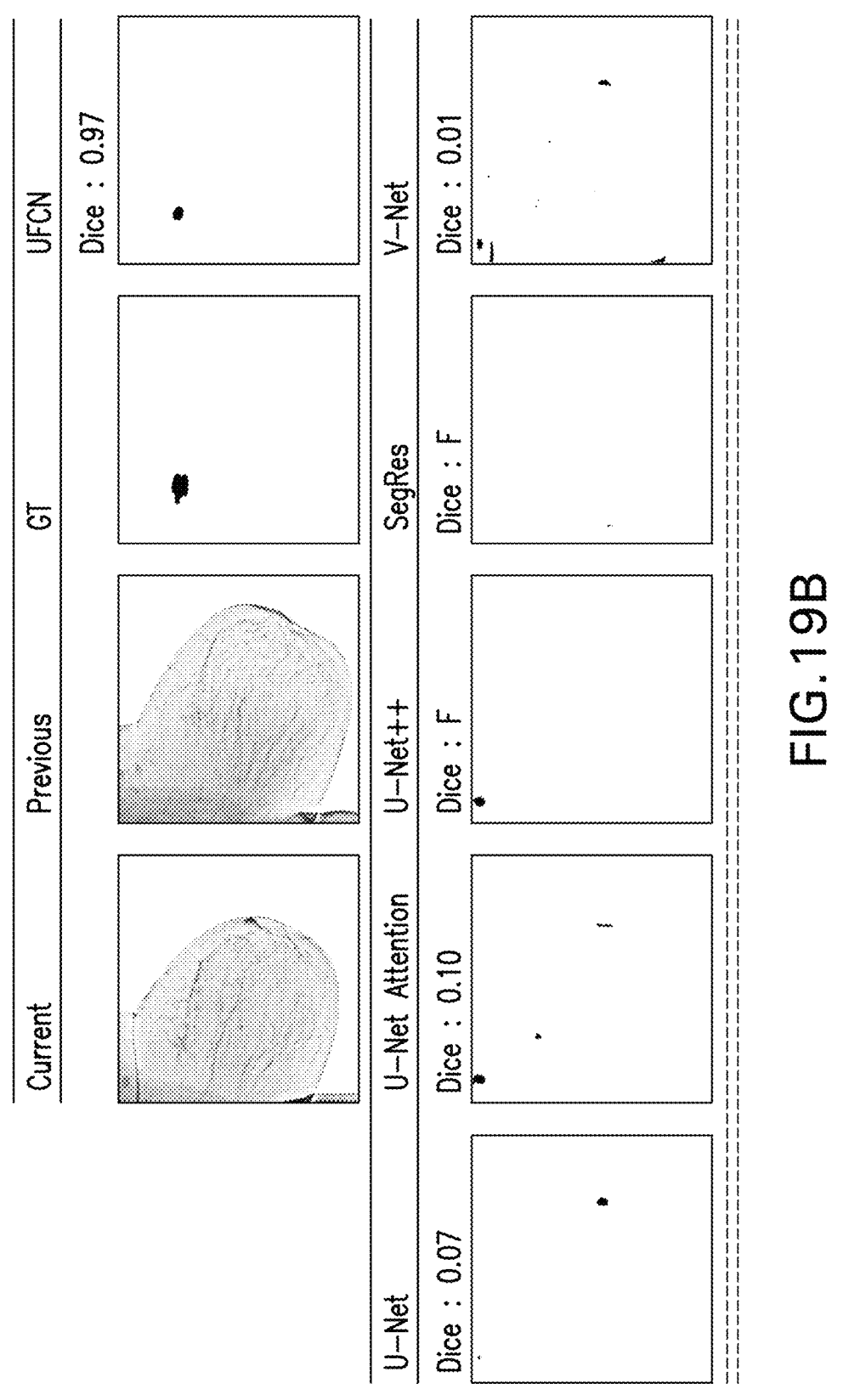

What stands out in the evaluation results is the skin tumor case as shown in FIG. 19A. This case was only in the UCHC test dataset. As this figure shows, the U-Net model misses the skin area and wrongly detects a few other regions as tumor locations. On the other hand, the disclosed UFCN model is able to precisely generate the abnormal region, which indicates that the ASG module in the disclosed UFCN model was not activated in the breast tissue area, but instead it was activated in the area where the abnormal changes existed. This demonstrates the effectiveness of the ASG mechanism in accurately localizing the abnormal tissue region in medical images. Furthermore, this finding highlights the importance of developing models that are specifically designed to handle diverse abnormalities in medical images. The disclosed UFCN model demonstrates superior performance in detecting abnormal tissue areas, including those that may not be related to the specific medical condition under consideration, such as in the case of skin tumors. FIGS. 19A and 19B demonstrate special cases. FIG. 19A illustrates an abnormal tissue area that is located at breast skin. FIG. 19B illustrates a normal high intensity region.

In FIG. 19B, the output maps generated by all baseline models and the disclosed UFCN model on a mass case were visualized. As can be observed in FIG. 19B, U-Net mistakenly identified a bright round area as an abnormal tissue region, leading to false negative detection. This limitation is a common issue with U-Net, where non-cancerous bright round areas are frequently misidentified as abnormal. U-Net++ and SegResNet also failed to detect cancer in this particular case. In contrast, the disclosed model, UFCN, effectively distinguishes between normal and abnormal bright areas by comparing current and previous images. Consequently, the abnormal variation map (AVM) generated by UFCN shows more precise and accurate cancer detection.

Figure 20:
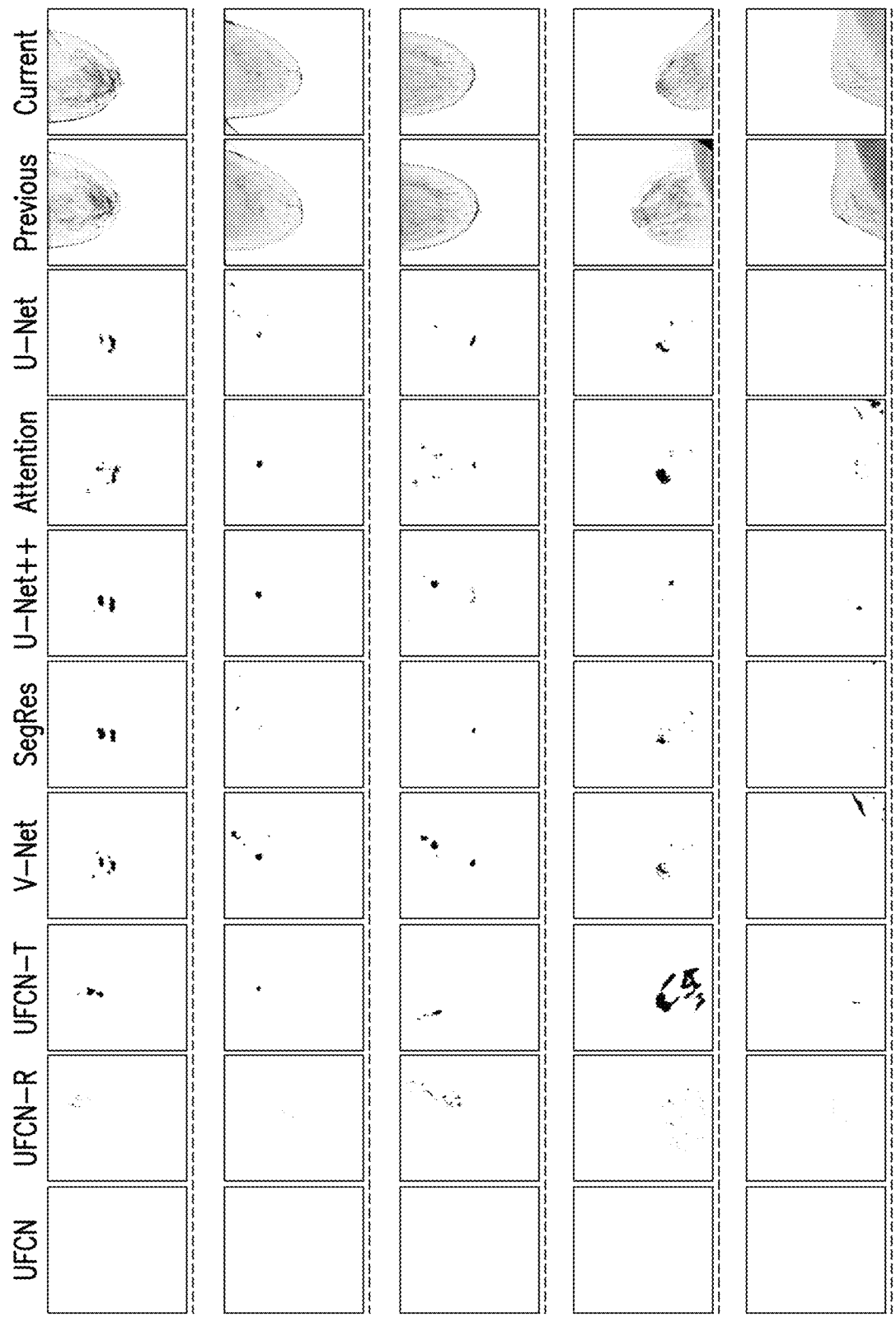
FIG. 20 depicts aspects of output of the baseline models and the disclosed models.

Non-cancerous results—FIG. 20 illustrates the prediction of all the models when inputs are normal cases. All baseline models showed detected tissues, and the wrongly detected tissue locations are similar in all models. Black output in FIG. 20 indicates no suspicious tissue detected. Although the UFCN-R model showed minor wrongly detected tissue areas compared with the U-Net and UFCN-T models, it still performed relatively well. However, the disclosed UFCN model showed no detection of abnormal tissues in these normal cases, indicating its high accuracy in distinguishing between normal and abnormal cases.

As demonstrated above, by learning the differences between the current and prior images unsupervised cancer area localization can be achieved. Labeling in medical image studies is expensive and prone to errors, making unsupervised learning an ideal approach. The evaluation results show that with prior images, the disclosed UFCN model can achieve results as good as those of a supervised model. Additionally, the disclosed UFCN model outperformed the supervised model in detecting complex tumors that the latter was unable to detect.

Overall, the evaluation highlights the benefits of unsupervised learning for medical image analysis, particularly for tasks such as cancer area localization. By leveraging longitudinal data and advanced machine learning techniques, the need for costly and time-consuming manual labeling can be reduced while still achieving high levels of accuracy and sensitivity in cancer detection. These findings demonstrate improvements in the efficiency and effectiveness of cancer screening and diagnosis that can ultimately lead to better patient outcomes.

Benefits and Advantages

Breast cancer remains a leading cause of death for women worldwide. Early detection and accurate diagnosis of breast abnormalities are crucial for improving patient outcomes. However, traditional screening methods such as mammography have limitations in terms of accuracy and sensitivity, leading to missed or misdiagnosed cases. One of the main challenges in detecting cancer is the lack of large annotated datasets to train advanced segmentation models.

To address this issue, an unsupervised feature correlation network to predict breast abnormal variation maps using 2D mammograms was developed as discussed above. The disclosed UFCN model takes advantage of the reconstruction process of the current year and prior year images to extract tissue from different areas without a need for ground truth. By analyzing the differences between the two images, the disclosed UFCN model can identify abnormal variations that may indicate the presence of cancer.

The disclosed UFCN model is embedded with novel features-a correlation module, an attention suppression gate, and a breast abnormality module, all of which work together to improve the accuracy of the prediction. The feature correlation module allows the model to identify patterns and relationships between different features, while the attention suppression gate helps to filter out irrelevant information. The breast abnormality module then uses this information to classify the input as normal or cancerous.

Notably, the disclosed UFCN model not only provides breast abnormal variation maps but is also able to distinguish between normal and cancer inputs, making it more advanced compared to the state-of-the-art segmentation models. The state-of-the-art segmentation models need already classified cancer images, which requires applying a classification method first, then, using the segmentation method. The results of the study show that the disclosed model outperforms or performs as well as the supervised state-of-the-art segmentation models not only in localizing abnormal regions but also in recognizing normal tissues.

Figure 21:
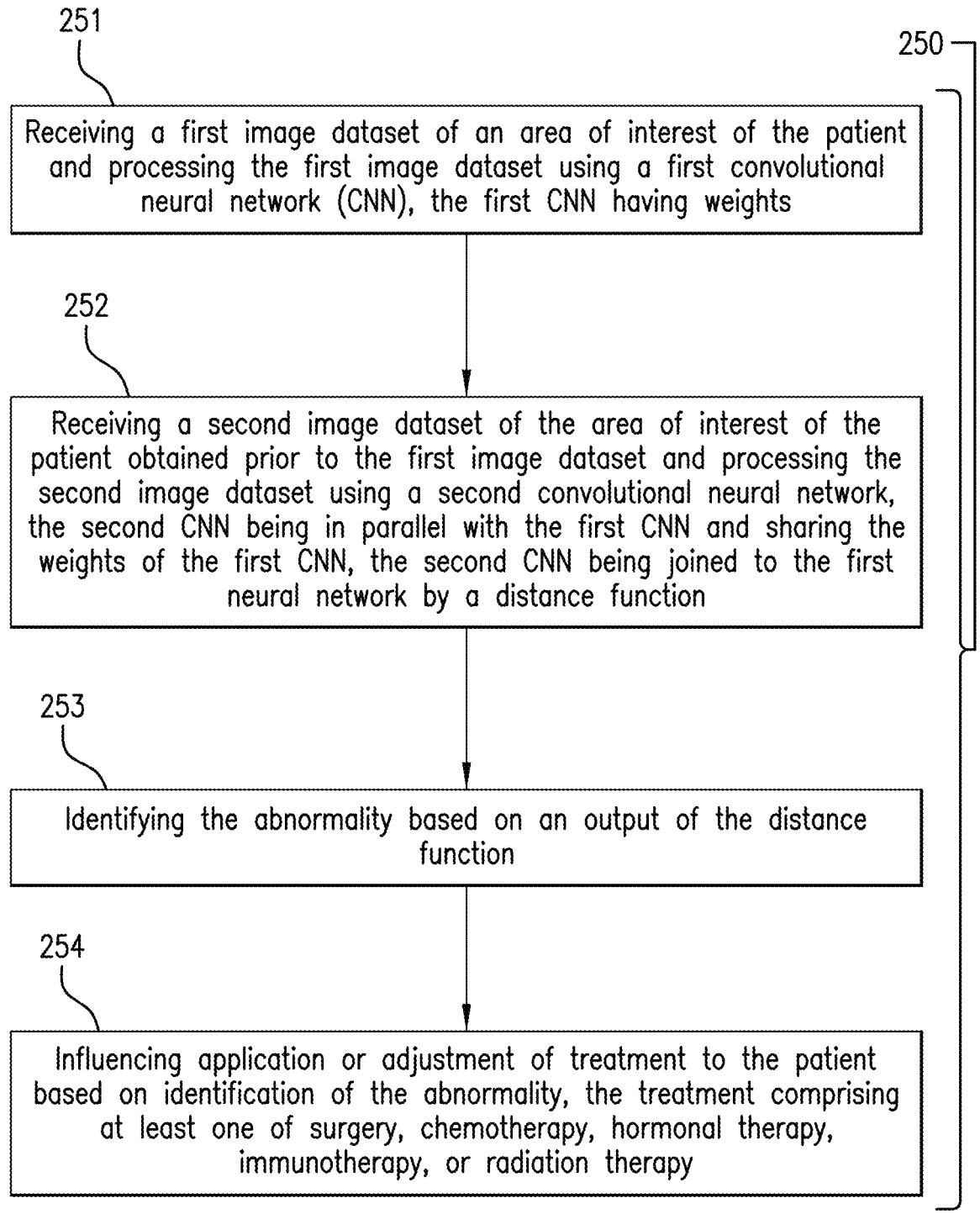
FIG. 21 is a flow chart for a method for treating an abnormality of a patient.

FIG. 21 is a flow chart for a method 250 for treating an abnormality of a patient. Stage 251 calls for receiving a first image dataset of an area of interest of the patient and processing the first image dataset using a first convolutional neural network (CNN), the first CNN having weights. Stage 252 calls for receiving a second image dataset of the area of interest of the patient obtained prior to the first image dataset and processing the second image dataset using a second convolutional neural network, the second CNN being in parallel with the first CNN and sharing the weights of the first CNN, the second CNN being joined to the first neural network by a distance function. Stage 253 calls for identifying the abnormality based on an output of the distance function. Stage 254 calls for influencing application or adjustment of treatment to the patient based on identification of the abnormality, the treatment comprising at least one of surgery, chemotherapy, hormonal therapy, immunotherapy, or radiation therapy.

The method 250 may also include determining a location of the abnormality in the patient and influencing the application or adjustment of the treatment according to the location. In one or more embodiments, a device for identifying the abnormality and/or the location of the abnormality may output the identification and/or location to a controller that controls a treatment apparatus for treating the patient. For example, the controller may control a radiation therapy apparatus to direct radiation to the determined location (e.g., a selected area size) at a selected intensity for a selected amount of time for precise treatment of the patient that would decrease an amount of radiation applied to normal (i.e., non-abnormal) areas of the patient. Other types of treatment apparatus may also be controlled such as a surgical robot. FIG. 22 illustrates an abnormality identification and/or abnormality location determination device 260. The abnormality identification and/or abnormality location determination device 260 may be implemented using any of the novel algorithms disclosed herein such as FFS-CNN and/or UFCN for example. The device 260 is coupled to a controller 261 to transmit the identified abnormality and/or location of the abnormality to the controller 261. The controller 261 is coupled to a treatment apparatus 262 that is configured to treat the patient. The controller 261 includes a treatment algorithm upon which a control signal transmitted to the treatment apparatus 262 is based. In one or more embodiments, the treatment algorithm is a lookup table indicating an intensity of radiation and a time for application of the radiation that is to be applied based one or more characteristics (e.g., size) of the abnormality and location of the abnormality. Other algorithms may also be used depending on the type of treatment apparatus.

It can be appreciated that the techniques, apparatuses, and methods disclosed above are also applicable to identifying and/or locating biological abnormalities other than abnormalities such as cancer involving the breast. Prior and current images can be used to identify abnormalities such as cancer or tumors in various organs such as lungs, brain, kidneys, and pancreas in non-limiting examples. In addition, prior and current images can also be used to identify early stone formation in the kidneys and gall bladder for instance. Further, prior and current x-rays of teeth can be used to identify tooth decay, failing fillings, or the beginning of an abscess.

It can also be appreciated the that the techniques, apparatuses, and methods disclosed above are also applicable to identifying defects, which may also be referred to abnormalities, in commercial and industrial applications. Prior and current images (i.e., images made at different moments in time) can be used to identify various types of defects. The defects can be in various types of structural elements such as structural support elements (e.g., an I-beam), structural pressure excluding elements (e.g., chambers maintaining atmospheric pressure internally in higher pressure environments), and structural pressure containing elements (e.g., pressurized gas containers or pipes) in non-limiting examples. Non-limiting examples of defects include cracks and wall thinning such as due to corrosion or erosion. Defects in welds and connection devices such as bolts may also be identified. Various types of images or image data sets obtained from corresponding imagers (e.g., the instrument 102 illustrated in FIG. 1) may be used to identify the defects. Non-limiting examples of the images include visual images (e.g., camera images of the defects), ultrasonic images (e.g., images obtained using ultrasonic acoustic energy), radiographic images (e.g., images obtained using radiation energy), eddy current images (e.g., images obtained using induced eddy currents), magnetic particle images (e.g., images of magnetic particle distributions in or around the defects), acoustic emission images (e.g., images obtained using acoustic energy emitted by the defects), and dye penetrant images (images of dye penetrating the defects). It can further be appreciated that when a defect is identified, a repair or correction, which may be referred to as a treatment, can be administered or adjusted if already applied. A non-limiting embodiment of the repair can include grinding out the defect and filling the void with a weld. Alternatively, the repair can include replacing the structural element having the defect. In one or more embodiments, the abnormality identification and/or abnormality location determination device 260 illustrated in FIG. 22 can be used to identify and/or locate the defect in the structural element using the images obtained in two different moments in time. The device 260 can be coupled to the controller 261 to transmit the identified defect and/or location of the defect to the controller 261. The controller 261 can be coupled to the treatment apparatus 262, which for this application is configured to repair or correct the defect. A non-limiting embodiment of the treatment apparatus 262 for this application is a robotic welder.

It can be appreciated that the distance function in the above disclosed techniques accommodates for the normal variations of breast images due to changes in compression of the breast from year to year. Without the distance function, the algorithm would erroneous flag cancers increasing false positives. The disclosed distance function allows for an algorithm that is not simply a point-to-point subtraction of one image from another and thus makes the disclosed algorithm unique.

It is understood that when combinations, subsets, interactions, groups, etc. of components are described that, while specific reference of each various individual and collective combinations and permutations of these may not be explicitly described, each is specifically contemplated and described herein. This applies to all parts of this application including, but not limited to, steps in described methods. Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product on a computer-readable storage medium (non-transitory) having processor-executable instructions (e.g., computer software) embodied in the storage medium. Any suitable computer-readable storage medium may be utilized including hard disks, CD-ROMs, optical storage devices, magnetic storage devices, mem-resistors, Non-Volatile Random Access Memory (NVRAM), flash memory, or a combination thereof.

Throughout this application reference is made to block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a special purpose computer or other programmable data processing instrument to produce a machine, such that the processor-executable instructions which execute on the computer or other programmable data processing instrument create a device for implementing the functions specified in the flowchart block or blocks.

These processor-executable instructions may also be stored in a computer-readable memory or a computer-readable medium that may direct a computer or other programmable data processing instrument to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing instrument to cause a series of operational steps to be performed on the computer or other programmable instrument to produce a computer-implemented process such that the processor-executable instructions that execute on the computer or other programmable instrument provide steps for implementing the functions specified in the flowchart block or blocks.

Blocks of the block diagrams and flowcharts support combinations of devices for performing the specified functions, combinations of steps for performing the specified functions and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions.

Methods and systems are described for using a machine learning classifier(s) for detection and classification. Machine learning (ML) is a subfield of computer science that gives computers the ability to learn through training without being explicitly programmed. Machine learning methods include, but are not limited to, deep-learning techniques, naive Bayes classifiers, support vector machines, decision trees, neural networks, and the like.

The method steps recited throughout this disclosure may be combined, omitted, rearranged, or otherwise reorganized with any of the figures presented herein and are not intended to be limited to the four corners of each sheet presented. Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

All statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Various other components may be included and called upon for providing for aspects of the teachings herein. For example, additional materials, combinations of materials and/or omission of materials may be used to provide for added embodiments that are within the scope of the teachings herein. Adequacy of any particular element for practice of the teachings herein is to be judged from the perspective of a designer, manufacturer, seller, user, system operator or other similarly interested party, and such limitations are to be perceived according to the standards of the interested party.

In the disclosure hereof any element expressed as a means for performing a specified function is intended to encompass any way of performing that function including, for example, a) a combination of circuit elements and associated hardware which perform that function or b) software in any form, including, therefore, firmware, microcode or the like as set forth herein, combined with appropriate circuitry for executing that software to perform the function. Applicants thus regard any means which can provide those functionalities as equivalent to those shown herein. No functional language used in claims appended herein is to be construed as invoking 35 U.S.C. § 112(f) interpretations as "means-plus-function" language unless specifically expressed as such by use of the words "means for" or "steps for" within the respective claim.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements. The term "exemplary" is not intended to be construed as a superlative example but merely one of many possible examples. The conjunction "or" when used with a list of at least two terms is intended to mean any term or combination of terms. The conjunction "and/or" when used between two terms is intended to mean both terms or any individual term. The term "configured" relates one or more structural limitations of a device that are required for the device to perform the function or operation for which the device is configured. The terms "first" and "second" and like are used to distinguish terms and not to denote a particular order. The terms "coupled" or "joined" relates to being coupled or joined directly or indirectly using an intermediate device.

The disclosure illustratively disclosed herein may be practiced in the absence of any element which is not specifically disclosed herein.

While the methods and systems have been described in connection with preferred embodiments and specific examples, it is not intended that the scope be limited to the particular embodiments set forth, as the embodiments herein are intended in all respects to be illustrative rather than restrictive.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. An apparatus for treating an abnormality, the apparatus comprising:
   a processor;
   a non-transitory computer readable medium comprising:
   a first convolutional neural network (CNN) having weights;
   a second convolutional neural network in parallel with the first CNN and sharing the weights of the first CNN, the second CNN being joined to the first neural network by a distance function;
   instructions that when executed by the processor implement a method comprising:
      receiving a first image dataset of an area of interest and processing the first image dataset using the first CNN;
      receiving a second image dataset of the area of interest obtained prior to the first image dataset and processing the second image dataset using the second CNN;
      identifying the abnormality based on an output of the distance function; and
      outputting an indication of the abnormality, wherein the indication influences administering or adjusting treatment of the abnormality;
      wherein the first CNN comprises a first series of neural network layers that provide a current feature vector $f_C$ and the second CNN comprises a second series of neural network layers that provide a prior feature vector $f_P$, $f_C$ and $f_P$ being input to a first distance function that provides output $d_1$ and a second distance function that provides output $d_2$, $d_1$ and $d_2$ being input to a sigmoid function that identifies the abnormality.

2. The apparatus according to claim 1, wherein the abnormality is of a patient and the treatment comprises at least one of surgery, chemotherapy, hormonal therapy, immunotherapy, or radiation therapy.

3. The apparatus according to claim 1, wherein the abnormality is of a structural element and the treatment comprises at least one of repair or replacement of the structural element.

4. The apparatus according to claim 1, wherein the first CNN and the second CNN are trained using a plurality annotated training image datasets.

5. The apparatus according to claim 4, where the first CNN and the second CNN are trained using a loss function comprising a linear combination of an entropy term, an L1 norm term, and an L2 norm term.

6. The apparatus according to claim 1, wherein the method further comprises identifying a location of the abnormality.

7. The apparatus according to claim 6, wherein the current feature vector $f_C$ and the prior feature vector $f_P$ are provided to a feature correlation module (FCM) comprising a matrix subtraction function and a SiLU activation function that outputs a distance value.

8. The apparatus according to claim 7, further comprising an attention suppress gate module (ASGM) coupled to an output of the FCM, the ASGM comprising a Hadamard product function and a sigmoid activation function coupled to an output of the Hadamard product function.

9. The apparatus according to claim 8, further comprising a breast abnormal module (BAM) comprising a convolution layer configured to blend extracted feature vectors, a sigmoid function coupled to an output of the convolution layer, and a threshold value such that an output of the sigmoid function being greater than or equal to the threshold value provides indication of the location of the abnormality.

10. The apparatus according to claim 9, further comprising a loss function module, the loss function module comprising a similarity index measurement (SSIM) reconstruction loss, a binary cross function (BE), and an L2 norm function.

11. The apparatus according to claim 6, wherein the first CNN and the second CNN are trained using a plurality unannotated training image datasets.

12. A non-transitory computer readable medium for treating an abnormality comprising:
   a first convolutional neural network (CNN) having weights;
   a second convolutional neural network in parallel with the first CNN and sharing the weights of the first CNN, the second CNN being joined to the first CNN by a distance function;
   instructions that when executed by the processor implements a method comprising:
      receiving a first image dataset of an area of interest and processing the first image dataset using the first CNN;
      receiving a second image dataset of the area of interest obtained prior to the first image dataset and processing the second image dataset using the second CNN;
      identifying the abnormality based on an output of the distance function; and
      outputting an indication of the abnormality, wherein the indication influences administering or adjusting treatment of the abnormality;
      wherein the first CNN comprises a first series of neural network layers that provide a current feature vector $f_C$ and the second CNN comprises a second series of neural network layers that provide a prior feature vector $f_P$, $f_C$ and $f_P$ being input to a first distance function that provides output $d_1$ and a second distance function that provides output $d_2$, $d_1$ and $d_2$ being input to a sigmoid function that identifies the abnormality.

13. The non-transitory computer readable medium according to claim 12, wherein the method further comprises identifying a location of the abnormality.

14. The non-transitory computer readable medium according to claim 13, wherein the current feature vector $f_C$ and the prior feature vector $f_P$ are provided to a feature correlation module (FCM) comprising a matrix subtraction function and a SiLU activation function that outputs a distance value.

15. The non-transitory computer readable medium according to claim 14, further comprising an attention suppress gate module (ASGM) coupled to an output of the FCM, the ASGM comprising a Hadamard product function and a sigmoid activation function coupled to an output of the Hadamard product function.

16. The non-transitory computer readable medium according to claim 15, further comprising a breast abnormal module (BAM) comprising a convolution layer configured to blend extracted feature vectors, a sigmoid function coupled to an output of the convolution layer, and a threshold value such that an output of the sigmoid function being greater than or equal to the threshold value provides indication of the location of the abnormality.

17. A method for treating an abnormality, the method comprising:
receiving a first image dataset of an area of interest and processing the first image dataset using a first convolutional neural network (CNN), the first CNN having weights;
receiving a second image dataset of the area of interest obtained prior to the first image dataset and processing the second image dataset using a second convolutional neural network, the second CNN being in parallel with the first CNN and sharing the weights of the first CNN, the second CNN being joined to the first neural network by a distance function;
identifying the abnormality based on an output of the distance function; and
influencing application or adjustment of treatment of the abnormality based on identification of the abnormality;
wherein the first CNN comprises a first series of neural network layers that provide a current feature vector $f_C$ and the second CNN comprises a second series of neural network layers that provide a prior feature vector $f_P$, the method further comprising:
inputting $f_C$ and $f_P$ into a first distance function that provides output $d_1$;
inputting $f_C$ and $f_P$ into a second distance function that provides output $d_2$; and
inputting $d_1$ and $d_2$ into a sigmoid function that identifies the abnormality.

18. The method according to claim 17, further comprising identifying a location of the abnormality.

19. The method according to claim 18, further comprising inputting $f_C$ and $f_P$ into a feature correlation module (FCM) comprising a matrix subtraction function and a SiLU activation function that outputs a distance value.

20. The method according to claim 17, wherein the abnormality is of a patient and the treatment comprises at least one of surgery, chemotherapy, hormonal therapy, immunotherapy, or radiation therapy.

21. The method according to claim 17, wherein the abnormality is of a structural element and the treatment comprises at least one of repair or replacement of the structural element.

* * * * *